United States Patent [19]

Norris et al.

[11] 4,246,169

[45] Jan. 20, 1981

[54] FLAMMABLE PLASTICS CONTAINING A FLAME RETARDANT AMOUNT OF POLYARYLPHOSPHATES AND THE POLYARYLPHOSPHATES

[75] Inventors: Robert D. Norris; E. Robert Fretz, Jr., both of Cranbury, N.J.; Harry H. Beacham, Langhorne, Pa.

[73] Assignee: FMC Corporation, Philadelphia, Pa.

[21] Appl. No.: 897,614

[22] Filed: Apr. 19, 1978

[51] Int. Cl.³ .......................... C08K 5/13; C07F 9/09
[52] U.S. Cl. .............................. 260/45.95 D; 260/930
[58] Field of Search .......................... 260/930, 45.95 D

[56] References Cited

U.S. PATENT DOCUMENTS

| | | | |
|---|---|---|---|
| 2,964,477 | 12/1960 | Pilat et al. | 260/930 X |
| 3,354,240 | 11/1967 | Pochowicz | 260/930 X |
| 3,761,543 | 9/1973 | Gunsher | 260/930 |
| 3,987,008 | 10/1976 | Stackman | 260/45.95 D |

FOREIGN PATENT DOCUMENTS 1405983  9/1975  United Kingdom .................... 260/930

*Primary Examiner*—Anton H. Sutto
*Attorney, Agent, or Firm*—Abner Sheffer; Frank Ianno

[57] ABSTRACT

This invention relates to flame-retardant phosphorus-containing materials, particularly suitable for use as an additive, having little or no plasticizing effect, in flammable organic plastics. One such material may be made by reacting methallyl chloride with phenol or phenol-isopropylphenol blend and then phosphorylating. Another such material may be made by halogenating isopropyl groups of an isopropylphenyl phosphate blend and then dehydrohalogenating to make an isopropenyl-containing product, which may be oligomerized as by heating with a catalyst. The isopropenyl-containing product may also be employed as a flame-retarding comonomer.

37 Claims, 34 Drawing Figures

MAC-YLATION PRODUCT OF REPETITION OF EXAMPLE IA

FIG.2 MAC-YLATION PRODUCT OF EXAMPLE 6A

MAC-YLATION PRODUCT OF EXAMPLE 5A
SWEEP OFFSET INDICATES NO ABSORBTIONS IN REGION 8-16 PPM

MAC-YLATION PRODUCT OF EXAMPLE 7A

FIG. 5 MAC-YLATION PRODUCT OF EXAMPLE 4A

FINAL PRODUCT OF EXAMPLE 1.

GUMMY PRODUCT OF EXAMPLE 6

FINAL PRODUCT OF EXAMPLE 5

FIG. 9 FINAL PRODUCT OF EXAMPLE 4B

MAC-YLATION PRODUCT WITH 0.94 MOLES
MAC PER MOLE OF PHENOLIC MIXTURE A

MAC-YLATION PRODUCT FROM 1 MOLE MAC AND 1 MOLE PHENOL; SHORT REACTION TIME

MAC-YLATION PRODUCT FROM 1 MOLE MAC AND 1 MOLE PHENOL; LONGER REACTION TIME.

MAC-YLATION PRODUCT OF EXAMPLE 6A

FIG. 12 MAC-YLATION PRODUCT OF EXAMPLE 7A

FIG. 13 MAC-YLATION PRODUCT OF REPETITION OF EXAMPLE IA

FIG. 14 MAC-YLATION PRODUCT OF EXAMPLES 2A AND 3A

FIG. 15 MAY-YLATION PRODUCT OF REPETITION OF EXAMPLE 4A

FIG.16 NAC-YLATION PRODUCT OF EXAMPLE 5A

FIG. 17 PRODUCT EXAMPLE II

FINAL PRODUCT OF EXAMPLE I (IN CHCl₃)

FINAL PRODUCT OF EXAMPLE 2 (IN CHCl₃)

FINAL PRODUCT OF EXAMPLE 3 (IN CHCl₃)

FINAL PRODUCT OF EXAMPLE 5 (IN CHCl$_3$)

FINAL PRODUCT OF EXAMPLE 7

FINAL PRODUCT OF REPETITION OF EXAMPLE I

FIG. 27 OLEFIN INTERMEDIATE OF EXAMPLE 8

INTERMEDIATE CHLORIDE OF EXAMPLE 15

Figure 29:
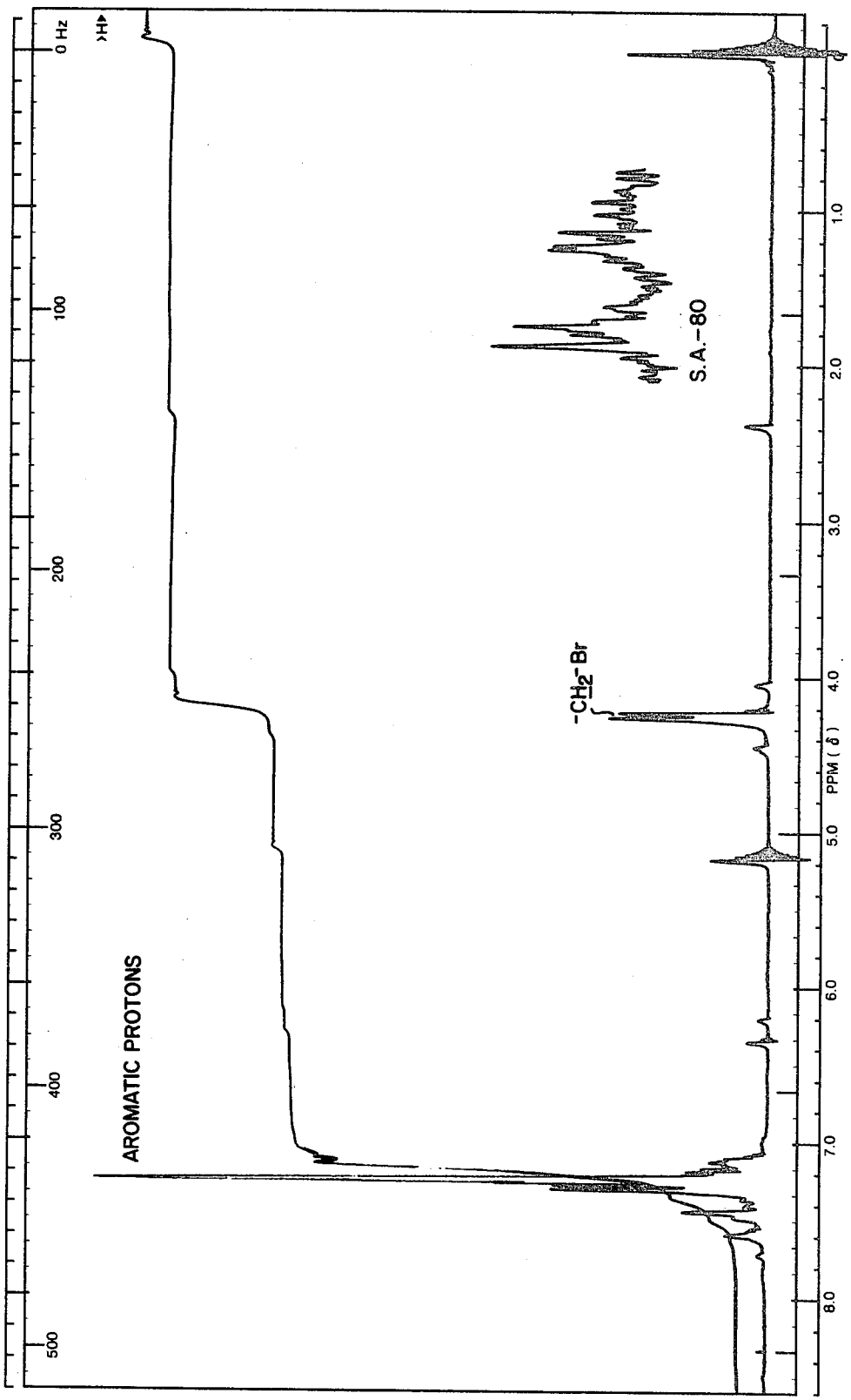
Figure 30:
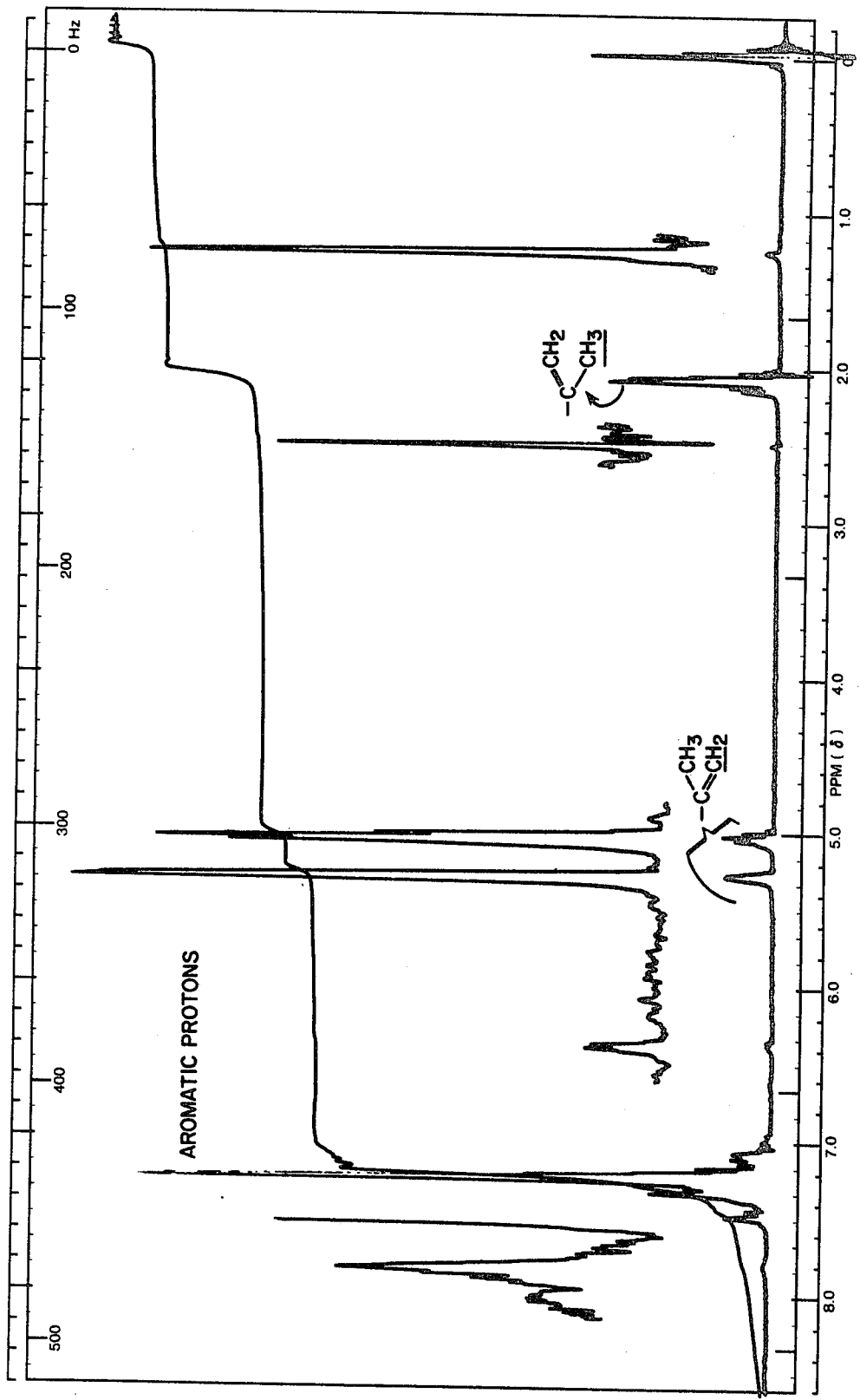

FIG. 29 PRODUCT OF EXAMPLE 16a

PRODUCT OF EXAMPLE 16b

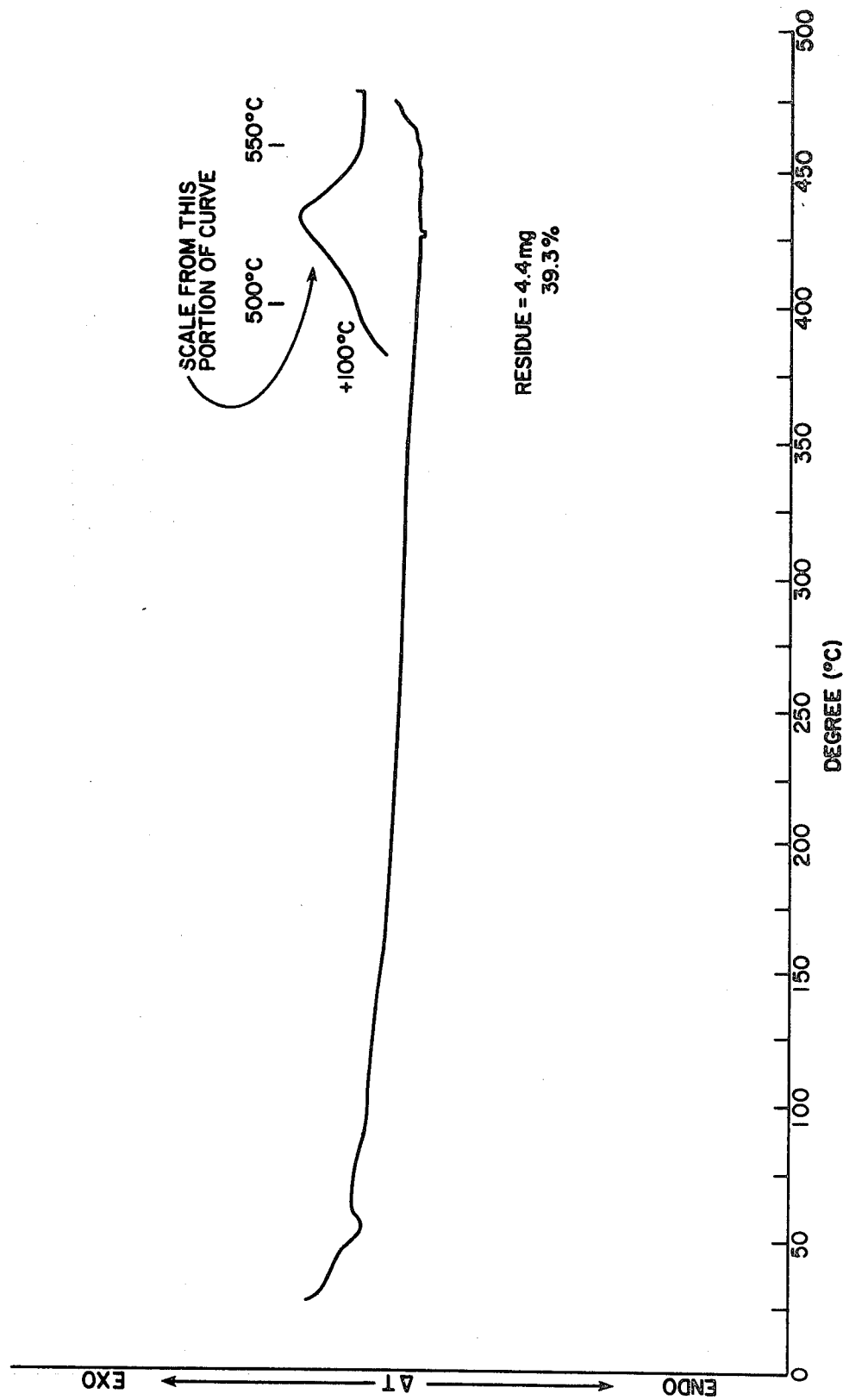

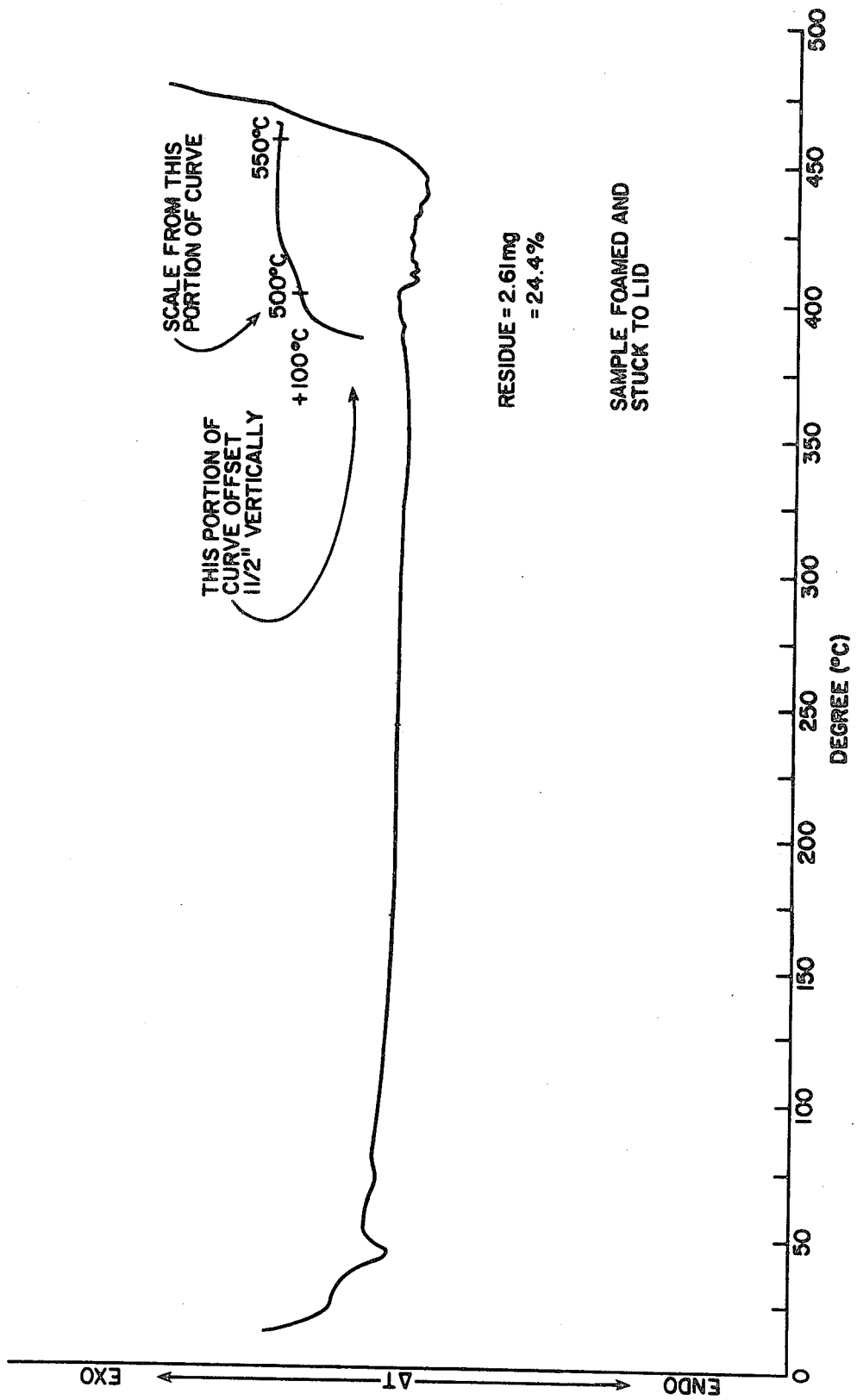
FIG. 32 PRODUCT OF EXAMPLE II

FLAMMABLE PLASTICS CONTAINING A FLAME RETARDANT AMOUNT OF POLYARYLPHOSPHATES AND THE POLYARYLPHOSPHATES

One general aspect of the invention is illustrated in Examples 1-7 below, in which the starting material is a monohydric phenol. It may be phenol as such (Examples 6 and 7), an alkyl phenol (as in Example 4) or (as in Examples 1-3 and 5) a blend of phenol and various alkyl phenols. The starting material has the general formula

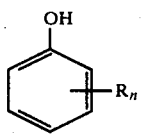  I where R is a substituent (such as lower alkyl, e.g. isopropyl); n may be zero to five, but the mixture should contain some phenols having unsubstituted, alkylatable, positions on the benzene ring. In Examples 1-7 the monohydric phenol is reacted with methallylchloride ("MAC")

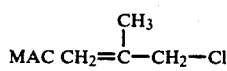

under conditions which favor reaction at the double bond of the MAC, giving compounds of the formula

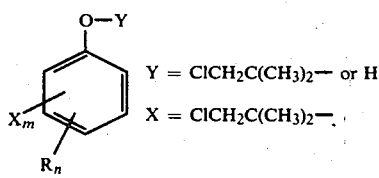  II $Y = ClCH_2C(CH_3)_2-$ or H
$X = ClCH_2C(CH_3)_2-$ in which a chlorobutyl radical may be attached to the ring directly or through the oxygen, such as chlorobutyl phenols or chlorobutyl phenyl (or substituted phenyl) ethers, where "m" is 0, 1, 2 or even 3, and "y" can be H only if "m" is 1 or above. In Examples 1-7 the resulting material (which may be termed a "MAC-ylate," or "MAC-ylation product," for short) contains unreacted alkylatable phenolic molecules. In Example 1 (in which about ⅔ mole of MAC is used per mole of phenolic material more than ⅓ of the phenolic molecules are not involved in the initial reaction with MAC ("m" is zero). In Examples 6 and 7 much less MAC is employed (about ⅓ mole or less per mole of phenol). It is, however, within the broader scope of the invention, to use greater quantities of MAC (e.g. to react 1 or 1.5 or 2 moles or more of MAC per mole of phenol). It is also within the scope of the invention to add phenol as such, or other alkylatable phenol (such as an isopropyl phenol), to the mixture after the reaction with MAC.

While the conditions in Examples 1-7 most strongly favor reaction at the double bond of the MAC they also may cause by splitting off of HCl to form compounds of the formula

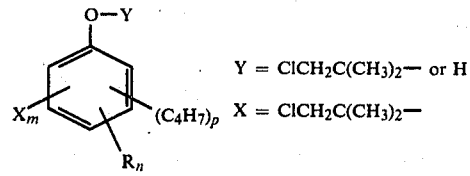  III $Y = ClCH_2C(CH_3)_2-$ or H
$X = ClCH_2C(CH_3)_2-$ in which the $C_4H_7$ radical may be an olefinic group, e.g. of the formula

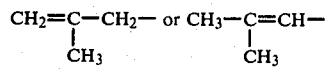

which may be attached to the ring directly or through the oxygen, [e.g. alkenyl phenols or alkenyl phenyl (or substituted phenyl) ethers] or the $C_4H_7$ radical may be a saturated divalent radical in a benzofuran (e.g. 2,2- or 3,3-dimethyl benzofuran) where "p" equals 1 in most of the molecules of this formula and may be two or more in a minor percentage of the molecules of this formula. These compounds may also be converted in the reaction mixture, to HCl adducts thereof having, for instance, chlorobutyl groups of the formula

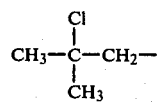

in place of the alkenyl groups.

The chloroalkyl and alkenyl substituents present in formulas II and III are reactive to alkylate the alkylatable phenols. Such alkylation may occur during the reaction with MAC (as by splitting off HCl) to form phenols which are coupled together to form di- (and higher) phenolic compounds, such as those of the following formula:

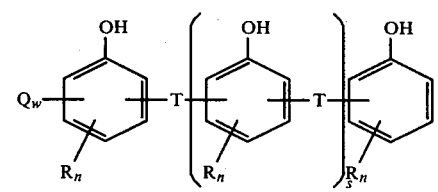  IV where "T" is a divalent branched four-carbon alkylene group (derived from the MAC, as discussed below), "Q" indicates a reactive substituent such as chloroalkyl or alkenyl (of the types present in formulas II and III) and "S" and "W" are each zero or a small number. The formula of the alkylene group ("T") may be

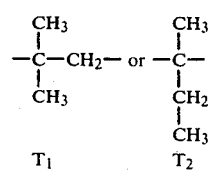

T₁    T₂

Nmr analysis indicates that both types of T groups are generally present; for instance, the final product may contain both $T_1$ and $T_2$ groups, and the $T_1:T_2$ ratio in the product may be, for example, in the range of about 1:6 to 6:1.

The degree of "T" linkage formation during the reaction with MAC may be varied; e.g. one may decrease the reaction time or reduce the temperature to decrease (or substantially avoid) formation of "T" linkages at this stage. The proportion of the coupled phenols in which there are reactive ("Q") substituents may vary; "W" may be zero in most of the coupled phenols.

Dimers and other oligomers of methallyl chloride may also be formed in the reaction, or may be present in the starting methallyl chloride or both. Such dimers, having reactive olefinic and chlorine groups may act like methallyl chloride monomer, in providing reactive substituents and "T"-like linkages (formula IV above) (but of 8 carbons instead of 4 carbons) on the phenolic compounds. A typical analysis of the methallyl chloride starting material indicates that the following compounds are also present, besides the methallyl chloride: about 0.1–0.4% 2-methyl propene-1; about 3.5–4% 1-chloro-2-methyl propene-1; about 0.6–0.8% 2-chloro-2-methyl propane; about 0.3% 1,2-dichloro-2-methyl propane. All, or some, of these "impurities" may react with the phenolic compounds during the reaction with MAC, and the difunctional impurities may have the same, or similar, effect as the MAC. It is noted that the 1,2-dichloro-2-methyl propane is an HCl adduct of MAC and may also be formed during the MAC-ylation reaction.

The MAC-ylation product is then phosphorylated. $POCl_3$ is a preferred phosphorylating agent and the phosphorylation reaction is preferably effected under conditions to promote not only phosphate ester formation but also Friedel-Crafts reaction of any reactive (e.g. haloalkyl or olefinic) groups of the aromatic compounds, described above, with the aromatic rings of compounds of formula I (and/or II and/or III and/or IV) or with phosphochloridates or phosphates thereof, resulting in the formation of "T" linkages.

When (as in Examples 1–7) the MAC-ylation product contains monofunctional phenols of formula I, the reaction with the phosphorylating agent produces triaryl phosphates of the following formula, usually in minor amount:

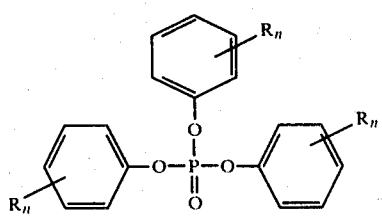

V

If the proportions and conditions of the reactions were controlled so that all the methallyl chloride acted solely to couple two phenolic moieties of formula I, the resulting phosphate ester could be a linear polymer having the formula VI below, or a branched chain polymeric material of the formula VII below, which could also be crosslinked.

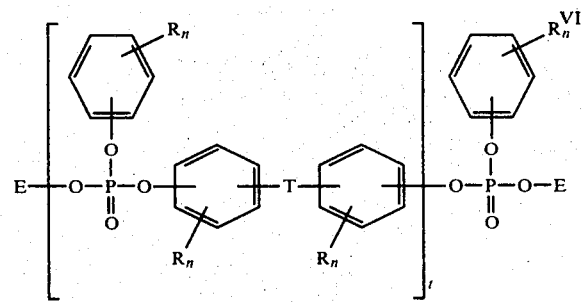

VI

In formula VI "t" is a number indicating the degree of polymerization. That degree of polymerization would then depend on the degree of molar excess of the monofunctional compounds (such as compounds of formula I which are monofunctional with respect to

that are present in the mixture, to form chain-terminating end groups which are designated as E in the above formula VI.

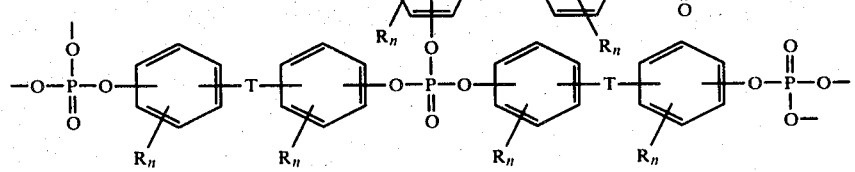

VII

In formula VII the free valences on the oxygens may be attached to monovalent end groups (such as

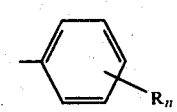

groups) or, in some cases, attached to difunctional residues. While, for simplicity, formulas VI and VII show only one "T" linkage on any given aromatic ring, it will be understood (as illustrated for instance in formula IV) that there may be two or more such "T" linkages on some of those rings.

It will be seen that the formula VII structure may form a crosslinked network. Many of the products, however, do not appear to contain a significant proportion of crosslinked material in that they are soluble; some are wholly soluble and do not show evidence of colloidal crosslinked gel particles (show no Tyndall effect).

It will be understood that, as with formula IV above, a minor proportion of the T-linked phosphate molecules may also carry one or more chloroalkyl or alkenyl substituents of the type present in formulas II and III, owing to incomplete reaction for instance.

The MAC:phenols molar ratio used in Part A of Example 1 (namely about 2:3) is such that on completion of the reaction, and without loss of reactants (e.g. due to side reactions), the product would comprise coupled phenols of formula IV with the average value of "s" being 1. That is, each molecule of methallyl chloride contributes one "T" linkage; at the 2:3 molar ratio there are two "T" linkages and three phenolic moieties. Such proportions would be expected to yield a cross-linked product if all the original phenolic groups reacted, during the phosphorylation steps, with POCl₃ without significant cyclization. Some of the phenolic groups are, however, less reactive; e.g. a phenolic group on a ring which has a substituent (such as R or T) ortho to the phenolic hydroxyl and particularly a phenolic group on a ring having two such ortho substituents (i.e. having the substituents on the 2 and 6 positions). It will be noted that the isopropyl substituents of the alkylated phenol starting material in Examples 1–3 and 5 are largely in the ortho position and that methallyl chloride may tend to react preferentially at an ortho position. In addition, cyclization (e.g. with formation of heterocyclic fused rings, such as benzofurans) may occur and thereby inactivate some of the phenolic groups. It will be noted that when the starting material is phenol, per se (as in Example 7 below) somewhat similar reaction conditions give a hard solid product even at a methallyl chloride:phenol molar ratio of about 1:3 or less.

Cyclization, with formation of large rings without crosslinking, may also occur by the bonding of a given

group (by an ester linkage) to a plurality (e.g. two) of spaced phenolic oxygens of a single molecule (which may be a molecule of a T-linked polyhydric phenol, e.g. of Formula IV, or a molecule of a T-linked phosphate, e.g. of Formula VII).

As noted below, the infrared spectrum indicates that phenolic groups are present in the final products of Examples 1–7. It is believed that these may be unreacted phenolic groups of di- or poly-functional units (e.g. one phenolic group of a compound of formula IV may react with a

group while the other phenolic group(s) may remain unreacted); thus the product may have one or more terminal units of intermediate units of the following formula:

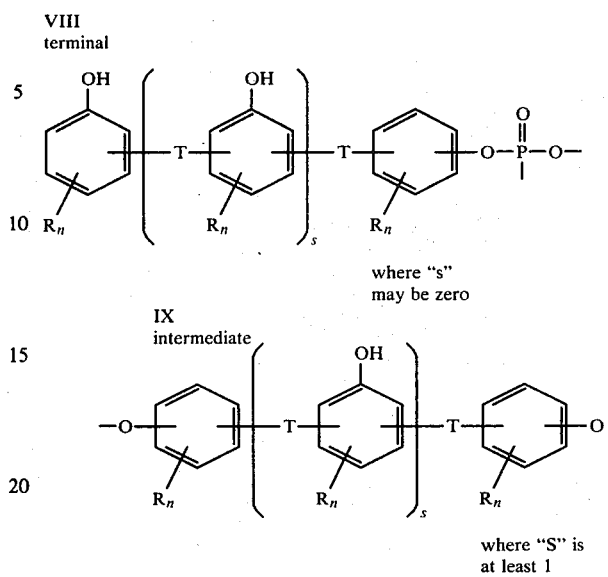

These may constitute end or intermediate groups in, for instance, formulas VI and VII. The presence of phenolic groups may account for the methanol tolerance, noted below, of many of the products.

During the reaction with POCl₃ (and, of course, with phosphochloridates formed from POCl₃) the monomeric compounds (such as monofunctional phenols and triaryl phosphates of formula VI) act as solvents or plasticizers which keep the reaction mixture fluid at the elevated temperature while the esterification and formation of T-linkages is proceeding. This may help to avoid premature crosslinking or gelation. These monomeric compounds are then preferably distilled off at subatmospheric pressure at a temperature at which the reaction mixture remains (in the Examples below) molten, although it may no longer be of readily stirrable viscosity at or near the end of the distillation.

A preferred type of catalyst for the phosphorylation reaction is a metal halide such as aluminum chloride. Preferably the residue of the catalyst remains in the product. Analysis of the product (residue of the distillation), which contains the catalyst residue indicates that the product may contain considerably less chlorine than is supplied by the catalyst. For instance the chlorine content of the product of Example 1 is about half that present in the original AlCl₃ catalyst alone, indicating that the latter may have been largely converted to materials such as aluminum phenoxides or alumina during the reaction and also indicating that essentially all the chlorine introduced by the methallyl chloride reaction has been split off (e.g. as HCl) and volatilized.

As indicated in the Examples, the reaction with POCl₃ may be carried out initially with a slight stoichiometric deficit (e.g. a 2% deficit) of POCl₃ based on the initial phenolic content (this may facilitate control of the reaction and permit maximum utilization of the T-linked, polyhydric phenols). Also un-MACylated phenols, such as phenol itself, may be added before or during the phosphorylation reaction. Thus, one may add monohydric phenols to act as "capping" agents to form end groups ("E," formula VI, for instance) to limit the growth of phosphate chains of the type shown in formulas VI and VII and/or (particularly when a high MAC:phenol ratio is used for MAC-ylation) to react with excess reactive chlorobutyl or alkenyl groups to form "T" linkages.

In the following Examples, unless otherwise indicated all proportions are by weight, all temperatures are in degrees C., all pressures are in mm Hg absolute. Unless otherwise indicated the pressure is substantially atmospheric.

EXAMPLE 1

Phenolic Mixture A

Phenol is treated with propylene in the presence of an alkylation catalyst to produce an isopropyl phenol-phenol mixture (in the manner described, for instance, in U.S. Pat. No. 3,576,923) which is then distilled at approximately 7 mm over a temperature range of 70°–120° C. to give a water white liquid distillate; gas chromatography of the distillate indicates the following composition:

|  | wt % | mole % |
|---|---|---|
| Phenol | 61 | 70 |
| 2-isopropyl phenol | 23 | 18 |
| 3- and 4- isopropyl phenols | 11 | 9 |
| 2,6-diisopropyl phenol | 2 | 1 |
| 2,4-diisopropyl phenol | 2 | 1 |
| 2,5- and 3,5-diisopropyl phenols | .6 | .3 |
| 2,4,6-triisopropyl phenol | .2 | .1 |

(A) 420 g of Phenolic Mixture A and 10 g of Clay Catalyst (Super Filtrol Grade 1) are placed in a 3-neck 1 liter round bottom flask (fitted with a magnetic stirring bar, a reflux condenser, a pressure-equalizing addition funnel and a thermometer) and the mixture is heated to 80° C. under nitrogen. Approximately 20 g of methallyl chloride (hereafter "MAC") is then added to the hot mixture over a 10 minute period. The viscosity of the mixture increases; to maintain a good suspension of catalyst, the magnetic stirring bar is replaced by a mechanical stirrer. An additional 220 g of methallyl chloride is then added over a period of about 4 hours, while temperature is maintained between 75° and 85° C., with stirring (total additional of methallylchloride is 240.7 g, corresponding to 0.68 mol of methallyl chloride per mol of phenolic materials, and to about 1 mol per mol of unsubstituted phenol. The mixture is then stirred for an additional hour during which the temperature rises to 90° C. The reaction mixture is then allowed to cool to room temperature overnight. The following day the mixture is heated to 115° C. over a period of about 1 hr and the temperature is then maintained for another 6 hr at 110°–120° C. with stirring. The mixture is again cooled to room temperature overnight. At this stage the mixture is a purple liquid, total weight 636 g, of which 10 g is the clay catalyst. This net yield of 626 g indicates that 35 g of volatile material is lost during the reaction; assuming that this is all HCl, the 35 g corresponds to about 35% of the chlorine initially present in the methallyl chloride. The material is then filtered (e.g. through a sintered glass buchner funnel under vacuum, e.g. a pressure of about 30 mm Hg) to remove the clay.

(B) 484 grams of filtered reaction mixture (produced in (A) above) and 8 grams of powdered AlCl$_3$ are placed in a 4-neck, 1 liter round bottom flask (fitted with a thermometer, a mechanical stirrer, a reflux condenser, and a pressure-equalizing addition funnel). The mixture is heated under nitrogen to 90° C. and 165 g of POCl$_3$ are added over a period of approximately 2 hours. HCl is evolved (and is trapped externally, by passing the off gas through an aqueous sodium hydroxide trap). (Based on the phenol hydroxyl content of the original distillate, prior to reaction with the methallyl chloride, the amount of POCl$_3$ added at this stage is insufficient to react with all the phenolic hydroxyls to convert them to phosphate ester groups). The temperature is gradually increased to 150° C. and maintained at 150° C. for 4 hours. The mixture is then allowed to cool to room temperature overnight. The following day the mixture is heated to 180° C. at which point vigorous refluxing takes place and, accordingly, the temperature is reduced to 170° C. (at which mild refluxing occurs) and the mixture is maintained at 170° C. for 4 hours. The temperature is then lowered to 110° C. and an additional 15 g of POCl$_3$ is added; the temperature is then raised to 180° C. over a three hour period, then the mixture is again cooled to room temperature overnight.

The following day the reaction mixture is heated to 140° C. and 30 g of Phenol Mixture A is added to react with phosphochloridate groups which may be present in the mixture. The temperature is then slowly increased to 220° C. and kept there for 5 hours. The mixture is allowed to cool to room temperature overnight. The cooled material at this time is a fairly hard mass but the surface can be scratched with a steel spatula.

The reaction mixture is heated to maintain it molten and a portion is distilled off under vacuum over a period of about 7 hours. During this distillation the absolute pressure (here expressed as mm Hg) is about 10 mm at the start and is decreased, as the distillation proceeds, to 0.2 mm at the end, and the temperature rises to about 220° C. There is obtained 99 g of a distillate containing phenols and triaryl phosphates (and probably phosphochloridates). The molten reaction mixture is then allowed to cool overnight; the next day it is reheated to keep it molten (at about 240° C.) under an absolute pressure of about 0.7 mm for about 6 hours and an additional 3 to 4 grams of distillate comes off.

Stirring is continued throughout the process, while the material is maintained molten at elevated temperature. For the distillation of the reaction mixture under vacuum, the mechanical stirrer is replaced by a magnetic stirrer (which exerts a lower torque); it is found that the molten material is, nevertheless, readily stirrable. The magnetic stirrer is usually suitable only for materials having a viscosity below 1000 cps, such as about 700 cps or less; on this basis it is believed that the viscosity of the molten material is below 1000 cps.

The residue is allowed to cool and when next inspected (some 5 days later) is found to be a hard solid having the appearance of rosin. To remove the residue the flask is placed in dry ice causing the contents to fracture (the fracture is conchoidal, like rosin) which permits the contents to be chipped out of the flask. The material is then broken into pieces (as by hacking it with a spatula) and ground to a powder using a Waring Blender; a 30 mesh screen is used to separate the larger pieces from the powder. A product weighing 373 g is obtained. Because of the crude procedure employed for removing the material from the flask significant mechanical losses (e.g. of material stuck to flask or stirrer) are encountered, probably about 30–50 g. A better procedure is to pour the molten material from the flask, e.g. onto a cold surface.

The product is completely soluble in chloroform, in that a 10% solution therein at room temperature shows no undissolved residue and no Tyndall cone visible to the naked eye. A 2-3% solution in chloroform at room temperature does not become cloudy on addition of even an equal weight of methanol. Its number average molecular weight (measured by vapor pressure osmometry in chloroform) is about 1800. The viscosity of a 10% (wt/vol) solution in chloroform at room temperature is about 0.83 centistokes.

EXAMPLE 2

Example 1 is repeated using about 0.62 mol of methallyl chloride per mol of phenolic starting material, under modified reaction conditions. More specifically:

(A) 136.7 g of Phenolic Mixture A and about 2.5 g of Super Filtrol are placed in a 3-neck, 250 ml round bottom flask (fitted with a stirrer, a reflux condenser, a pressure-equalizing addition funnel and a thermometer). The system is swept with nitrogen and heated to 70°-80° C. and 20 g of MAC is added over 2 hr. After an additional two hours at 80° C. the reaction is allowed to cool to room temperature overnight. The next day an additional 51 g of methallyl chloride is then added over a period of about 8 hours, while temperature is maintained between 70° and 95° C., with stirring (total addition of methallyl chloride is 71 g, corresponding to 0.61 mol of methallyl chloride per mol of phenolic materials, and to about 0.9 mol per mol of unsubstituted phenol). The reaction mixture is then allowed to cool to room temperature overnight. At this stage the mixture is a purple liquid, total weight 201.8 g, of which 2.5 g is the clay catalyst. This net yield of 199.3 g indicates that 8 g of volatile material is lost during the reaction; assuming this all HCl, this amount (8 g) corresponds to about 30% of the chlorine initially present in the methallyl chloride. The material is then filtered as in Example 1.

(B) 100 grams of the filtered reaction mixture and 3.5 grams of $AlCl_3$ are placed in a 4-neck, 500 ml round bottom flask (fitted with a thermometer, a mechanical stirrer, a reflux condenser, and a pressure-equalizing addition funnel). The mixture is heated under nitrogen to 90° C. and 35 g of $POCl_3$ are added over a period of approximately 1 hour. HCl is evolved (and is trapped externally, by passing the off gas through an aqueous sodium hydroxide trap). (Based on the phenol hydroxyl content of the original distillate, prior to reaction with the methallyl chloride, the amount of $POCl_3$ added at this stage is insufficient to react with all the phenolic hydroxyls to convert them to phosphate ester groups). The temperature is gradually increased to 200° C. and maintained at 200° C. for ½ hour. The mixture is then stirred at 100° C. overnight. The following day an additional 5 g of $POCl_3$ is added; the temperature is then raised to 150° C., cooled to 100° C. and 5 g of phenol added. The mixture is again heated to 210° C. and held for 1 hour. On cooling, the reaction mixture is a gummy mass.

The reaction mixture is then heated under vacuum for 7 hours as in Example 1 to give 35.8 g of distillate. The residue is allowed to cool and is found to be a hard solid (somewhat like rosin); a portion is ground (at room temperature) to form a powder.

The product is completely soluble in acetone and methylene chloride in that 10% solutions therein show no undissolved residue and no Tyndall cone visible to the naked eye. A 2% solution in chloroform does not become cloudy on addition of methanol and mixing until the methanol/chloroform ratio reaches about 3:1. Its number average molecular weight is about 1500 (measured as in Example 1).

EXAMPLE 3

(A) Part A of Example 2 is repeated.

(B) 51 g of the filtered reaction mixture, 72 g of Phenolic Mixature A and 1.8 g $AlCl_3$ are placed in a 3-neck, 250 ml round bottom flask (fitted with a thermometer, a mechanical stirrer, a reflux condenser, and a pressure-equalizing addition funnel). The mixture is heated under nitrogen to 90° C. and 36 g of $POCl_3$ are added over a period of approximately 2 hours. HCl is evolved (and is trapped externally by passing the off gas through an aqueous sodium hydroxide trap). (Based on the phenol hydroxyl content of the original distillate, prior to reaction with the methallyl chloride, the amount of $POCl_3$ added at this stage is insufficient to react with all the phenolic hydroxyls to convert them to phosphate ester groups). The temperature is gradually increased to 220° C. and maintained at 220° C. for 1 hour. The mixature is then allowed to cool to room temperature overnight. The following day the mixture is heated to 90° C. and an additional 5 g of $POCl_3$ is added; the temperature is then raised to 120° C. over a 30 minute period and 9 g of phenol is added to react with phosphochloridate groups which may be present in the mixture. The temperature is then slowly increased to 220° C. and kept there for 2 hours. The mixture is allowed to cool overnight.

The next day the mixture is transferred to a 500 ml flask and heated under vacuum to distill off volatile materials; distillation begins at a pot temperature of 87° C. and absolute pressure of 1 mm Hg and is continued until the pot temperature is 220° C.; the absolute pressure is decreased to 0.6 mm Hg at the end. The distillate comprises about 30.1 g of a lower boiling fraction (mostly phenols) and 50.2 g of higher boiling fractions (more than 90% triaryl phosphates, of which about half is triphenyl phosphate).

The residue (weighing about 45 g), on cooling is a gum which is removed from the flask by melting the gum with a blast of hot air and pouring out the molten material. It is found to be completely soluble in chloroform, in that a 10% solution therein at room temperature shows no undissolved residue. A 2-3% solution in chloroform at room temperature does not become cloudy on addition of methanol and mixing until the methanol/chloroform ratio reaches more than 2/1. The chlorine content of the product is about 0.05%. Its number average molecular weight (measured as in Example 1) is about 756; the relatively low average molecular weight may indicate that (because the lowest distillation pressure was about 0.6 mm Hg) it still contains a relatively large proportion of distillable triaryl phosphate.

EXAMPLE 4

(A) 27.6 g 2-isopropylphenol and 1 g Super Filtrol are placed in a 3-neck, 100 ml round bottom flask (fitted with a magnetic stirring bar, a reflux condenser, a pressure-equalizing addition funnel and a thermometer) and the mixture is heated to, and maintained at, 70°-80° C. under nitrogen, and 18 g MAC is added gradually to the hot mixture (about 1/5 of the MAC is added over a two hour period, then another fifth is added gradually, and then the remaining 3/5 is added over a 2 hour period) with stirring. Volatiles (such as unreacted MAC and other materials much less volatile than phenol) are then removed using a rotary evaporator under aspirator vacuum. GC analysis indicates that the residue contains a major amount (such as about 65-75%) of the unreacted 2-isopropylphenol, a lesser amount (such as about 20%) of monohydric phenols having at least one substituent in addition to the isopropyl group (probably largely 6-(chloro-t-butyl)-2-isopropylphenol) and a still smaller amount (such as about 10% of phenolic compounds having at least two phenolic hydroxyls.

(B) 15.6 g of the product is then mixed with 0.5 g $AlCl_3$, heated to 90° and then 4.9 g of $POCl_3$ is added over a period of about ½ hour to the hot mixture and the reaction is continued with heating to produce the phosphate esters; in this case the step of removing the "monomeric" triaryl phosphates after phosphorylation, by vacuum distillation at high temperature, is omitted. The product is a gum (at room temperature) soluble in methylene chloride.

EXAMPLE 5

Phenolic Mixture B

Phenol is alkylated as in the making of Mixture A, but using a larger proportion of propylene; similar distillation gives a mixture (B) having the following composition, by gas chromatography:

|  | wt % | mole % |
|---|---|---|
| Phenol | 47.5 | 58.0 |
| 2-isopropyl phenol | 28.0 | 23.7 |
| 3- and 4-isopropyl phenols | 14.1 | 11.9 |
| 2,6-diisopropyl phenol | .5 | 0.3 |
| 2,4-diisopropyl phenol | 4.4 | 2.8 |
| 2,5- and 3,5-diisopropyl phenols | 4.1 | 2.6 |
| 2,4,6-triisopropyl phenol | 1.3 | 0.7 |

(A) 100 g of Phenolic Mixture B is placed in a 3-neck, 250 ml round bottom flask (fitted with a magnetic stirring bar, a reflux condenser, a pressure-equalizing addition funnel and a thermometer) and the mixture is heated to 85° C. under nitrogen. 2 g of $AlCl_3$ are added, then 60 g of methallyl chloride is added over a period of about 1 hour. The temperature rises to 110° C. during the addition (indicating an exothermic reaction). The temperature is reduced to 75° C. and finally maintained at 90° C. for 4 hours. The amount of MAC corresponds to 0.71 mol per mol of phenolic materials, and to about 1.2 mol per mol of unsubstituted phenol. The reaction mixture is then allowed to cool to room temperature overnight. The following day the mixture is heated to 125° C. over a period of about 1 hour and the temperature is then maintained for another 6 hours at 110°–120° C. with stirring. The mixture is again cooled to room temperature overnight and filtered.

(B) 116 grams of the reaction mixture (still containing the $AlCl_3$) is placed in a 3-neck, 250 ml round bottom flask (fitted with a thermometer, a mechanical stirrer, a reflux condenser, and a pressure-equalizing addition funnel). The mixture is heated under nitrogen to 90° C. and 39 g of $POCl_3$ is added over a period of approximately 2 hours. HCl is evolved and is trapped externally, by passing the off gas through an aqueous sodium hydroxide trap. Based on the phenol hydroxyl content of the original distillate, prior to reaction with the methallyl chloride, the amount of $POCl_3$ added at this stage is insufficient to react with all the phenolic hydroxyls to convert them to phosphate ester groups. The temperature is gradually (over a two hour period) increased to 160° C. The mixture is then allowed to cool overnight to room temperature. The following day the mixture is heated to 220° C. over a 2 hour period and maintained at 220° C. for 1 hour, then lowered to 90° C., an additional 5 g of $POCl_3$ is added, and the temperature is then raised to 225° C. for a 30 minute period. The mixture is then cooled to 150° C., and 10 g of Phenolic Mixture A is added to react with phosphochloridate groups which may be present in the mixture. The temperature is then slowly increased to 220° C. and kept there for 2 hours. The mixture is allowed to cool overnight to room temperature. It is thereafter subjected to high temperature vacuum distillation (similar to that used in Example 1B).

The product is a solid, which resembles rosin in appearance and which can be ground to a powder. It is soluble in chloroform; a 10% solution therein at room temperature shows no undissolved residue and no Tyndall cone visible to the naked eye. A 2–3% solution in chloroform at room temperature does not become cloudy on addition of methanol and mixing until the methanol/chloroform ratio reaches 1:1. Its molecular weight (measured as in Example 1) is about 1550.

EXAMPLE 6

968 g of phenol and 20 g Super Filtrol are placed in a 3-neck, 2-liter round bottom flask (fitted with a mechanical stirrer, a reflux condenser, a pressure-equalizing addition funnel and a thermometer) and the mixture is heated to 80° C. under nitrogen. 290 g of methallyl chloride (0.31 mol per mol of phenol) is then added to the hot mixture over a 4 hr period. The viscosity of the mixture increases. Temperature is maintained between 80° and 100° C., with stirring. The mixture is then stirred for an additional 2 hours during which the temperature is kept at 100° C. The reaction mixture is then allowed to cool to room temperature overnight. The following day the mixture is hearted to 120° C. over a period of about 2 hrs and the temperature is then maintained for another 6 hrs at 110°–120° C. with stirring. The mixture is again cooled overnight to room temperature and filtered. At this stage the mixture is a purple liquid (Cl content 0.7%).

(b) 1034 grams of the filtered reaction mixture and 20 grams of $AlCl_3$ are placed in a 4-neck, 2 liter round bottom flask (fitted with a thermometer, a mechanical stirrer, a reflux condenser, and a pressure-equalizing addition funnel). The mixture is heated under nitrogen to 90° C. and 447 g of $POCl_3$ is added over a period of approximately 3 hours. HCl is evolved (and is trapped externally, by passing the off gas through an aqueous sodium hydroxide trap). Based on the phenol content prior to reaction with the methallyl chloride, the amount of $POCl_3$ added at this stage is insufficient to react with all the phenolic hydroxyls to convert them to phosphate ester groups. The temperature is gradually increased to 125° C. and maintained at 125° C. for ½ hour. The mixture is then allowed to cool overnight to room temperature. The following day the mixture is heated to 200° C. and maintained at 200° C. for 1 hour. The temperature is then lowered to 110° C. and an additional 25 g of $POCl_3$ is added; the temperature is then raised to 205° C. and the temperature maintained for 2 hours; then the mixture is again cooled overnight to room temperature.

The following day the reaction mixture is heated to 140° C. and 40 g phenol is added to react with phosphochloridate groups which may be present in the mixture. The temperature is then slowly increased to 215° C. and kept there for 2 hours. The mixture is allowed to cool overnight to room temperature, forming a tacky gum. The mixture is quite viscous and difficult to stir at temperatures such as 40° C. and 70° C. It stirs easily at 120° C.

The mixture is then heated under vacuum to distill off volatile materials for about 7 hours under approximately the following conditions:

| pot temp °C. | head temp °C. | pressure mm Hg | cumulative total amount of distillate (g) |
|---|---|---|---|
| 160 | 80 | 10 | 20 |
| 178 | 78 | 0.35 | 50 |
| 230 | 190 | 0.3 | 120 |
| 248 | 197 | 0.3 | 170 |

The residue is cooled to about 140° C. and poured into a metal beaker (under nitrogen). The mixture is allowed to cool overnight. The solid mass is cooled in a dry ice bath and the then-brittle material is broken into fragments and ground to a powder in a Waring blender; on standing at room temperature overnight the powder material flows together to form a unitary mass. The product is soluble in chloroform; its molecular weight (measured as in Example 1) is about 1140. On further vacuum distillation (to drive off phenols and triaryl phosphates) a friable rosin-like material is obtained.

EXAMPLE 7

(A) 1000 g of phenol and 20 g of Super Filtrol are placed in a 3-neck, 2 liter round bottom flask (fitted with a magnetic stirring bar, a reflux condenser, a pressure-equalizing addition funnel and a thermometer) and the mixture is heated to 80° C. under nitrogen. 330 g of methallyl chloride (0.32 mol per mol of phenol) is then added over a period of about 2 hours, while temperature is maintained between 75° and 85° C., with stirring. The mixture is then stirred for an additional 30 minutes during which the temperature rises to 90° C. The reaction mixture is then allowed to cool overnight to room temperature. The following day the mixture is heated to 115°–120° C. over a period of about 2 hours and that temperature is then maintained for another 4 hours with stirring. The mixture (1205 g) is filtered while still warm, 60°–70° C., to give 1158 g of purple liquid. Assuming that the loss in weight (before filtering) is all HCl, it corresponds to about 89% of the chlorine originally present in the methallyl chloride.

(B) 1131 grams of the (unfiltered) reaction mixture and 22 grams of $AlCl_3$ are placed in a 4-neck, 3 liter round bottom flask (fitted with a thermometer, a mechanical stirrer, a reflux condenser and a pressure-equalizing addition funnel). The mixture is heated under nitrogen to 90° C. and 500 g of $POCl_3$ is added over a period of approximately 6 hours. HCl is evolved (and is trapped externally, by passing the off gas through an aqueous sodium hydroxide trap). (Based on the phenol content prior to reaction with the methallyl chloride, the amount of $POCl_3$ added at this stage is insufficient to react with all the phenolic hydroxyls to convert them to phosphate ester groups). The temperature is gradually increased to 120° C. and maintained at 120° C. for ½ hour. The mixture is then allowed to cool overnight to room temperature. The following day the mixture is heated to 205° C. over 2½ hours and maintained at that temperature for another ¼ hour. The temperature is then lowered to 110° C. and an additional 50 g of $POCl_3$ is added; the mixture is then kept at 235° C. for a one hour period, and then again cooled overnight to room temperature.

The following day the reaction mixture is heated to 130° C. and 50 g of phenol is added to react with phosphochloridate groups which may be present in the mixture. The temperature is then slowly increased to 220° C. and kept there for 4 hours. The mixture is allowed to cool overnight to room temperature.

The reaction mixture is vacuum distilled at high temperature while molten; during this process pot temperature is raised to 258° C. and absolute pressure is decreased from 9 mm to 0.2 mm Hg over a 7 hour period. 5.6 g of a distillate, largely phenols, is obtained. After cooling overnight the mixture is reheated to keep it molten (240° C.) under vacuum (0.2 mm Hg) for 6 hours and an additional 166 grams of distillate (namely trialkyl phosphates and phosphochloridates) comes off. On cooling, the residue is found to be a hard solid having the appearance of rosin. To remove the residue (1147 g) the flask is placed in dry ice causing the contents to fracture (the fracture is conchoidal, like rosin) which permits the contents to be removed from the flask. The material is then broken into pieces and ground to a powder using a Waring Blender; a 30 mesh screen is used to separate the larger pieces from the powder.

The product is insoluble in chloroform and in methylene chloride, at room temperature, but swells noticeably (e.g., by about 20% or more) in those liquids, and the swollen particles of powder appear to be sticky (they tend to adhere to the glass wall of the test tube containing the powder and liquid swelling agent). On testing for its solubility the following liquids, it is found to be substantially insoluble (on testing at room temperature and at temperatures up to about 80° C.) in 2-isopropylphenol, triaryl phosphate III (described below), dimethylformamide, dimethylsulfoxide, and pyridine.

In each of the foregoing Examples 1–7 the MAC is dripped into the blend of phenolic material and catalyst which is maintained at about atmospheric pressure and at a temperature (e.g. about 80° C.) a few degrees above the boiling point (about 72° C.) of MAC, under a reflux condenser. Under these conditions substantially all the MAC appears to be retained in the reaction mixture, for reaction with the phenolic material. It will be understood that other techniques may be used; for instance, one may mix the phenolic material, MAC and catalyst at room temperature and then heat it up to reaction temperature. The reaction may be effected at higher temperatures (e.g. under superatmospheric pressure) and/or the MAC may be fed to the reaction mixture in gaseous or vapor state and bubbled into the mixture, instead of supplying it as a liquid.

All the reactions in the foregoing Examples are effected under a stream of house nitrogen to keep out significant amounts of oxygen and moisture and under continuous stirring. During the high vacuum distillations a magnetic stirrer is used, as described in Example 1.

The materials described as "gums" are relatively soft solids; when the end of a steel spatula is pushed into the solid the solid yields and adheres to the spatula.

As noted in the Examples above the products may be gums or grindable solids. The grindable solids generally break with a conchoidal fracture (like rosin) and are converted to a gummy state on heating, while the gums usually become brittle and grindable on cooling (e.g., at −80° C.). On testing the melting behavior of the products in a Mettler FPI apparatus, which gives the results as a curve of temperature ("x" axis) vs. light transmission (through the powdered sample in a glass melting-point tube) on the "y" axis, the following results are obtained at the indicated heating rates. In the tabulation below, "A" designates the approximate temperature of initial upward inflexion of the curve (indicating beginning of softening or melting); "B" designates the approximate temperature at which the curve begins to rise rapidly; and "C" designates the approximate temperature at which the curve levels off.

| Example | Heating rate °C./min | A | B | C |
|---|---|---|---|---|
| 1 | 10 | 60 | 93 | 107 |
| 1 | 2 | 55 | 88 | 102 |
| 2 | 10 | 45 | 62 | 94 |
| 3 | | gum | | |
| 5 | 10 | 55 | 62 | 87 |
| 6 | | gum, powder flows together on standing. | | |
| 7 | 2 | 80–200 | 230 | 270 |

In the test of the Example 7 material a slight change is noted beginning at about 80° C., the rate of change begins to be more marked at about 200°, the curve starts to become steep at about 230°; on inspection of the tube which has been heated to 270° in the test shows particles sticking to the walls of the tube indicating that the melt viscosity of the material is high even at that temperature.

Figure 1:
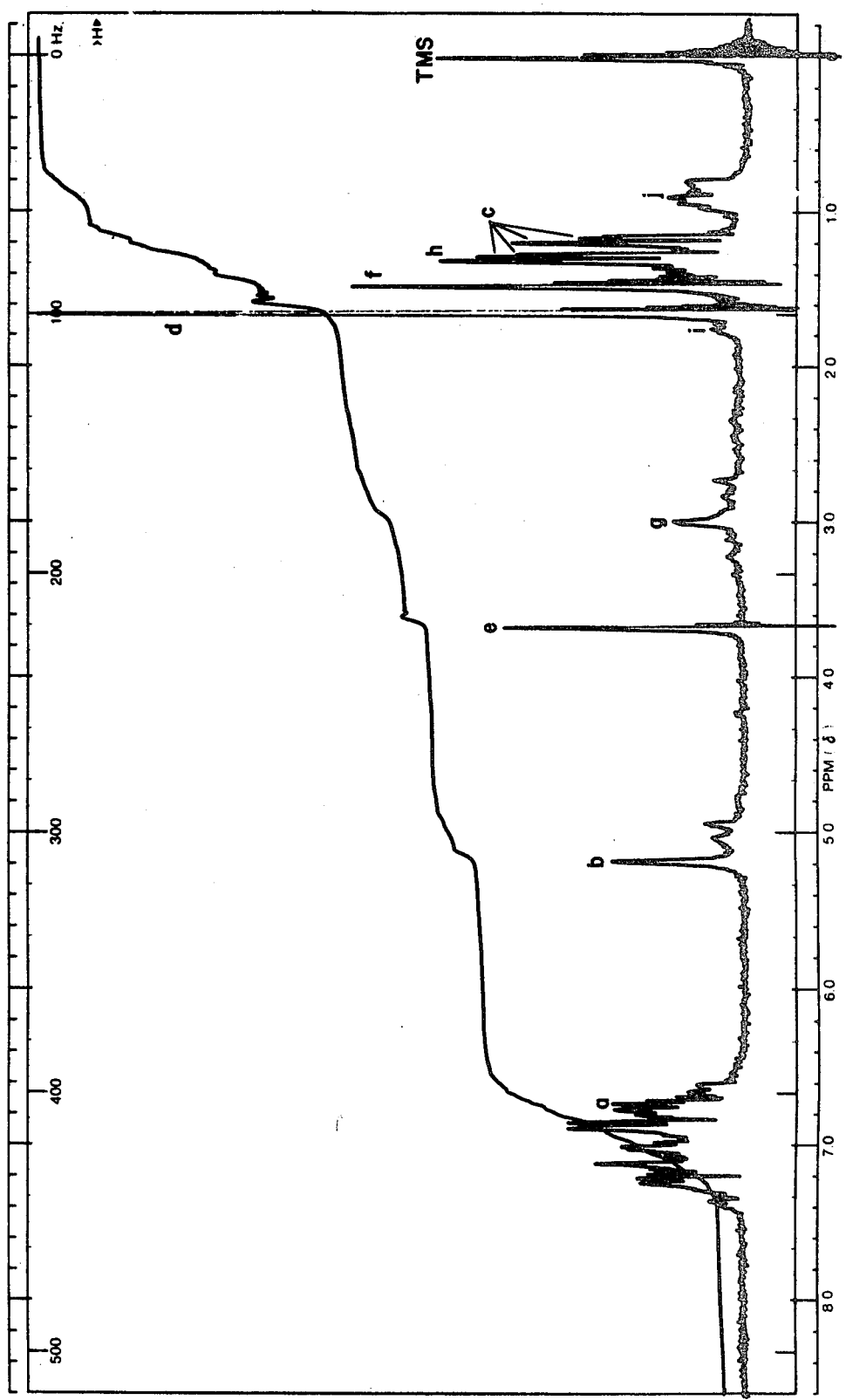
Figure 2:
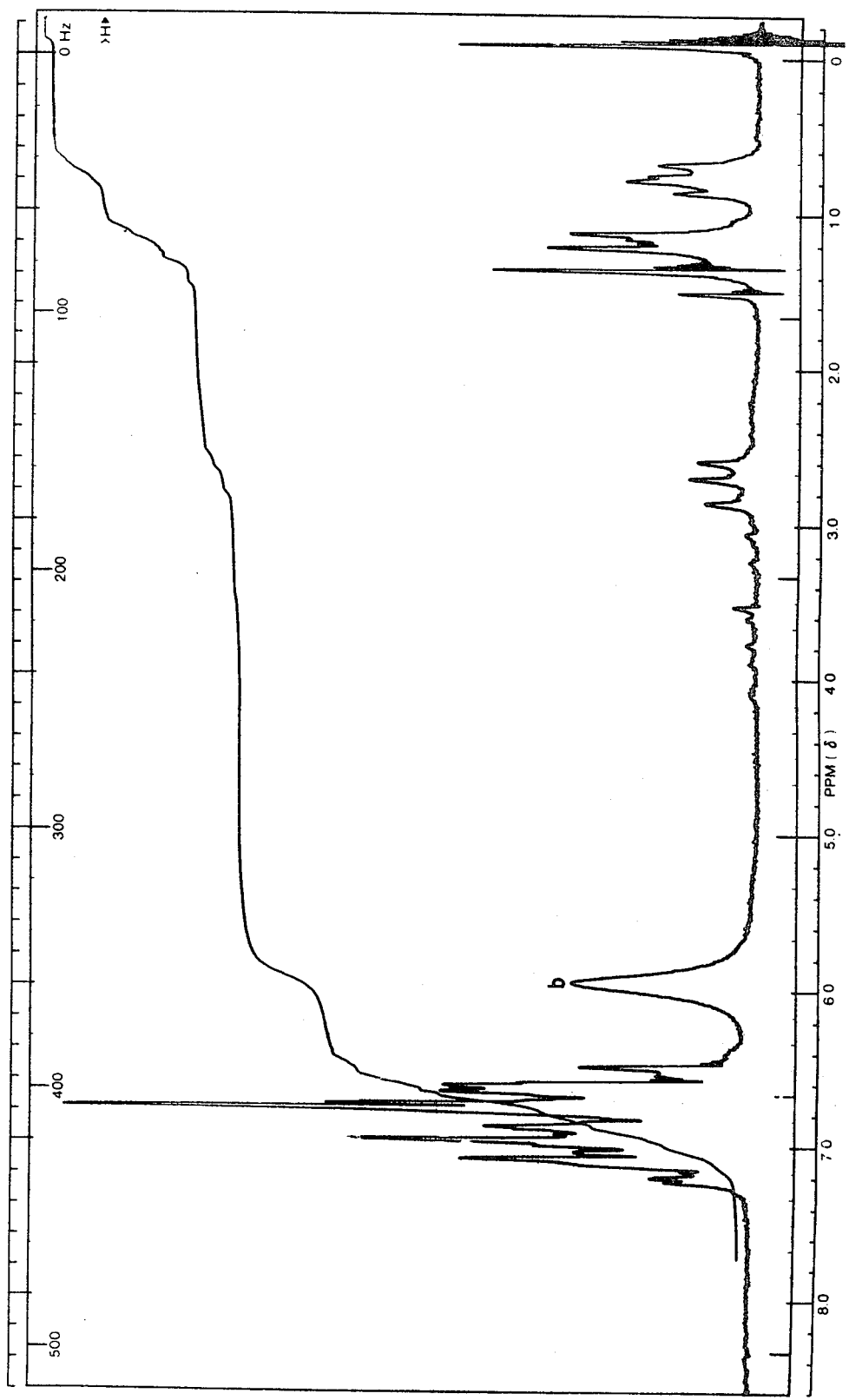
Figure 3:
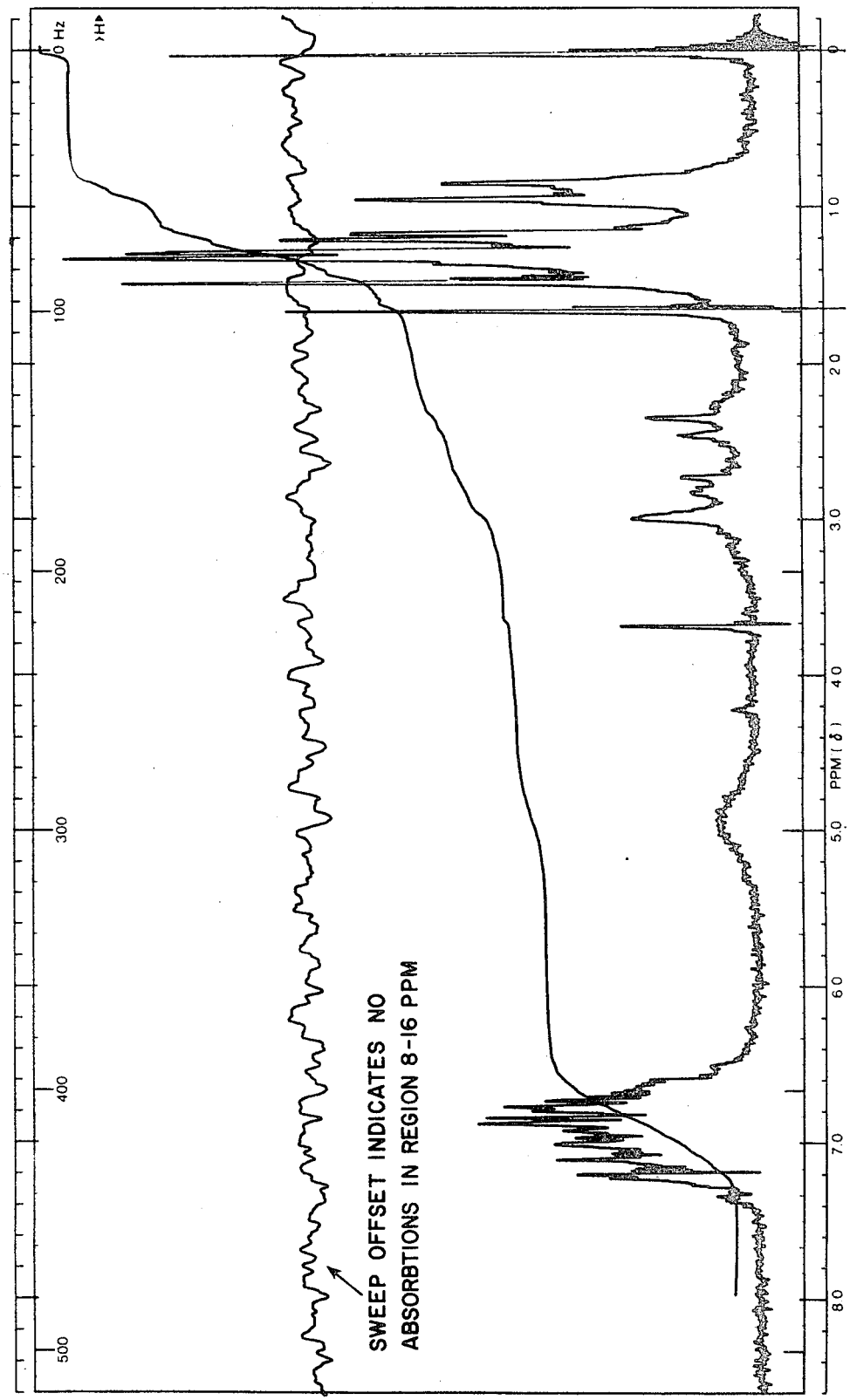
Figure 4:
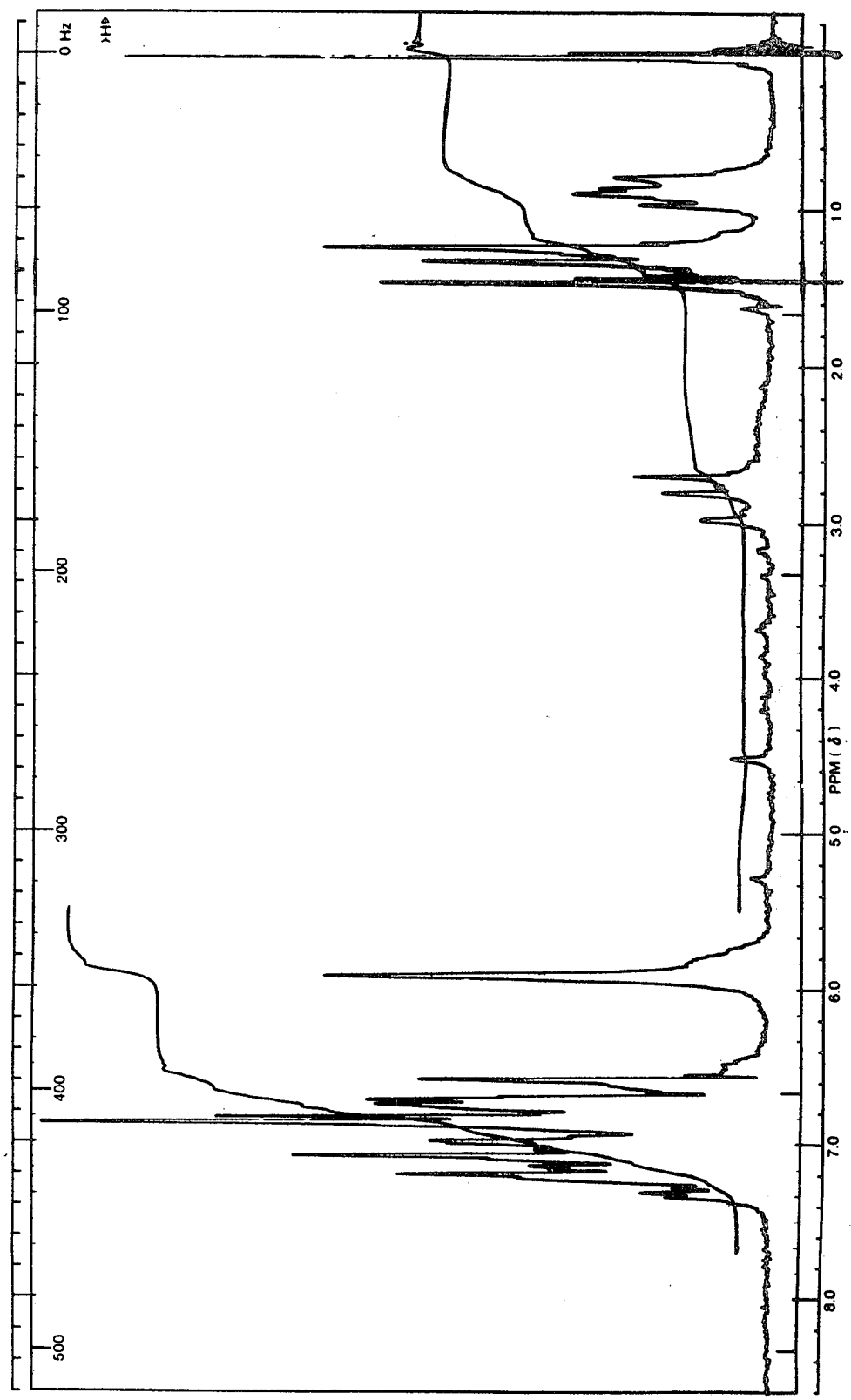
Figure 5:
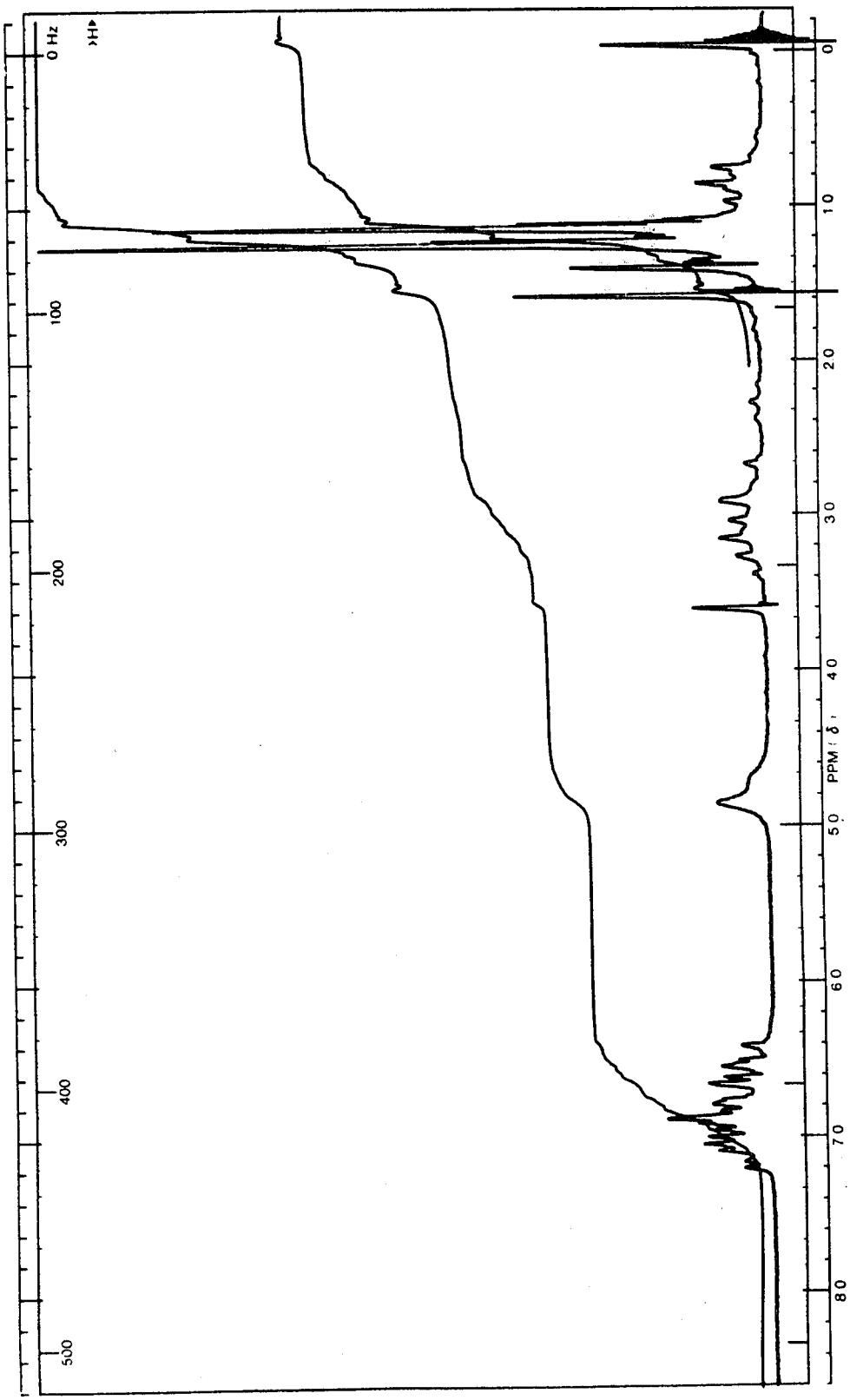
Figure 6:
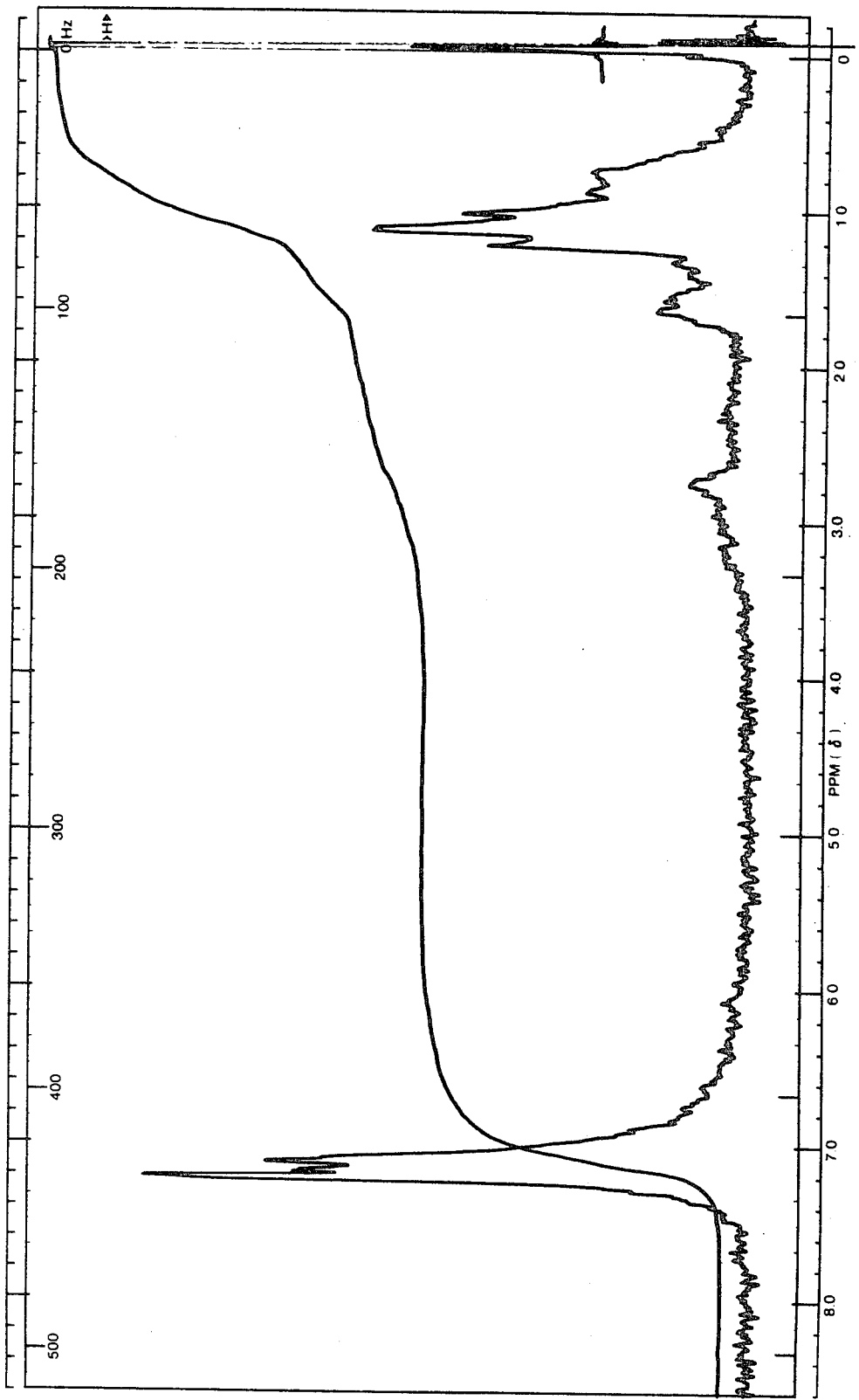
Figure 7:
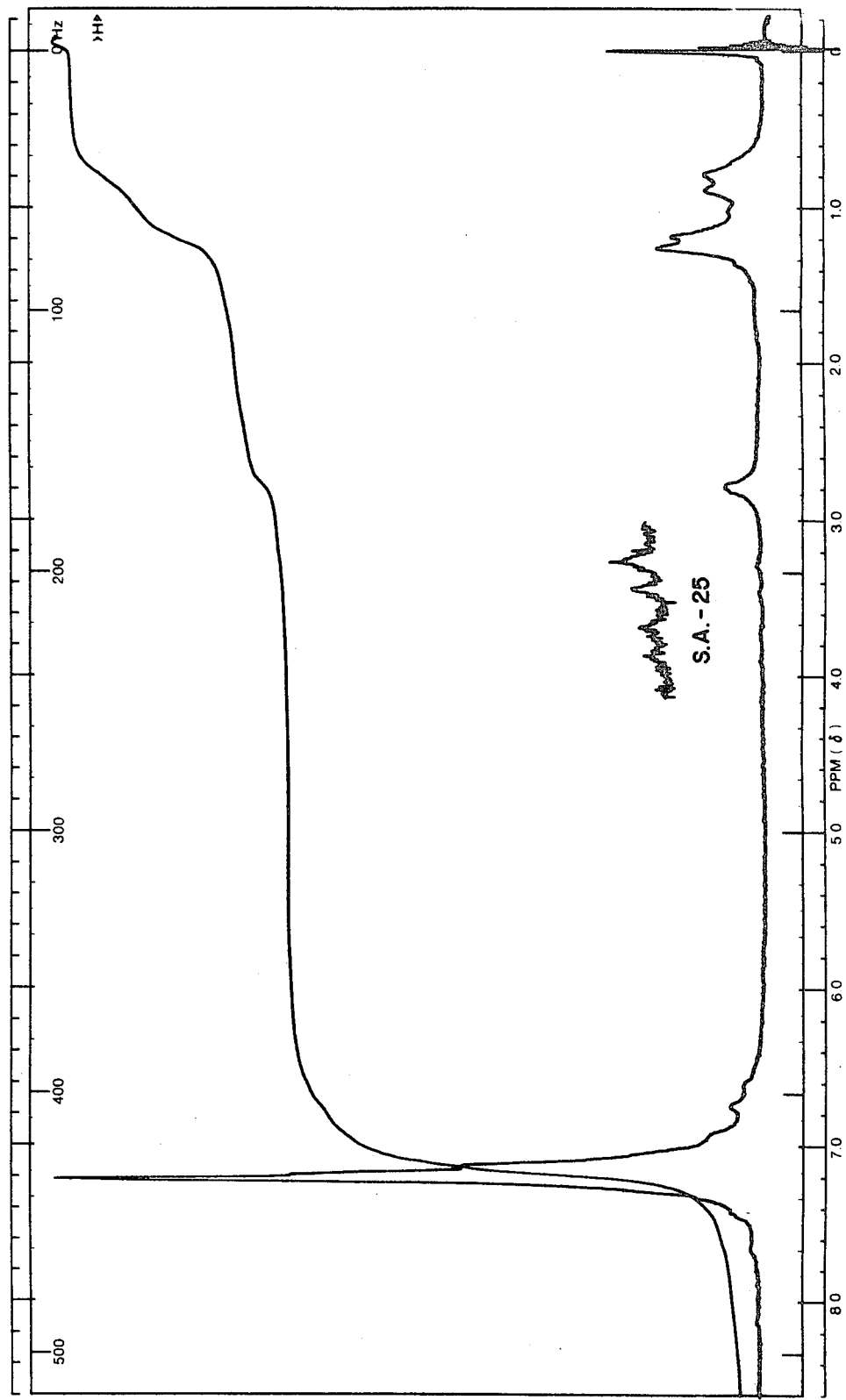
Figure 8:
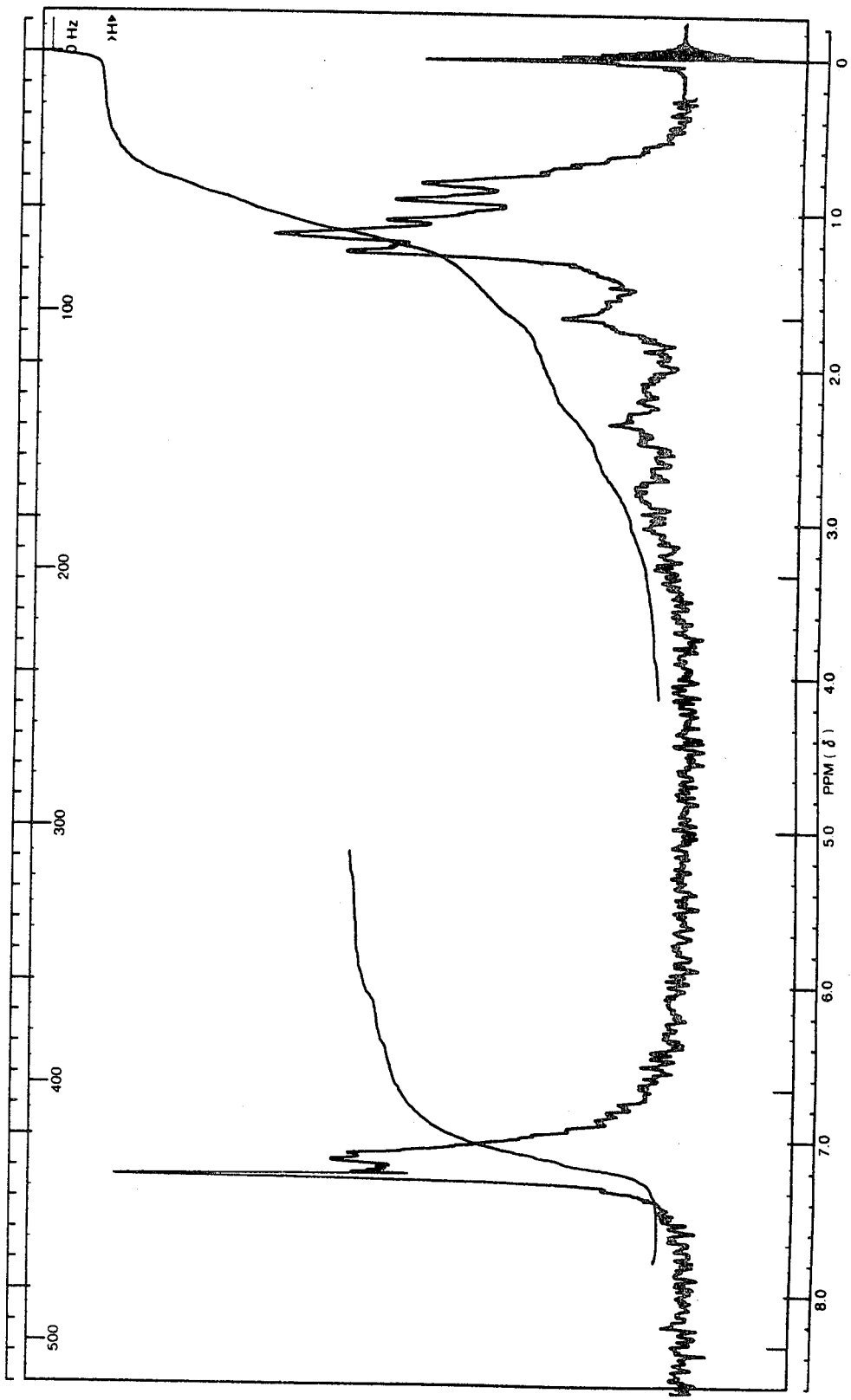
Figure 9:
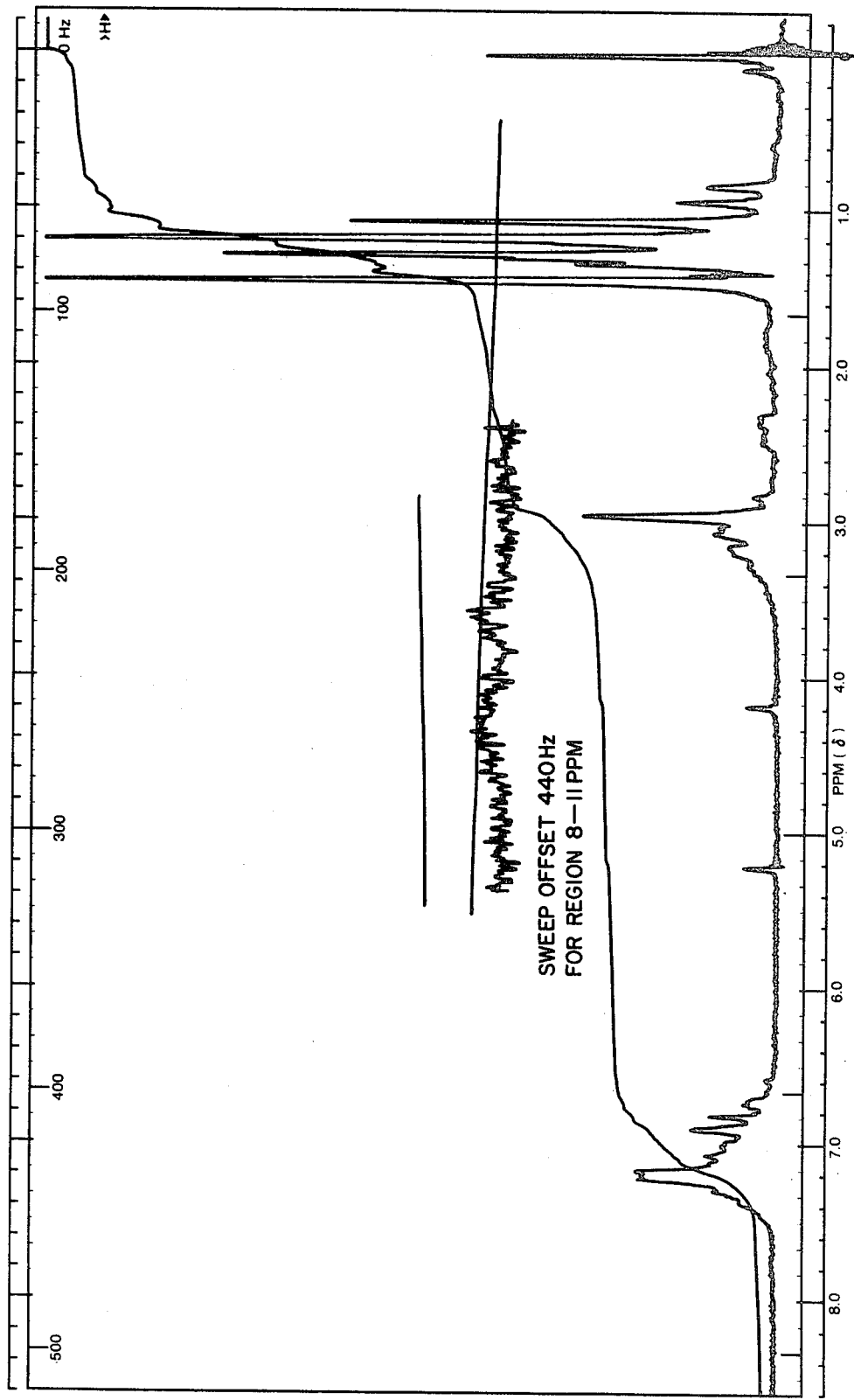

FIGS. 1–9 are nmr (taken at 60 MH$_2$ in CDCl$_3$) of the final products or MAC-ylation products of various Examples, as indicated on the FIGS. The MAC-ylation products show aromatic protons at about 7 ppm (see peaks "a", FIG. 1); hydroxyl protons at about 5–6 ppm (see peaks "b" at 5.2 ppm in FIG. 1 at about 6 in FIG. 2). They also show peaks for isopropyl groups where present (see the multiplets at about 3 ppm and the doublets at about 1.2 ppm in FIG. 1, as expected for an isopropyl substituent on an aromatic ring, as in cumene). They also show evidence of 2-chloro-1,1,-dimethylethyl groups; thus in FIG. 1 there are singlets at 1.65 ppm (marked "d") and at 3.63 ppm ("e") in the correct 3:1 ratio (analogously, neopentyl chloride is known to show peaks at 1.58 and 3.3 ppm, in CCl$_4$, and the aromatic ring in applicants' products would be expected to cause a downfield shift).

Evidence for the T$_1$ linkage is found in the singlets at 1.43 ppm and about 2.9–3.0 ppm (marked "f" and "g" in FIG. 1) which are in the appropriate 3:1 ratio for the protons in the formula —CH$_2$—C(CH$_3$)$_2$—. (Analogously t-butylbenzene shows a peak at 1.32 ppm and 1,2-diphenylethane shows a peak at 2.87 ppm, in CCl$_4$).

Evidence for the T$_2$ linkage which has the formula CH$_3$—C—CH$_2$—CH$_3$ is found in the singlet at 1.28 ppm corresponding to the three protons on the left hand carbon (this singlet, indicated at "h" in FIG. 1, may be masked or buried in the isopropyl overlapping doublets in some Figs.); the multiplet at about 1.6–1.8 ppm (see "i" in FIG. 1) corresponding to the two protons on the methylene carbon); and the multiplet at about 0.9 ppm (see "j" in FIG. 1) corresponding to the three protons on the right hand carbon. Analogously 2-phenylbutane shows a singlet at 1.23 ppm, a multiplet at 1.7 ppm and a multiplet at 0.79 ppm in CCl$_4$.

Figure 10:
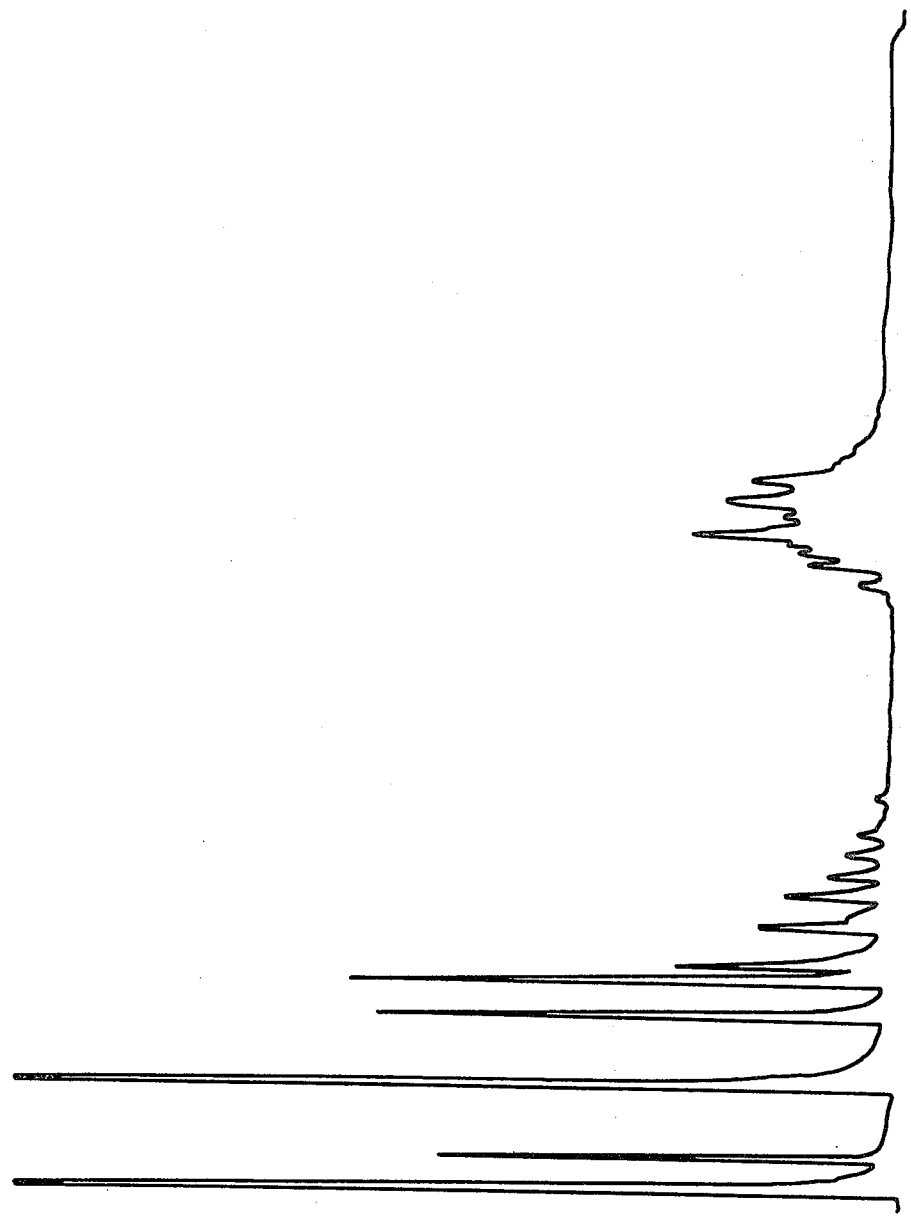
Figure 10A:
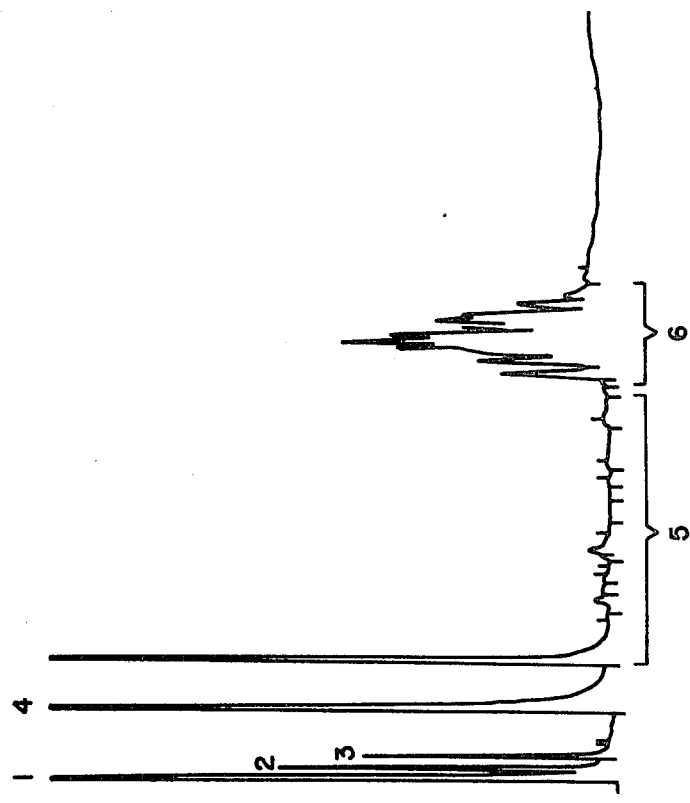
Figure 10B:
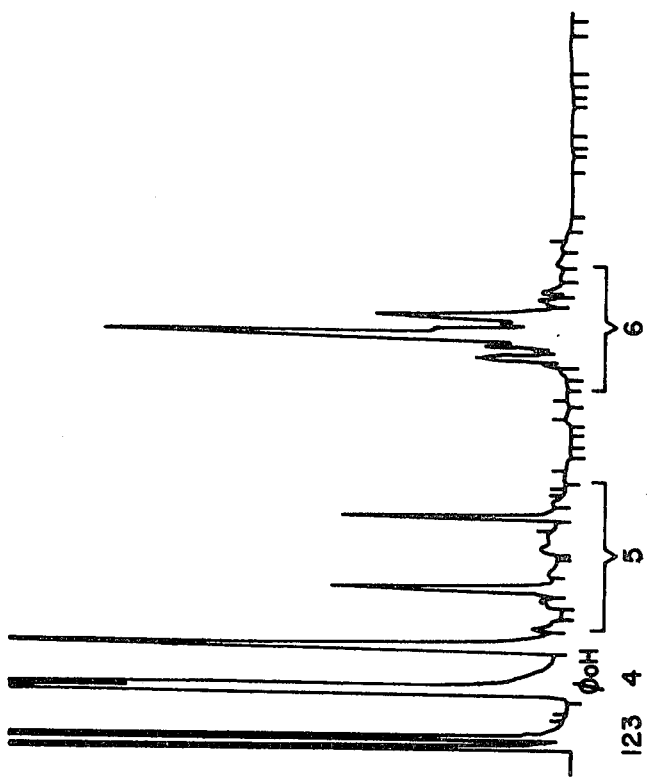
Figure 11:
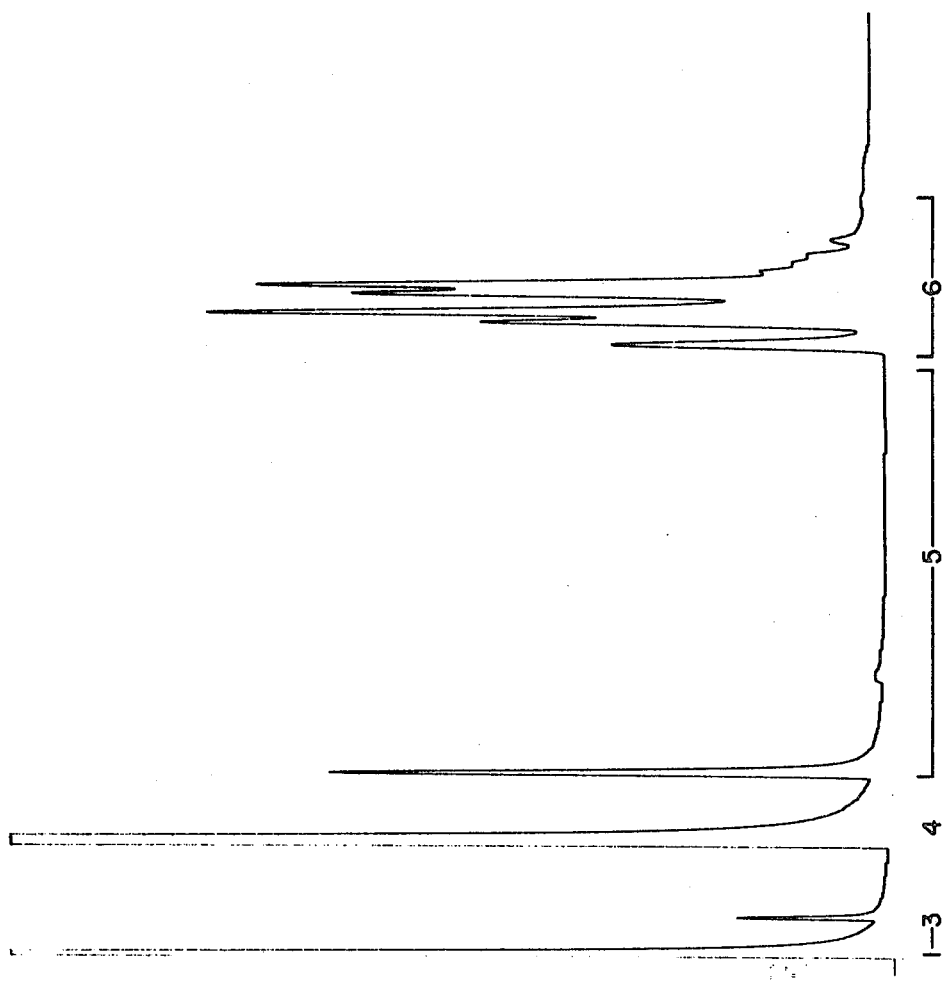
Figure 12:
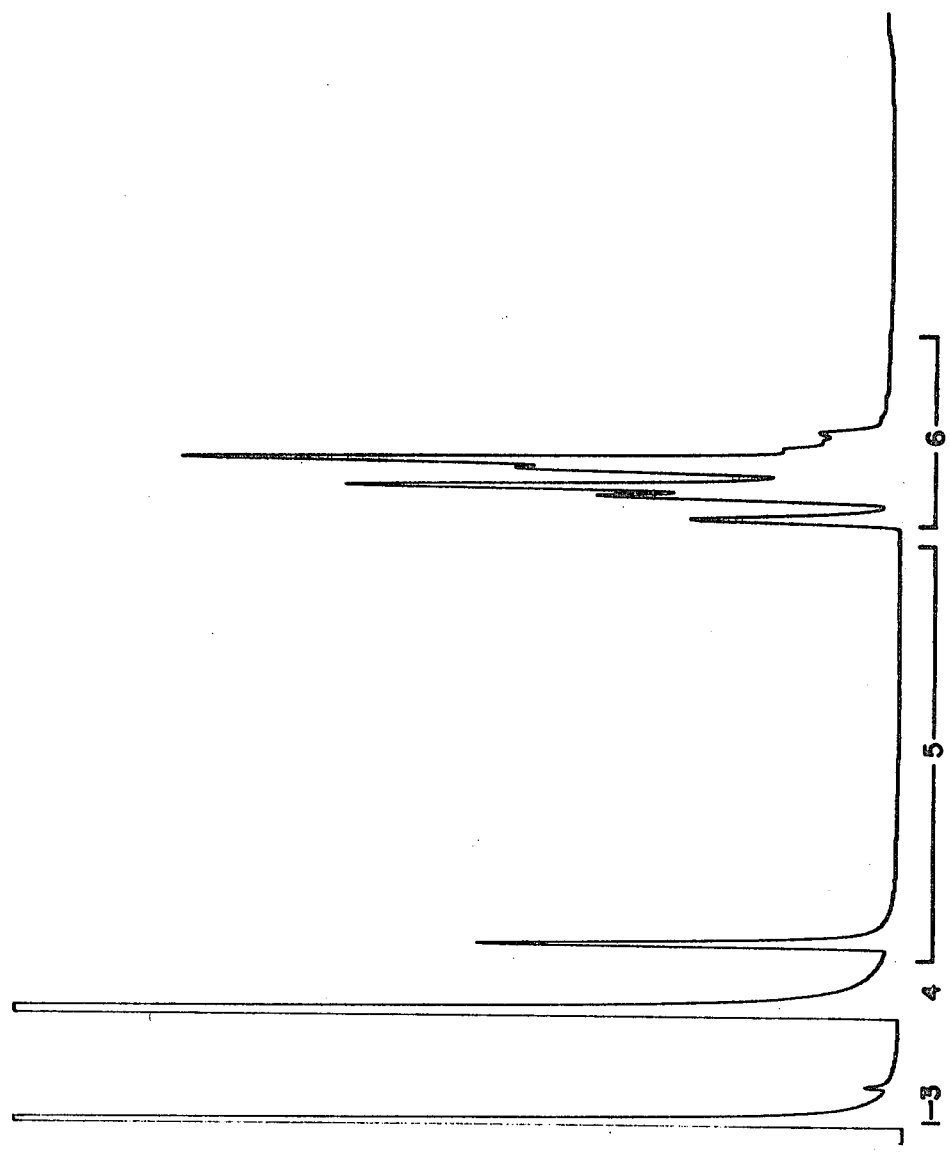
Figure 13:
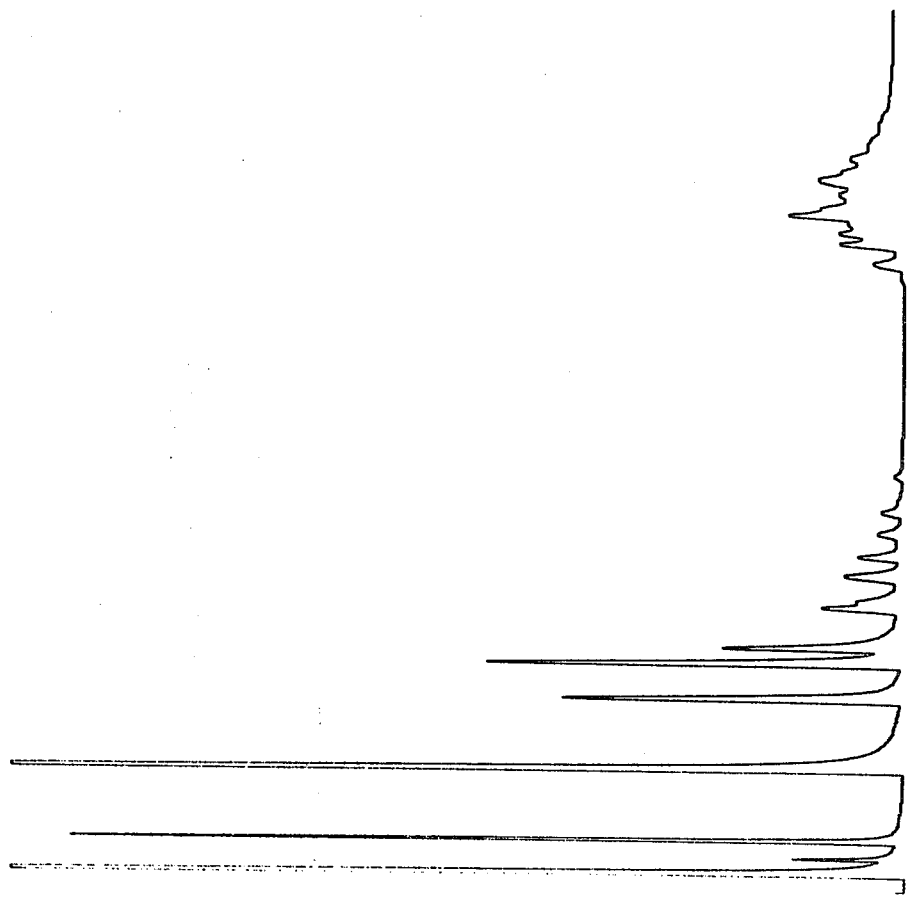
Figure 14:
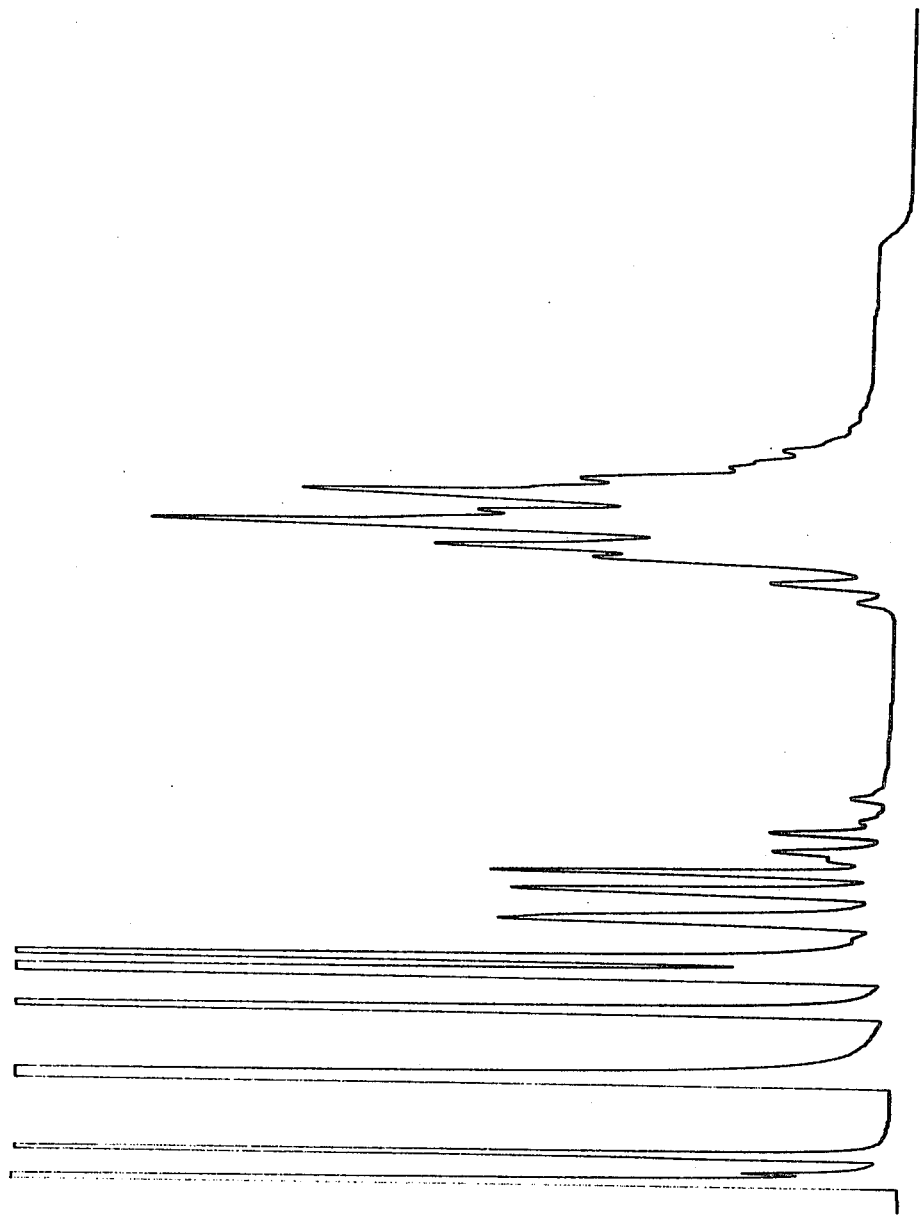
Figure 15:
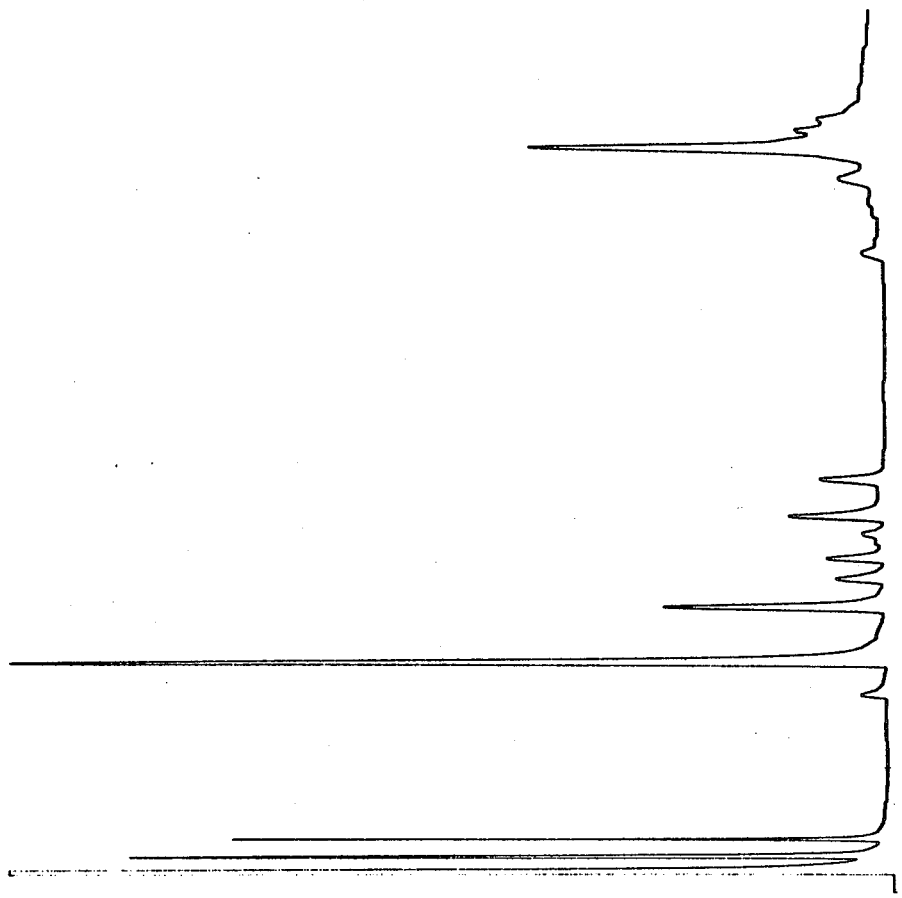
Figure 16:
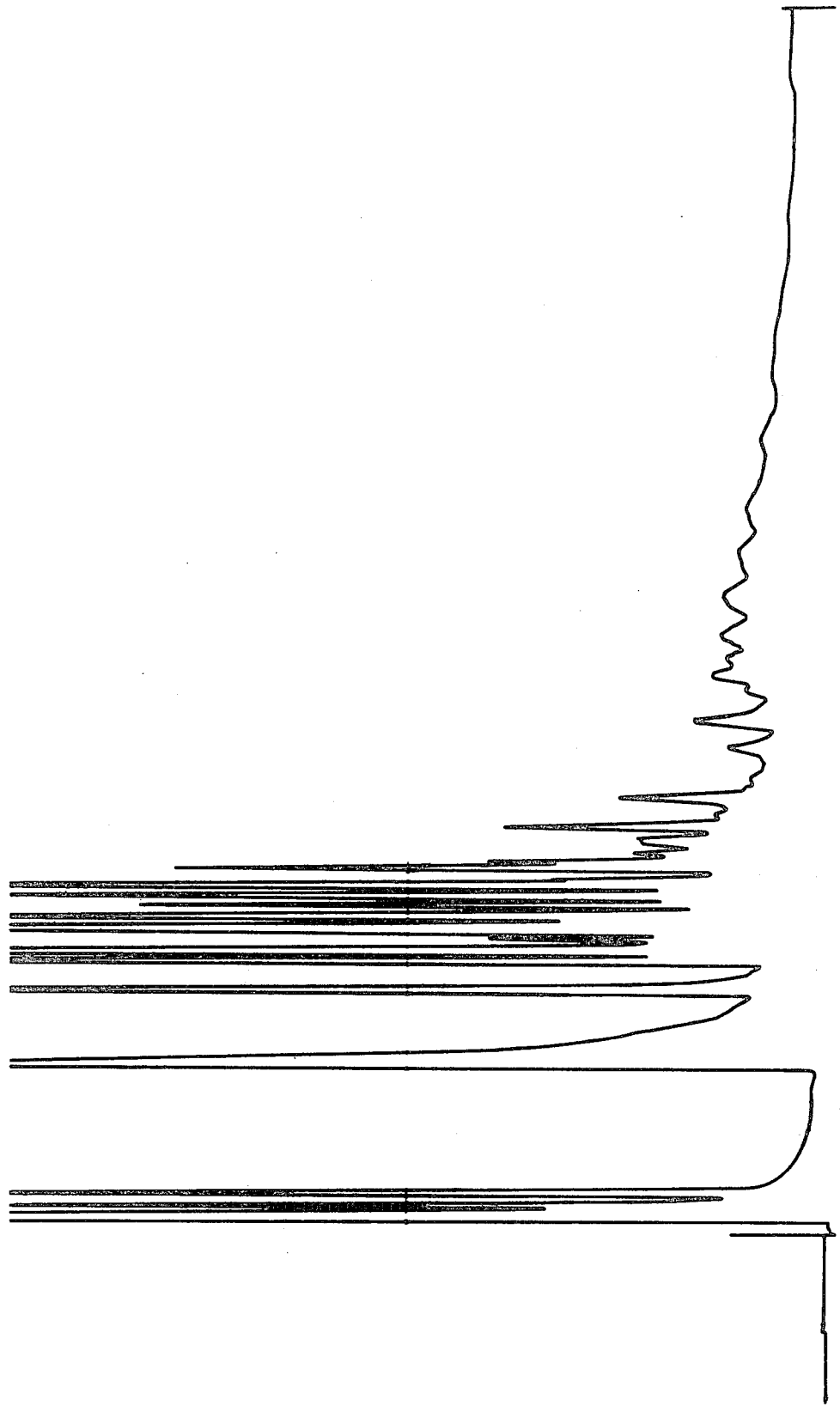
Figure 17:
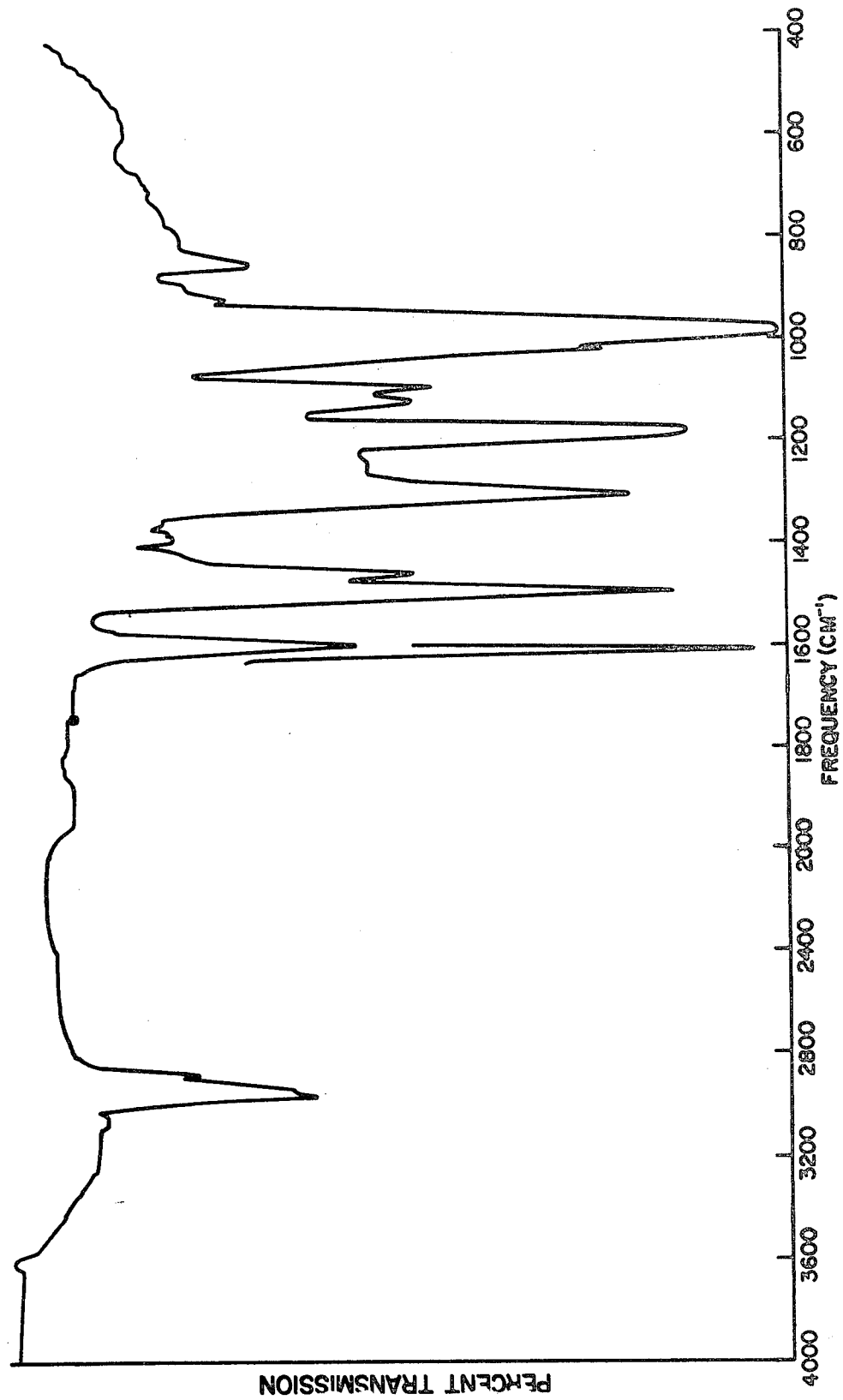

FIGS. 11–16 are GC chromatograms of various MAC-ylation products of the Examples, as indicated on the Figs. FIG. 10 is a GC chromatogram of a product of MAC-ylation of Phenolic Mixture A with 0.94 mol of MAC per mol of phenolic compounds. FIGS. 10A and 10B are GC chromatograms of products made by gradually adding one mole of MAC to one mole of phenol (containing 2 grams of Super Filtrol per 100 grams of phenol) at about 80° C. and then heating to 140° C. and maintaining that temperature for about 2 hours; FIG. 10A shows the state of the mixture at the conclusion of the addition of the MAC while FIG. 10B shows it after the 2 hours of heating at 140° C. (The chromatograms are obtained with a conventional 8 foot column filled with acid-washed chromosorb W carrying 10% Union Carbide W 98; the sample, usually dissolved in methylene chloride, is fed to a hot injection port into a stream of helium). The chromatogram of the Example 6 MAC-ylated phenol (FIG. 11) is the simplest; in this the peaks numbered 1, 2 and 3 represent the solvent used in the GC analysis and possibly unreacted MAC; peak 4 represents phenol; peaks in the zone indicated as 5 are believed to represent monochlorobutyl (e.g. 2-chloro-1,1-dimethylethyl) phenol (or isomers thereof) and/or alkenyl phenols (or isomers thereof), while peaks in the zone indicated as 6 (or some of them) show the presence of compounds having at least two phenolic groups, e.g. of formula IV discussed above. Inspection of the other chromatograms shows similar regions, as indicated (approximately) in FIG. 12 and also in FIGS. 10A and 10B which illustrate MAC-ylation products in which the reactions to form "T" linkages have been carried out to different degrees. It will be evident that the area under the peaks in zone 5 is considerably greater in FIG. 10A (shorter reaction time) than in FIG. 10B while the area under the zone 6 peaks is much greater in FIG. 10B. In the chromatograms of FIGS. 11–16 the proportion of compounds having at least two phenolic groups (zone 6) is probably below about 30%.

Mass spectrometry on the zones 5 and 6 peak materials (obtained in MAC-ylation runs other than those specifically illustrated here) indicates that when one starts with phenol, per se, zone 5 includes peaks for materials of molecular weights of 148 and 184 and zone 6 includes peaks for materials of, inter alia, molecular weights of 240 and 296. A molecular weight of 148 corresponds to methallyl phenol or isomer thereof (Formula III, above). A molecular weight of 184 corresponds to chlorobutyl phenol or isomer thereof (Formula II above). A molecular weight of 240 corresponds to a compound of Formula IV above in which "s", "w", and "n" are all zero. A molecular weight of 296 corresponds to a compound of Formula IV above in which "s" and "n" are zero, "w" is 1 and "Q" is an alkyl group (such as —CH═C(CH$_3$)$_2$).

The MAC-ylation reaction may, if desired, be carried out to such an extent that the Cl content of the mixture is well below 1%, e.g. 0.7% (in Example 6A), 0.4%, 0.2%, or even substantially zero. 1% Cl is equivalent to the amount of Cl which would be present if the content of chlorobutyl compounds of molecular weight 184 is about 5%; of course, if chlorobutyl compounds of higher molecular weight are present (such as those of formula IV) a 1% Cl content represents a still higher content of chlorobutyl compounds.

Figure 18:
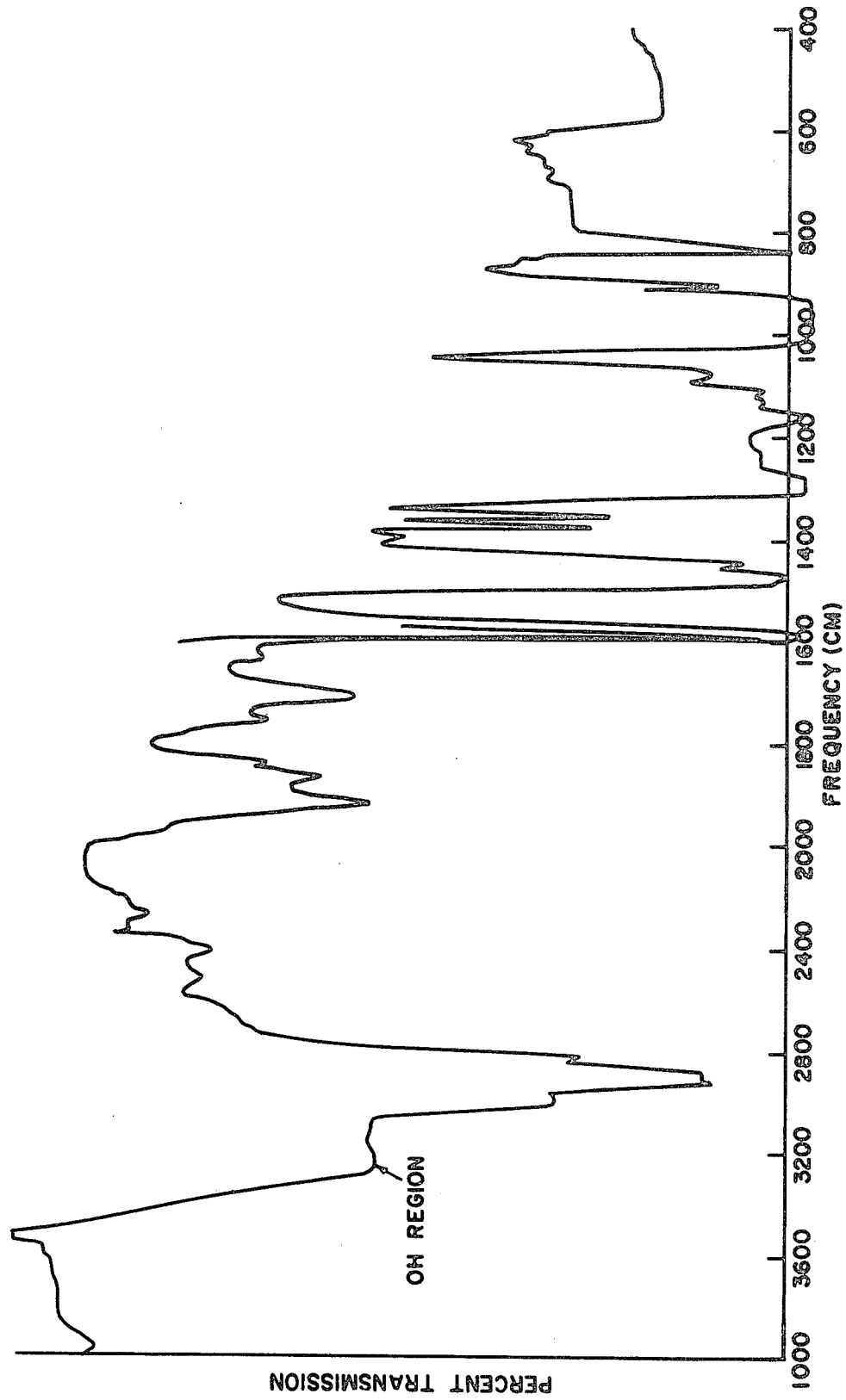
Figure 19:
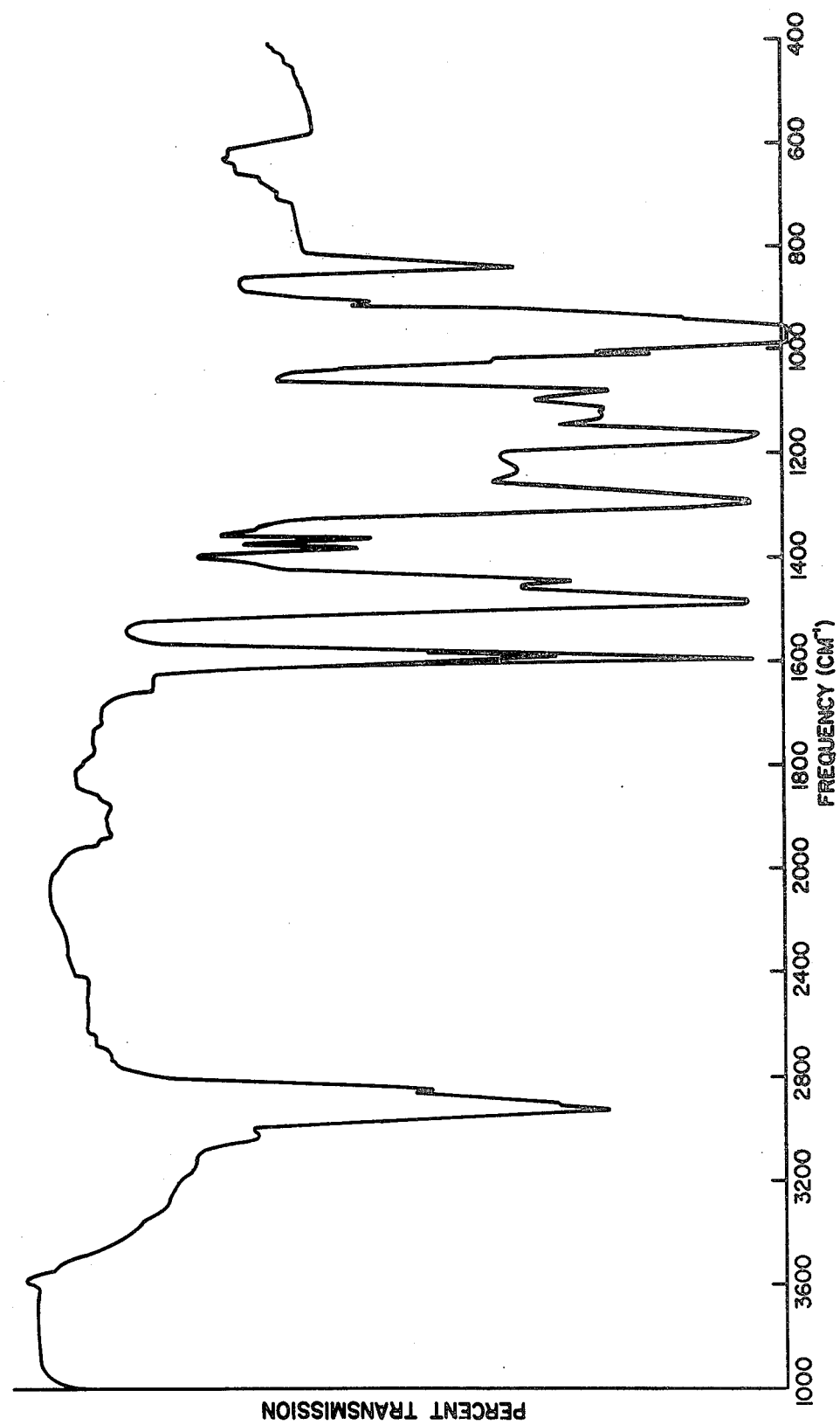
Figure 20:
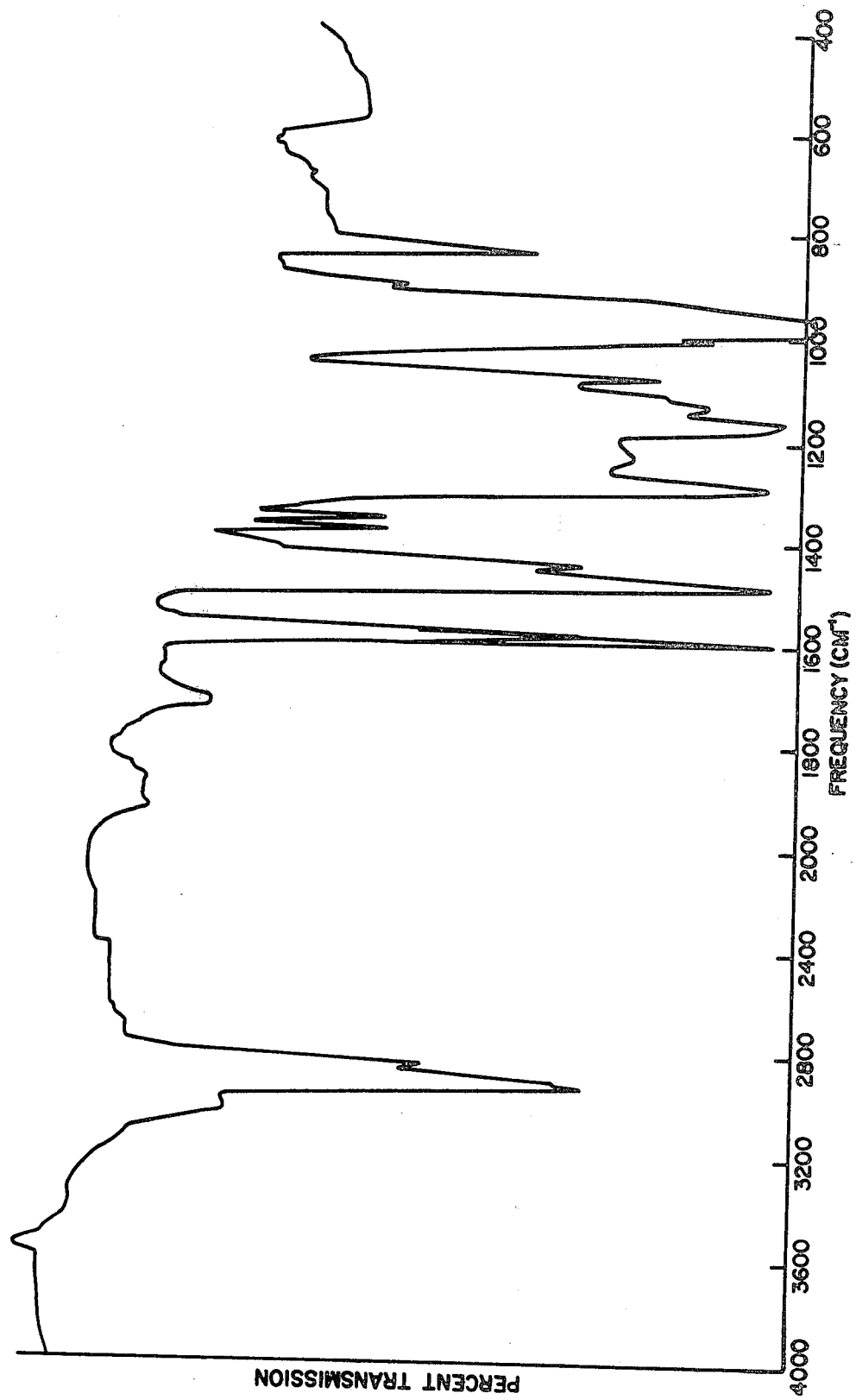
Figure 21:
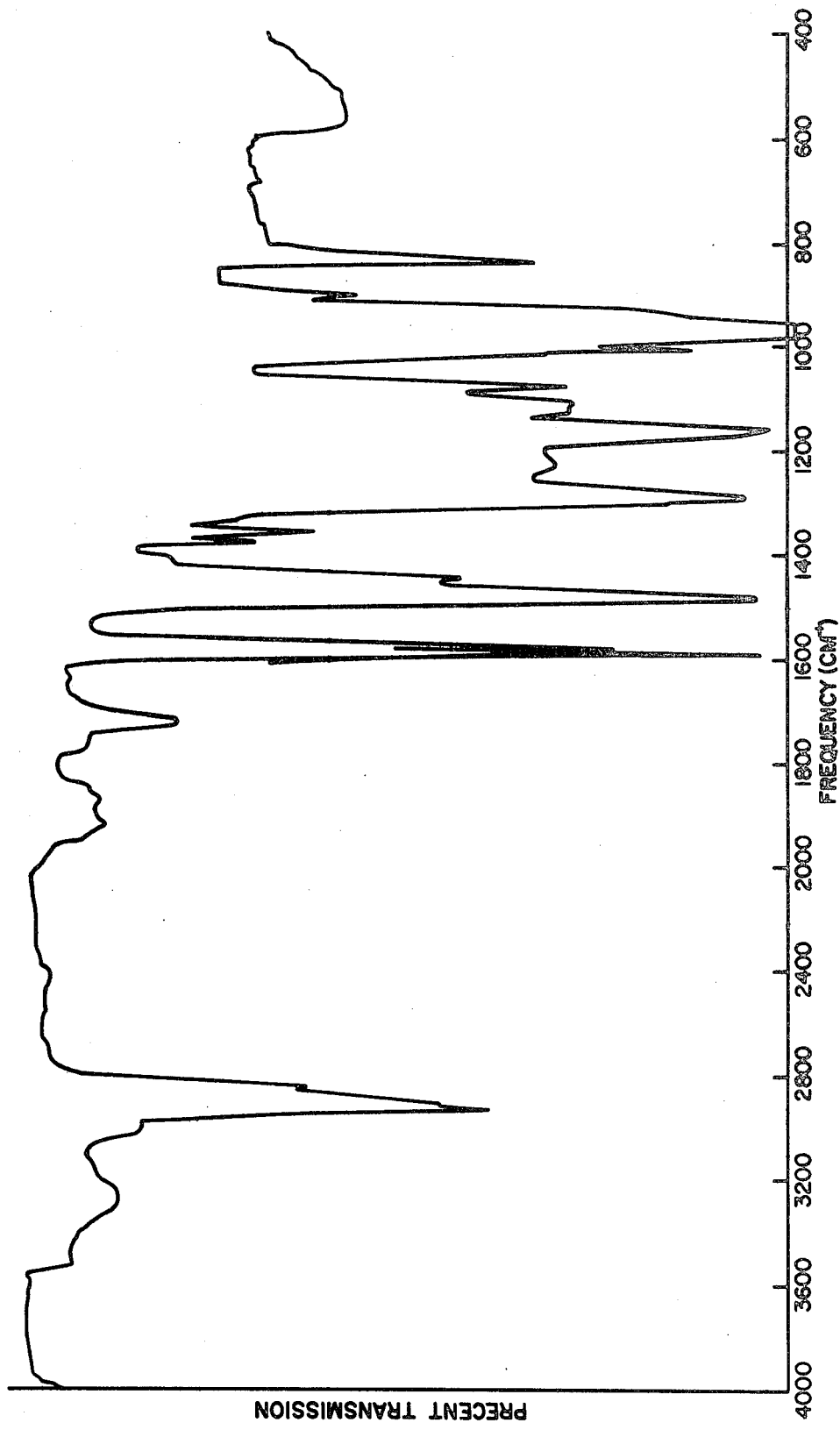
Figure 22:
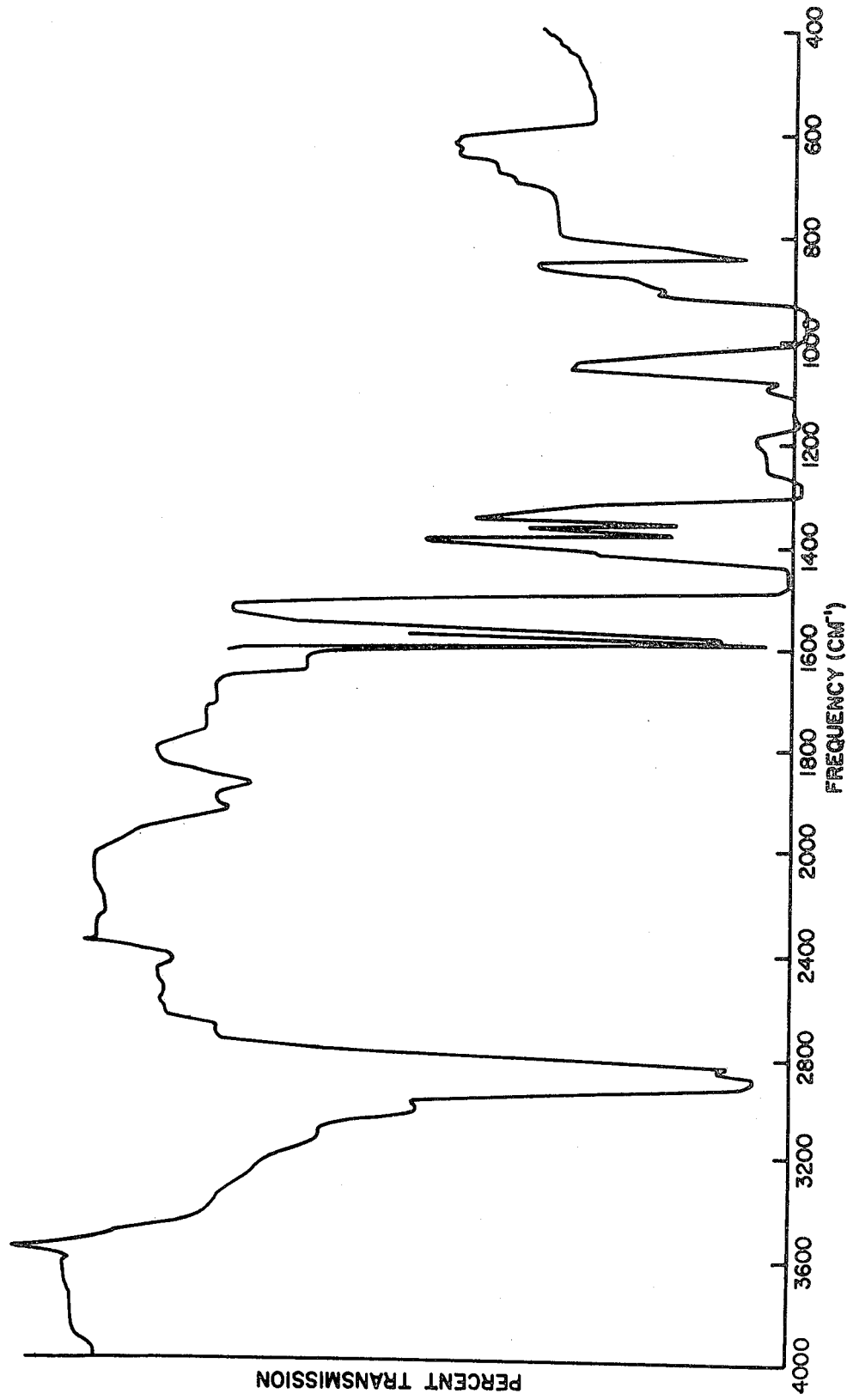
Figure 23:
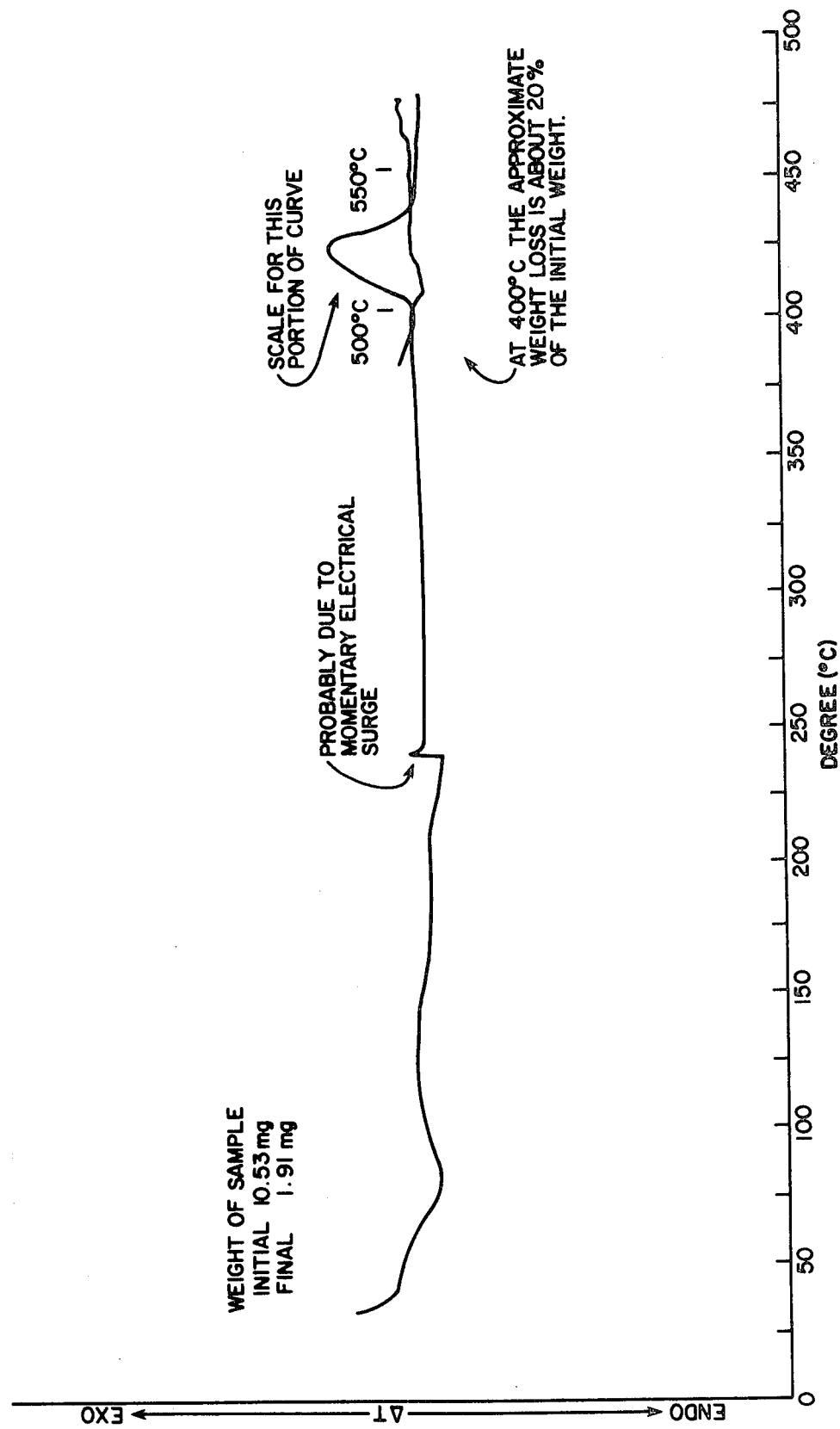
Figure 24:
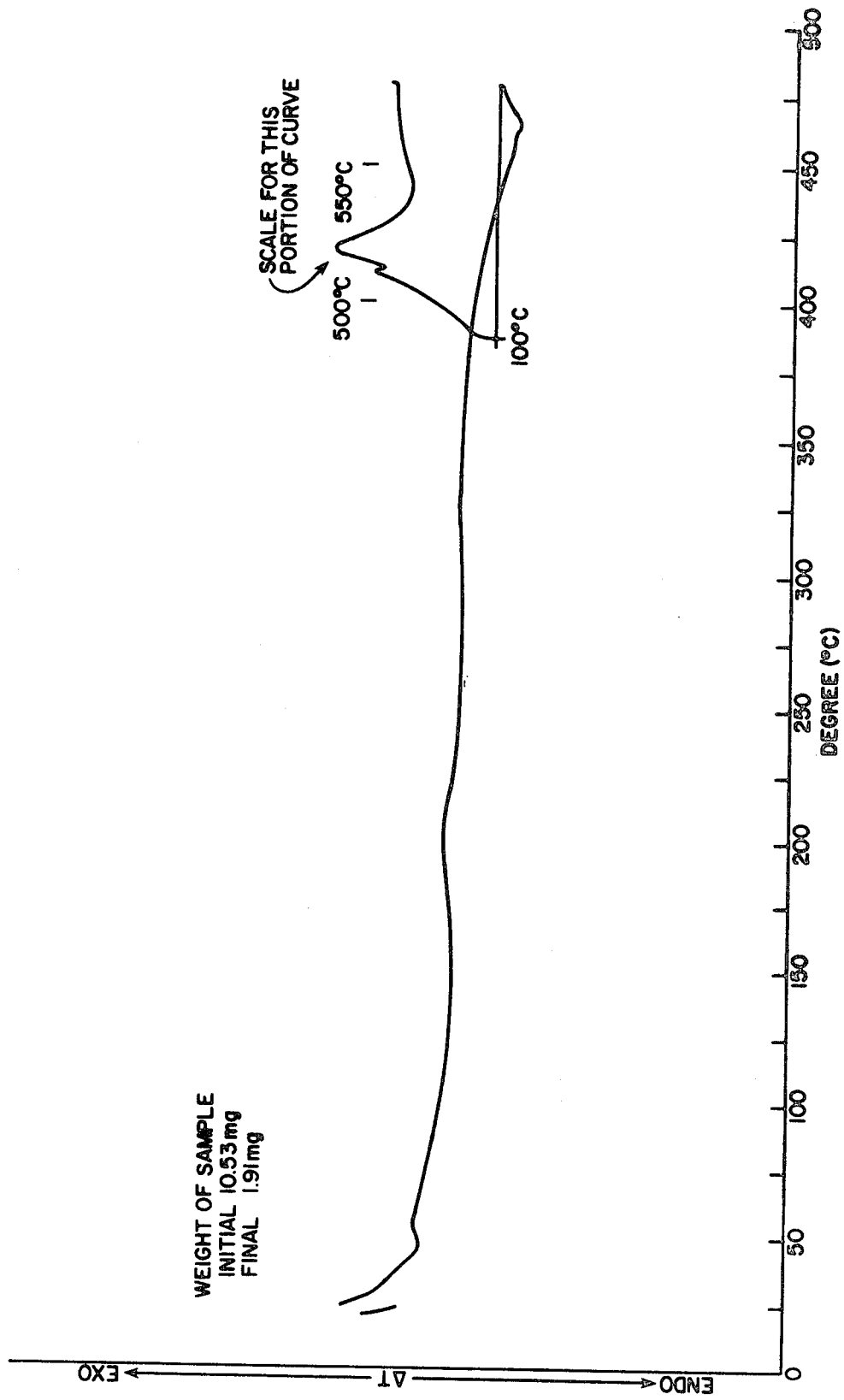
Figure 25:
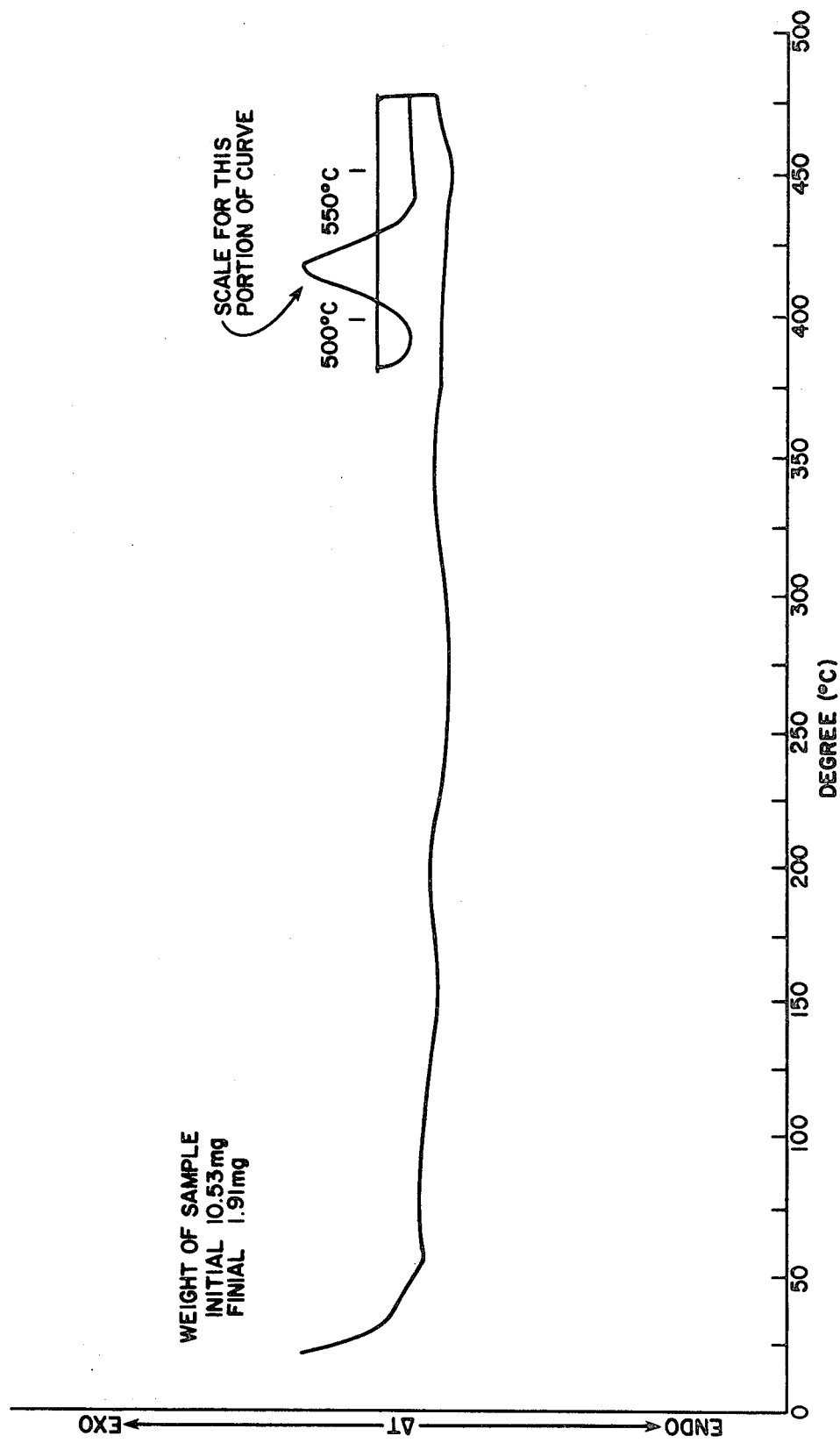
Figure 26:
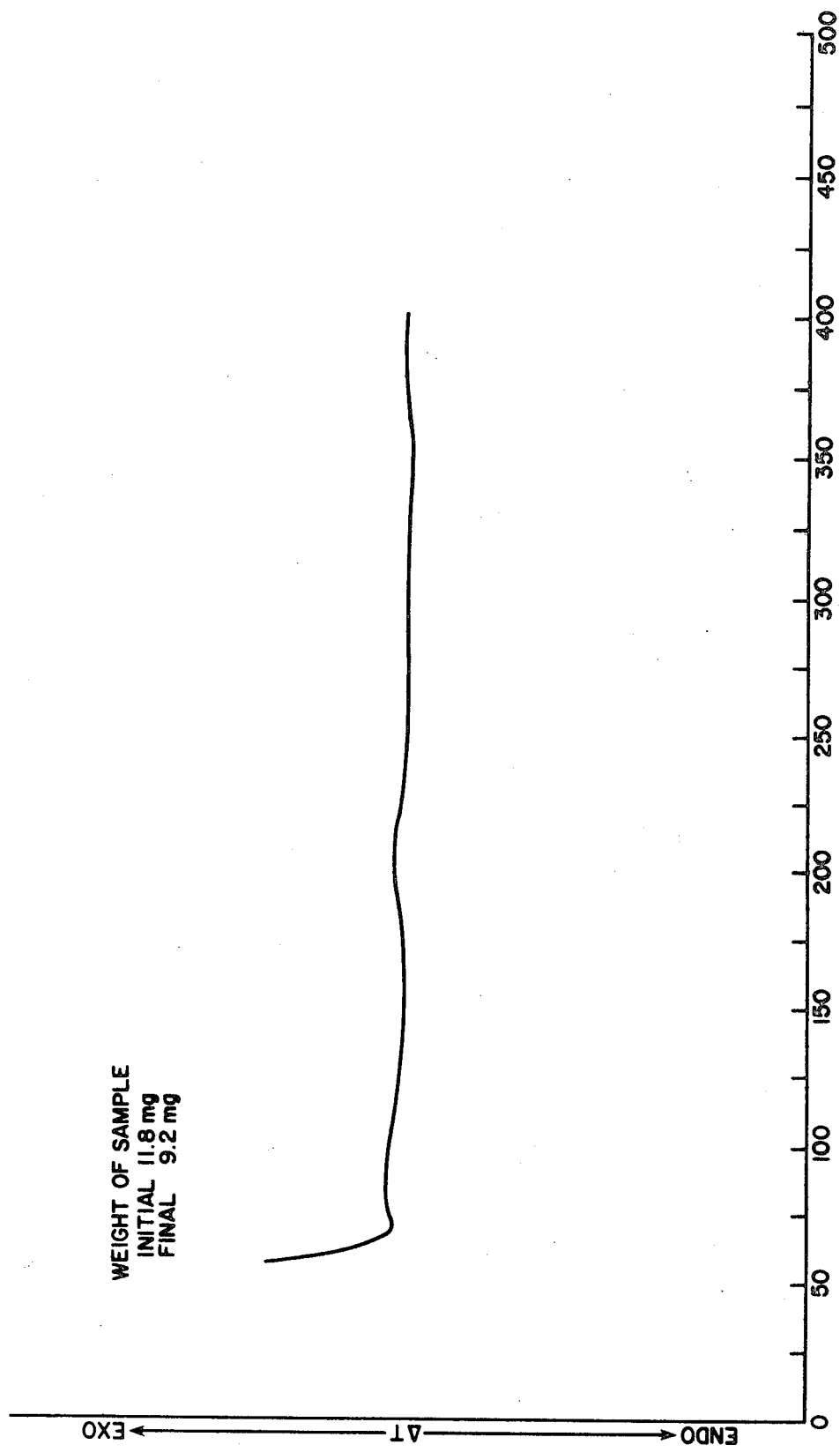

FIGS. 17–20 are infrared spectrograms of the final products of various Examples, as indicated on the Figs. All the products (except FIG. 17) show the presence of hydroxyl functions (phenolic groups) as noted on FIG. 18, for instance.

FIGS. 23-26 are thermograms obtained by heating the products of various Examples (identified on the Figs.) in a differential scanning calorimeter (DuPont 900 Differential Thermal Analyzer) under a continuous stream of nitrogen at a rate of 20° C./min. The thermograms (obtained with the instrument set at its maximum sensitivity) show no substantial exotherm or endotherm until the temperature is well above 300° C.; specifically the first significant change is a mild exotherm beginning at about 500° C. The residue after the test (in which the temperature rises to about 575° C.) is a black froth indicating gas bubbles were evolved at a stage when the material had a high enough viscosity to trap them. In another run of the same test, but stopping at 400° C., it is found that the product of Example 1 retains well over 75% of its initial weight.

The products, which are polymeric phosphates (usually oligomeric), are particularly suitable as flame retardants in polyphenyl ether plastics. For instance, they may be incorporated into blends of a polyphenyl ether and a styrene resin (such as the polymer blends described in U.S. Pat. Nos. 3,383,435 3,639,503, Japan Kokai 77,109,552 [Chem. Abstracts 88, 747142, (1978)], Ger. Offen. 2,705,656 [Chemical Abstracts 88, 38351V (1978)], and Japan. Kokai 77,98,797 [Chemical Abstracts 88, 74876d (1978)]) whose entire disclosures are incorporated herein by reference, including blends in which the ratio of polyphenylene oxide to styrene polymer is 10,90, 20/80, 30/70, 40/60, 50/50, 60/40, or 70/30 for instance). The proportion of the polymeric phosphate may be varied e.g. in the range of about 1 or 2 to 20% of the plastic, more usually in the range of about 5 to 15%, such as about 6, 8, 10 or 12%. The polymeric phosphate may be added in any suitable manner, such as that described in U.S. Pat. Nos. 3,383,435 and 3,639,506 which mention blending the finely divided powdered solid components and then extruding the blend at relatively high temperature such as about 450°-640° F. (230°-340° C.). The polymeric phosphates described herein are quite stable at those temperatures. Unlike the phosphates described in U.S. Pat. No. 2,639,506 they do not tend to volatilize or exude either in the blending or the subsequent hot molding of the mixture even though they act as extrusion promoters, giving increased throughput and they have only a relatively small effect, or practically none (as with the product of Example 7), on the heat distortion temperatures or Tg of the plastic; thus when used in the preferred amounts, they have little or no plasticizing effect at use temperatures (although they may plasticize at processing temperatures. For instance, a blend of high impact styrene and polyphenylene oxide which has a Tg of 130° C. shows a Tg of about 105° C. when blended with 10 phr of Triaryl Phosphate I (described below), but the Tg is about 122° C. when the same plastic is blended instead with 10 phr of the product of a repetition of Example 1 and it is even higher when blended instead with 10 phr of the product of Example 7. It is, however, within the broader scope of the invention to use the polymeric phosphates in larger amounts, to serve as flame-retardant plasticizers, e.g. in proportions such as 40, 60, or even 100% or more based on the weight of the high polymer.

When the polymeric phosphate is in the form of a powdered solid, pre-blending with the plastic is quite simple. When it is a gum, blending may be conveniently effected while heating. For example, the plastic may be milled on hot rolls and the millable gum may be added, thereto while continuing the milling; or the gum may be melted and poured onto the powdered plastic at an elevated temperature, or onto the plastic being milled. The gum may also be converted to powdered form by grinding at a low-temperature at which the gum is friable and (before, during or after grinding) blending it with a material which prevents the resulting powdered particles from caking together unduly (such as finely powdered conventional flow aids like clay, calcium carbonate, calcium silicate, magnesium silicate, pyrogenic silica (e.g. Cabosil), or carbon black, or even a fine powder of one or more of the high polymeric components of the plastic (e.g. fine polyphenylene oxide powder); the amount needed for this purpose may be determined by simple trial-and-error with each particular gum. Also it is within the scope of the invention to blend a small proportion of particles of a high polymer (such as polystyrene) into the molten gum to preferentially absorb lower molecular weight components of the gum and thereby decrease the tendency of the powder particles to flow together. The gums may also be dispersed in a volatile liquid (e.g., as a solution or emulsion) which may be applied to the finely divided plastic material followed by evaporation of the volatile liquid.

It has also been found that the gums may be converted to the more desirable products (which can be ground at room temperature to form powders that remain free flowing on standing) by simply remelting the gum and continuing the vacuum distillation at high temperature (e.g., at 0.1 mm Hg at 250° C.) to distill off the lower, molecular weight materials which may be present, and possibly effect further phosphorylation. Under distillation conditions where the pot residue is a solid at room temperature the molecular weights of the species which distill off are generally below about 600; thus aryl phosphates having as few as two phosphate moieties (as when "t" is the number one in formula VI above) are retained but those having only one phosphate moiety are preferably removed to such a degree that the product is a friable solid. Conversion of the gum to the more desirable powderable material has occurred on such distillation of even less than 5% of the gum (see Example 6).

The material distilled off during or after the reactions may be re-used. For example, distilled compounds of formulas I, II, III or IV may be mixed with the fresh phenolic feed before MAC-ylation or may be mixed with the MAC-ylation product before or during phosphorylation. Triaryl phosphates distilled off during the process (these being mainly triphenyl phosphates in Examples 6 and 7 and mixed isopropylphenyl phenyl phosphates in Examples 1–5) may be used for conventional purposes, e.g. as flame retardants for various plastics.

Other plastic into which the polymeric phosphates may be incorporated as flame retarding agents include the well known engineering thermoplastics which are processed at relatively high temperatures (e.g., above about 150° C.) such as nylons (e.g., nylon 6), aromatic polyesters (e.g., polyethylene terephthalate or polybutylene terephthalate), polycarbonates (such as the polycarbonate of bis-phenol-A), polyphenylsulfone and polyether sulfone plastics, as well as thermoplastic polymers which process at lower temperatures such as polystyrene, polyethylene, (e.g., of high or low density types), polypropylene (e.g. isotactic polypropylene), polyacrylics (e.g., methyl methacrylate polymer) or ABS resins. They may be employed in conventional polyurethane foams, being added, for instance, to the reactants (e.g. di- or poly- isocyanate and polyol) prior to the final reaction and products containing free phenolic groups (as discussed herein) may participate in the reaction with the isocyanate groups. Any of the plastics described in German published application U.S. Pat. No. 2,708,447 may be employed.

The polymeric phosphate may be the sole flame retardant additives or other additives may be present for this purpose, such as chlorine or bromine compounds (e.g., of the type and in the proportions described in U.S. Pat. No. 2,639,506). Typical materials are octobromo bis phenyl ether, hexabromododecatriene and the brominated material sold as Firemaster 680. For instance ABS resin to which 16 phr of the product of a repetition of Example 1 and 25 phr of Firemaster 680 has been added burns only some 2 or 3 seconds in a UL94 test. Flame retarding additives such as any of the aromatic or heterocyclic compounds having anionic cleavable groups described in German published application No. 2,708,447 (published Sept. 8, 1977) which may interact synergistically with phosphorus compounds may be included in the amounts described in that German application. Other flame retarding additives that may be blended into the plastic together with the phosphorus compounds described herein are nitrogen compounds such as phosphorylamides or N,N-diallyl diphenyl phosphoramidate or guanylurea phosphate, boron compounds, (e.g. Borax) compounds which form free radicals on heating in the flame such as cyclophones, (e.g. such as those described in U.S. Pat. No. 3,660,346), oligomers obtained by dehydrogenating diisopropylbenzene (e.g. such as those described in U.S. Pat. Nos. 3,943,195 and 3,441,524), peroxides (e.g. such as those described in U.S. Pat. Nos. 3,637,578, 3,936,414, 3,559,045 and 3,684,616), azo compounds (e.g. azotibisobutyronitrile), or small amounts of acid salts that may act to cleave phosphate linkages (such as salts described in U.S. Pat. Nos. 4,066,618, 4,067,846 or 4,069,201 or German published application No. 2,647,271), e.g. in the proportions described therein.

The plastics may, of course, contain other additives such as fillers, e.g., chopped glass fibers, carbon black, other pigments, etc. Also they may contain monomeric phosphates, such as those listed in U.S. Pat. No. 3,639,506.

In making the polymeric phosphate, the starting phenol which is reacted with the MAC may be phenol, isopropyl phenols, cresols, ethylphenols, sec-butyl and-/or t-butyl phenols, higher alkylated phenols, chloro- or bromoalkyl phenols, ring-halogenated phenols such as 2-chlorophenol, or a polyhydric phenol, such as bisphenol A or resorcinol or hydroquinone. One phenol may be reacted with MAC, then the same or a different phenol may be blended with the MAC-ylation product and one of these or still another phenol may be used to react with excess >P[O]Cl groups. Phosphorylation may be effected in stages; for instance, the MAC-ylation product may be reacted with a preformed phosphorochloridate such as ArOP[O]Cl$_2$ or (ArO)$_2$P[O]Cl, or mixtures thereof, where "Ar" is aromatic such as phenyl. Mixed alkyl aryl polymeric esters may be formed (in which there is an aliphatic group [such as methyl, ethyl, propyl, isopropyl, t-butyl, sec-butyl], or substituted alkyl, [e.g., chlorobutyl] in place of one or more of the (terminal) phenyl or isopropyl phenyl groups of the polymeric ester; for this purpose the MAC-ylation product may be reacted to convert it to its phenoxide form (e.g., by conventional reaction with a base such as NaOH), which is then reacted with a phosphochloridate having such an aliphatic group, e.g., a phosphochloridate of the formula (R'O)P[O]Cl$_2$ or (R'O)$_2$P[O]Cl or a mixture of these, where R' is the aliphatic group. The aliphatic group need not be monofunctional; e.g., the phosphochloridate may be the formula

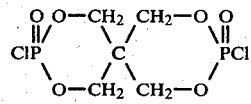

The MAC-ylation product may be employed to form a flame retarding phosphorus compound having only one or two ester oxygens on the phosphorus (such as a phosphonate). To this end it may be reacted (as such or after conversion to its phenoxide form as indicated above) with such compounds as ArP[O]Cl$_2$, Ar$_2$P[O]Cl, (ArO) ArP[O]Cl, RP[O]Cl$_2$, ArRP[O]Cl, R$_2$P[O]Cl, (ArO)RP[O]Cl, (RO)RP[O]Cl, (RO)ArP[O]Cl, etc. or mixtures of such compounds.

The MAC-ylation products may be employed to form phosphites (instead of phosphates) by reaction with PCl$_3$ (instead of POCl$_3$). These may be employed as antioxidants, for instance.

In place of MAC, other alkenyl halides may be used for the alkylation such as methallyl bromide; allyl chloride; allyl bromide; 1,4-dibromo-2-butene; crotyl chloride; isocrotyl chloride; 2,3-dimethyl-2 chloro-2-butene; vinyl chloride; 1-phenyl-3-chloropropene. In the discussion of the foregoing Examples it was pointed out that both the olefinic and the chloro groups of MAC served as alkylating groups in the reaction. It is therefore within the scope of the invention to employ other compounds having two (or more) such alkylating groups such as diolefinic compounds or dihalo compounds in place of, or in admixture with, the MAC. The alkylating groups may also be alcohol or ether groups (as in, for example, methallyl alcohol or related alcohols such as

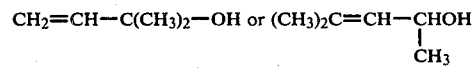

or ethers thereof such as methallyl ethyl ether, dimethalyll ether, or diallyl ether.

There are indications that part of the superior flame retardant properties of the products of the foregoing Examples are attributable to the presence of the T$_1$ linkage, which may break up in the flame to produce relatively stable benzylic free radicals such as radicals having the group

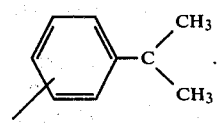

as well as benzylic free radicals having the group

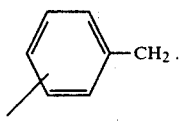

and thus more volatile phosphate ester moieties. It is therefore presently believed preferable to employ as the alkylating agent a compound which (like MAC) produces two-carbon aliphatic bridges between aromatic rings (i.e. bi-benzylic linkages

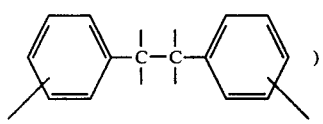

and to employ reaction conditions to promote the formation of such linkages in the initial (alkylation) reaction; in one preferred case, in which T linkage formation is not completed until the phosphorylation reaction occurs, it is preferred to also employ conditions promoting formation of such bi-benzylic linkages in the phosphorylation stage.

In the products of Examples 1–7 above, the data indicate that there are present both the bi-benzylic linkages and other, more stable, types of linkages which yield less stable free radicals which are formed at higher temperatures. This may be advantageous in giving a gradual or stepwise linkage breakage as the temperature increases in the material being subjected to the flame, so that all the material is not volatilized or decomposed at a particular instant or at a particular temperature.

Another aspect of the invention involves reacting a phosphorylating agent such as $POCl_3$ with (a) a phenol or an alkylphenol or mixture thereof (such as isopropylated phenols made by reacting propylene with an excess of phenol) and (b) a preformed pure or crude phenolic material having a alkylating group such as a chloralkyl phenol or an alkenyl phenol made in any manner, the phosphorylation being effected under conditions to cause alkylation thereby forming carbon chain linkages between aromatic rings.

In the MAC-ylation reaction, conventional Friedel-Crafts alkylation catalysts may be used, preferably at elevated temperature. Thus in the Examples a well known clay alkylation catalyst (Superfiltrol) and aluminum chloride are employed; the aluminum chloride is also a known phosphorylation catalyst. Various Friedel-Crafts catalysts are disclosed, for instance, in Chapter 4 of the book Friedel-Crafts Chemistry by George A. Olah (pub. 1973 by John Wiley and Sons); Friedel-Crafts catalyst include such materials as sulfonic type cation-exchange resins; synthetic hectorites containing metal atoms such as beryllium, aluminum, magnesium or indium; molybdenum hexacarbonate, etc. MAC-ylation may be effected by heating in the absence of added catalyst, e.g. in a run involving addition of about 0.34 mol of MAC to 1 mol of phenol at about 80° C. followed by heating at 130° C. for 15 hours, formation of species showing GC peaks in zones 5 and 6 (see FIG. 11) has been noted, even though very little HCl is evolved in the reaction.

The phosphorylation may be effected in conventional manner, e.g., well known phosphorylation catalysts such as aluminum chloride, titanium chloride or magnesium chloride may be used in conventional amounts in reactions with $POCl_3$ or phosphochloridates. Phosphorylation may also be effected by converting the phenolic MAC-ylation product wholly or partly to the corresponding alkali metal phenoxide (e.g. by reaction with NaOH) before reaction with the phosphorylating agent.

The proportions and conditions may be varied widely. In the phosphorylation reaction with $POCl_3$ it is presently preferred to employ about 2 to 3 moles (based on phenolic content) of the MAC-ylation product per mole of $POCl_3$ and to heat the mixture up to about 200° to 250° C., in the presence of an amount of $AlCl_3$ catalyst in the range of about $\frac{1}{4}$ to $2\frac{1}{2}$%, the time at about the maximum temperature being about 2 to 8 hours.

The products may have unreacted

groups; this may explain the odor of HCl which is sometimes observed when closed jars containing such products are opened after a few days storage at room temperature. This may be decreased or eliminated by the inclusion of a chlorine-free monohydric phenol (such as phenol or isopropyl phenol) in the mixture in amount such as to provide a stoichiometric excess of phenolic material (e.g., a 5 or 10% excess) to drive the reaction towards completion prior to the final high temperature vacuum distillation.

The MAC-ylation products (or related alkylation products discussed above) may be employed for making esters of other acids, for instance carbonates (made by reaction with phosgene) carboxylic acids (including di- and tricarboxylic acids, e.g. phthalic esters made by reaction with phthalic anhydride or chloride or the acid itself, or by transesterification). For such purposes one may use the whole mixed MAC-ylation product or individual components thereof.

In another type of polymeric phosphate, illustrated in Examples 8–15 below, the starting material may comprise isopropylphenyl phosphate (preferably a triaryl phosphate having isopropylphenyl groups, e.g., with an isopropyl in a meta or para position). The isopropyl groups are converted to isopropenyl groups which are then reacted to cause coupling of two or more aryl phosphate molecules. In a more preferred embodiment of this type the isopropenyl groups are generated by halogenation of the isopropyl group followed by dehalogenation and the coupling is effected by oligomerization through the double bond. In one form, illustrated in Examples 10 and 11, the oligomerization is effected by heating in the presence of powdered metallic zinc with the result, it is believed, that the product has aromatic rings linked together by aliphatic chains as indicated schematically below:

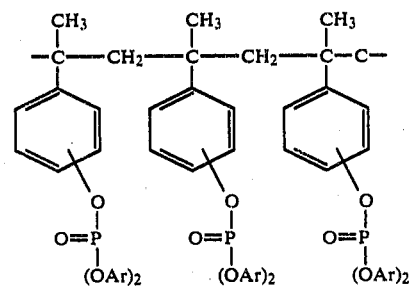

(A)

and/or

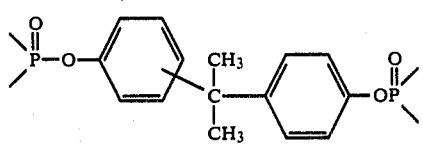

(B)

In formula A above the product has aromatic rings linked together by aliphatic chains comprising at least two aliphatic chain carbon atoms between rings; several triaryl phosphate molecules may be joined together as pendent groups on relatively short aliphatic chains. In formula B there are aromatic rings linked together through a single carbon atom. In another, less preferred form, illustrated in Examples 8 and 9, the oligomerization is effected by heating in the presence of zinc chloride or other Friedel-Crafts alkylation catalyst to give products having, it is believed, a structure like that shown in formula B above and possibly structures, or linkages, like that shown in formula A above. When the zinc metal is added, there is an evolution of HCl, presumably derived from residual chlorine in the chlorinated phosphate material; this may indicate that the zinc is modified in some way, as by formation of zinc chloride in situ, probably gradually during the oligomerization reaction.

The halogenation of the isopropyl phenyl phosphate is preferably carried out under such conditions that there is substantially no chlorination of the aromatic ring and the chlorinated product has more than 70% (e.g. 80% or more) of its chlorine in the form of

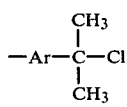

groups and a minor portion in the form of dichloro- amd trichloro-propyl groups. This may be accomplished, for instance, by chlorinating in chlorobenzene solvent at, say, room temperature under ultraviolet light; under these conditions the meta and para isopropyl groups are preferentially chlorinated. Similar chlorination in methylene chloride yields more dichloro- and trichloro-propyl groups. Dehydrohalogenation to form isopropenyl groups may be effected by simple heating (e.g., at over 100° C.) or heating in the presence of an HCl acceptor. The number of linkages between triaryl phosphate molecules depends in large part on the number of isopropenyl groups; for instance, in experiments made thus far (using phosphate mixture VI), the continued heating in the presence of zinc chloride has resulted in the formation of products insoluble in methylene chloride when the chlorination uses more than about 0.7 equivalents of $Cl_2$ per isopropyl group, and soluble products when lesser amounts of chlorine are employed. The reaction may be effected in such fashion that monomeric triaryl phosphate remains in the reaction mixture and acts as a solvent or plasticizer for the oligomeric material being formed; the monomeric material may then be distilled off at high temperature (above the melting temperature of the residue) under relatively high vacuum, as illustrated in Examples 10 and 11.

In the Examples below the starting triaryl phosphates are made from isopropylated phenols (made by reacting various proportions of propylene with phenol in the manner described in Example 1, above). For instance triaryl phosphates having the compositions set forth in the tabulation below may be used. In that tabulation the numbers are approximate percentages by weight obtained by fractionation (usually by gas liquid phase chromatography, as described generally above) the fractions being arranged in their order of elution from the chromatographic column.

| Fraction* | Triaryl Phosphate | | | | | | |
|---|---|---|---|---|---|---|---|
|  | I | II | III | IV | V | VI | VII |
| Triphenyl phosphate | 27.6 | 34.7 | 19.6 | 12.8 | 6.8 | 1.4 | 3.7 |
| Cresyl Diphenyl phosphate |  |  | .2 |  | .4 |  | 3 |
| 2-isopropylphenyl diphenyl phosphate | 20.9 | 3.0 | 16.7 | 2.7 | 9.6 | 2.2 | 7.1 |
| 3-isopropylphenyl diphenyl phosphate | 2.9 | 17.9 | 3.3 | 17.6 | 2.4 | 5.3 | 1.8 |
| 4-isopropylphenyl diphenyl phosphate | 14.0 | 15.1 | 14.9 | 10.9 | 10.6 | <5 | 7.2 |
| Di(2-isopropylphenyl) phenyl phosphate | 9.0 |  | 7.9 | .2 | 6.7 | >1 | 6.9 |
| Two | 4.5 | 3.0 | 5.2 | 5.4 | 5.6 | 7.4 | 4.7 |
| Two and Three** | 9.1 | 5.2 | 12.3 | 10.7 | 19.1 | 9.2 | 19.4 |
| Two and Three | 3.7 | 7.1 | 5.6 | 12.3 | 8.4 | 13.0 | 7.9 |
| Two, Three and Four | 3.4 | 4.4 | 5.5 | 7.6 | 8.8 | 13.4 | 8.7 |
| Three and Four | 2.4 | 2.5 | 4.4 | 5.3 | 11.3 | 12.3 | 15.7 |
| Three, Four and Five | 1.0 | 2.7 | 2.2 | 5.9 | 3.9 | 11.0 | 4.9 |
| Three, Four and Five |  | 2.7 | 1.4 | 5.0 | 2.8 | 10.4 | 4.0 |
| Three, Four and Five |  | 1.0 | .9 | 2.7 | 2.6 | 7.6 | 4.3 |

*Isomeric fractions containing triaryl phosphates having the number of isopropyl groups per phosphate molecule indicated above.
**Note: "Two and Three" indicates that the particular isomeric fraction contains triaryl phosphate molecules having two isopropyl groups per molecule plus triaryl phosphate molecules having three isopropyl groups per molecule. Mixtures II, IV and VI are made by isomerizing mixtures like I, III and V as described, for instance, in U.S. Pat. 3,859,395.

EXAMPLE 8

Figure 27:
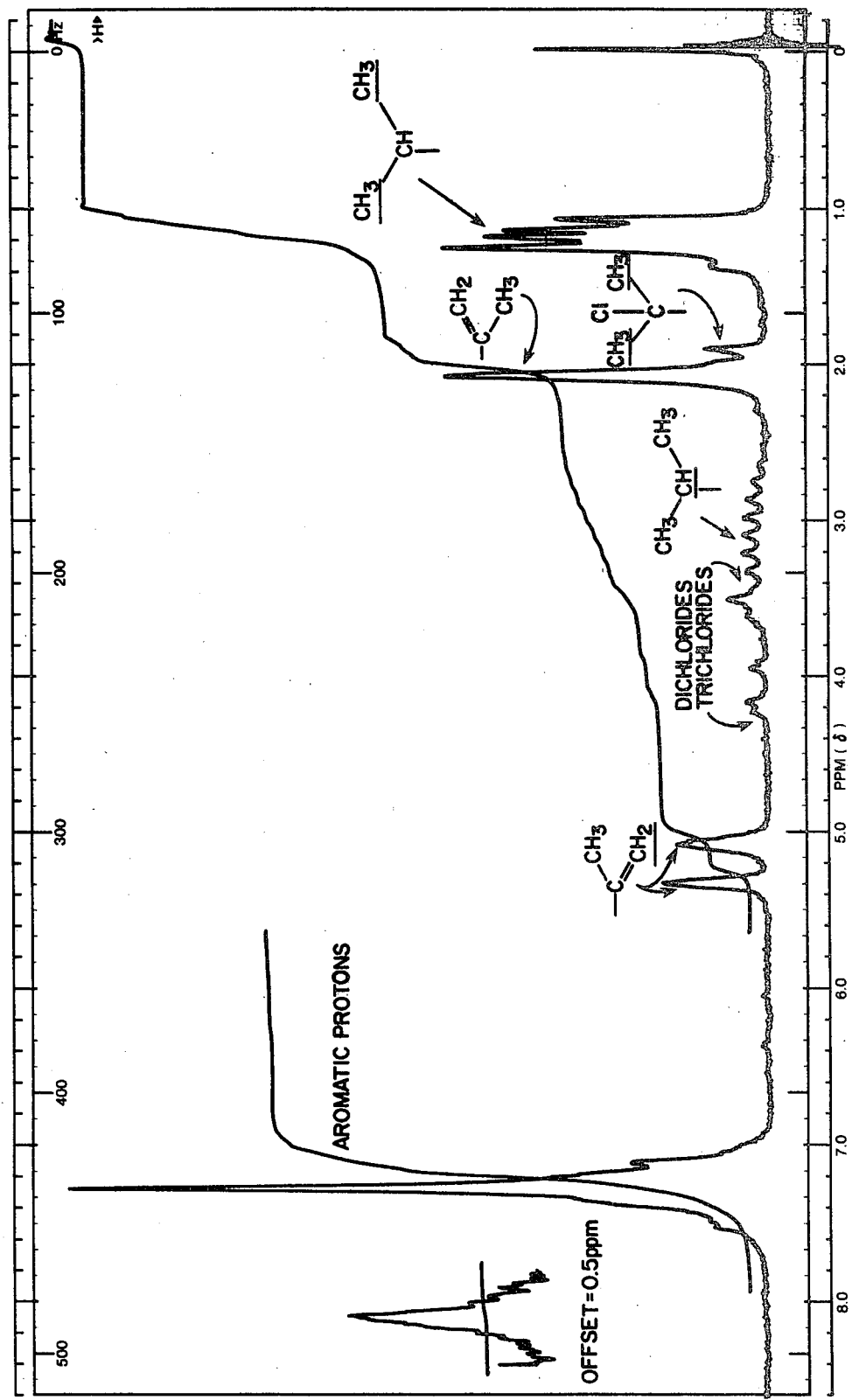
Figure 28:
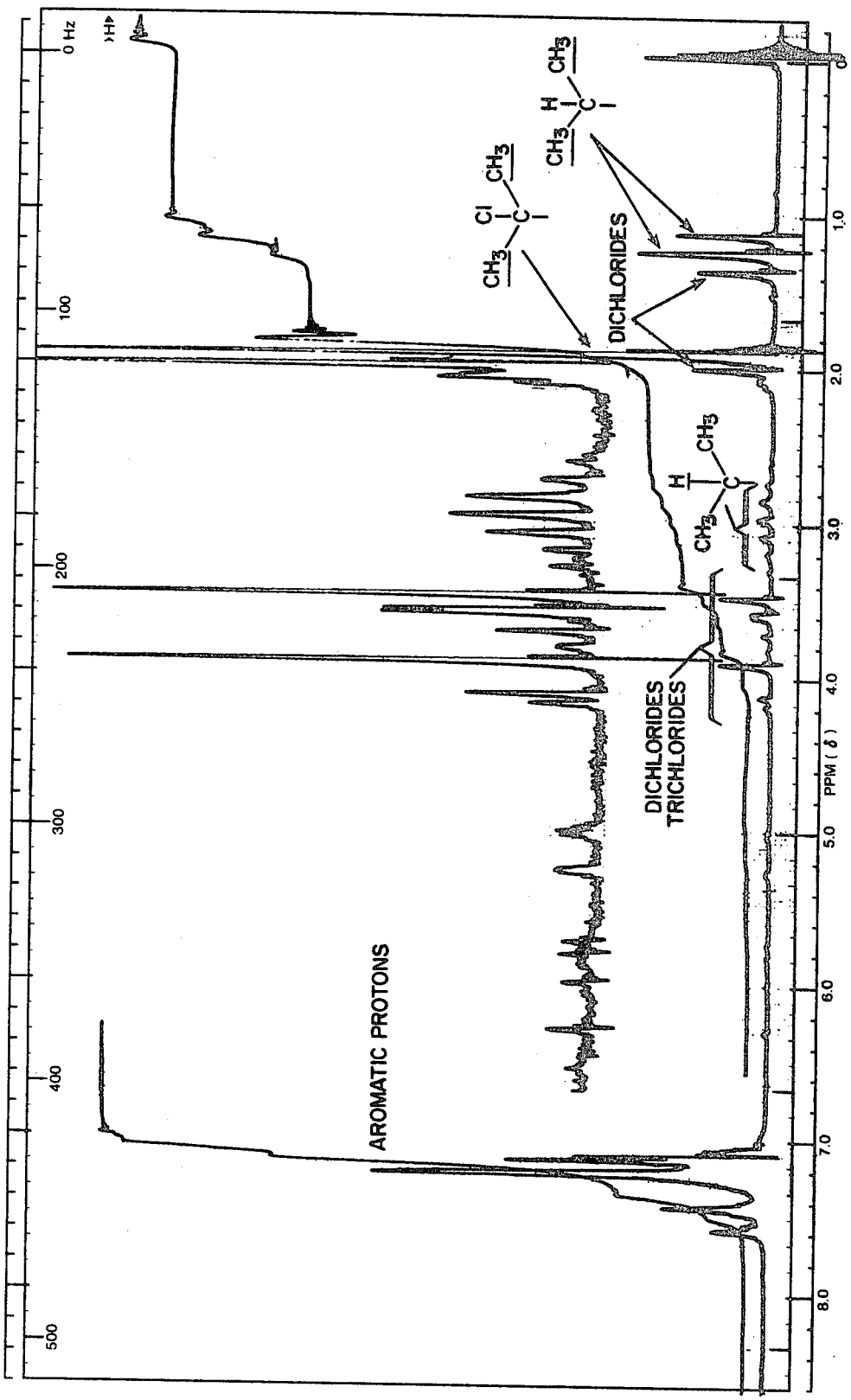

A solution of 194.9 g (0.437 mol) of Triaryl Phosphate VI containing an average of 2.85 isopropyl groups per phosphorus and 800 ml of chlorobenzene is stirred in a 2 liter 3-neck flask with a magnetic stirrer and a stream of nitrogen is passed through the flask for 10 minutes. A dry ice condensor is placed on the flask, and the flask is placed in a water cooled bath with tap water flowing through the bath to maintain the reactor at room temperature. A 375 watt sunlamp is placed about 4 inches from the flask. Chlorine gas is bubbled into the reaction mixture through a pipet at a flow rate of 4.4 mmol per minute for 226 minutes (total 0.99 mol $Cl_2$ added or 0.8 equivalents $Cl_2$ per isopropyl group). (The flow of $Cl_2$ is monitored using a rotameter calibrated prior to reaction by chlorinating a 1 N solution of potassium iodide and titration of the iodine with 0.1 sodium thiosulfate.) After the addition of chlorine the material is yellowish in color; the light is left on for 15 more minutes, at which time the solution is colorless. The HCl formed during the reaction is trapped by passing the off-gas through a sodium hydroxide solution, and remaining HCl is thereafter removed by a N₂ sparge for a few hours. The chlorobenzene is then removed using a rotary evaporator under high vacuum. The sample is then placed in a 500 ml flask and heated to 100°–120° C. for 4 hours under vacuum (at an absolute pressure of 0.5–1.0 mm Hg) to remove remaining chlorobenzene. NMR analysis (FIG. 27) of the resulting slightly yellow oil indicates that most of the tertiary chloride first formed in the reaction has been converted (by splitting off of HCl) to form isopropenyl groups. The ratio of isopropenyl groups to remaining tertiary chloride to unreacted isopropyl groups is 47:4:49, as obtained by integration of signals at 1.0–1.4 ppm for isopropyl groups, signals at 1.95 ppm for tertiary chloride and signals at 2.05, 5.05 and 5.35 ppm for isopropenyl groups. Smaller signals from dichloride (i.e.

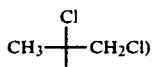

and trichlorides

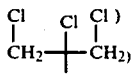

are also observed at 3.5, 4.2 and 2.05 ppm.

The mixture is then heated to 170° with 1.5 g of zinc chloride under nitrogen using a mechanical air driven stirrer for agitation. More HCl evolution is observed during this heating. After 40 hours, the sample is a gel at 170° and so viscous that the stirrer stopped. The sample is cooled to room temperature and has the appearance of rosin (and a dark red color). It is then cooled with dry ice, broken and removed from the flask. The product is then ground at room temperature in a ball mill and run through a 100 mesh screen to give a yellow powder (186 g or 95%—some handling losses were encountered, e.g. during grinding). The product may be crosslinked, as shown by the fact that it largely insoluble in CH₂Cl₂ but swells on addition of CH₂Cl₂; it is found to contain 4.47% residual chlorine and 7.1% phosphorus.

EXAMPLE 9

A 200 g (0.45 mol) sample of Triaryl Phosphate VI is chlorinated in 700 ml of chlorobenzene adding 0.77 mol of Cl₂ (170 minutes, at 4.5 mmol per minute) according to the procedure described in Example 1. Removal of the solvent leaves 231 g of a slightly yellow oil. This oil is heated at 90° for 3 hours under vacuum (pressure of 0.4 mm Hg) to remove any residual chlorobenzene, giving 228 g of reaction mixture. This mixture decolorizes bromine in carbon tetrachloride, indicating the presence of an olefin. The reaction mixture is then heated to 175° with 2 g of zinc chloride under nitrogen, while stirring with a magnetic stirrer, for 40 hours. The product on cooling is a dark viscous gum (almost glass). This is poured while warm into a Waring blender and 1500 ml of methanol is added. The mixture is blended for 5 minutes and the insoluble portion (a gum) is allowed to settle. The methanol (in which lower molecular weight fractions of the material are soluble) is decanted and the methanol-insoluble residue is dissolved in CH₂Cl₂. The CH₂Cl₂ solvent is then stripped leaving a brown solid (not tacky) weighing 115.5 g (58% from the starting phosphate). This material contains 2.11% residual chlorine and 7.1% phosphorus. It will be noted that the use of a smaller amount of chlorine (in this Example as compared to Example 8) produces a noncrosslinked methylene chloride-soluble product.

EXAMPLE 10

A solution of 500 g (1.24 mol) of Triaryl Phosphate IV (having an average of 1.85 isopropyl groups per phosphate) in 2 liters of chlorobenzene is chlorinated as described in Example 8 adding 2.26 mol chlorine or 1 equivalent per isopropyl group (3 hour 34 min addition, at a rate of 10.6 mmol/min as measured by the rotameter described in Example 1) at room temperature. Nitrogen sparge overnight removes the remaining HCl. The product at this point is mostly tertiary chloride

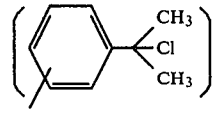

and some unreacted isopropyl groups. HCl is then split off by heating at 125° for 6 hours with 190 g (2.26 mol) of sodium bicarbonate. About 15 ml of H₂O is removed by distillation during this time. (Note: the NaHCO₃ procedure is used here for convenience to avoid pulling a large amount of HCl through the vacuum pump, as in Examples 8 and 11). The next day, the mixture is dried (over MgSO₄), filtered, and the solvent removed using high vacuum and rotary evaporator. The resulting reddish oil is heated to 120° C. at 0.5 mm Hg for 5 hours, removing some of the remaining HCl. The oil then weighs 519 g. This is then heated (in a 2-neck 1 liter flask equipped with a magnetic stirrer with a stream of N₂ flowing through the flask) to 155° C. with 10.4 g zinc metal (powdered) for 40 hours. The product, on cooling, is a viscous dark red gum which is soluble in CH₂Cl₂ indicating that no crosslinking had occurred. A vacuum distillation head is attached and 78 g (16%) of a light yellow liquid is distilled off at 0.7 mm Hg, pot temperature 270°–280° and head temperature of 220° C., over 6 hours. The residue, on cooling, is a red glass (407 g, 81% yield) which is ground in a Waring blender to a fine dark yellow solid. This product has a melting range of 83°–106° measured (at 10° C. per minute) on the Mettler FP1 apparatus described above. It has a solution viscosity of 0.93 centistokes as a 10% (wt/vol) solution in chloroform at 20° C. and contains 4.09% residual Cl and 8.20% P.

The light yellow distillate (78 g) described above is analyzed by glpc and found to be of the following approximate composition:

| | |
|---|---|
| triphenyl phosphate | 87% |
| 2-isopropylphenyl diphenyl phosphate | 3.8% |
| 3-isopropylphenyl diphenyl phosphate | 2.7% |
| di(2-isopropylphenyl) phenyl phosphate | 3.2% |
| Misc. phosphates | 3.3% |

Comparison with the starting phosphate mixture indicates that practically no triphenyl phosphate has reacted and a much lower percentage of the ortho isomer reacts as compared with the meta and para. This result may indicate that products of formula A above are formed or that a Friedel-Crafts reaction occurs under conditions in which substituted aromatic rings are preferentially involved. It contrasts with the results obtained using zinc chloride (Examples 8 and 9, above) where not much triaryl phosphate could be removed by vacuum distillation. In the latter case it appears that triaryl phosphates free of isopropenyl groups (such as those named just above) have coupled with the triaryl phosphates having such groups (or having corresponding halalkyl groups) by Friedel-Crafts reaction.

EXAMPLE 11

A sample of 100 g (0.24 mol) of Triaryl Phosphate V containing an average of 2.22 isopropyl groups per phosphate in 400 ml of chlorobenzene is chlorinated as described in Example 8 adding 0.53 mol $Cl_2$ over 120 minutes at room temperature (1 equivalent $Cl_2$/iPr). The solvent is removed using a rotary evaporator and high vacuum leaving 116.5 g of a yellow oil. This oil is heated under vacuum to 120°–125° for 2 hours to remove traces of chlorobenzene and HCl and the resulting olefin (similar to that described in Example 8) is heated for 40 hours with 2.0 g of zinc metal at 155°.

The product is then a reddish (light) viscous gum. Vacuum distillation (at up to about 290° pot temperature 0.5 mm Hg and 200°–220° head temperature over 1 hour) removes 28.4 g (28%) of a yellow oil. The residue is cooled to a light reddish glass which is ground in a morter and pestle to an off-white powder weighing 68.3 g (68%) after grinding (there are mechanical losses on grinding). This material has a melting range of 54°–75° (measured as in Example 10) and a solution viscosity of 0.62 centistokes as a 10% (wt/vol) solution in $CHCl_3$ at 20° C. It contains 3.20% residual chlorine and 7.61% phosphorus. The distillate again contains mostly triphenyl phosphate (27%), orthoisopropylphenyl diphenyl phosphate (22%) and di(2-isopropylphenyl) phenyl phosphate (17%).

It will be understood that the Friedel-Crafts catalyst may be added before the chlorinated material is heated; it is believed that in this case the isopropenyl compounds are formed as reactive intermediates during the heating.

The following Examples illustrate a much less desirable procedure and less desirable product, in which the initial chlorination is effected under such conditions that relatively large amounts (e.g. totalling some 45%) of the chlorine is present in dichloropropyl or trichloropropyl groups.

EXAMPLE 12

A 300 g (0.67 mol) sample of Triaryl Phosphate VI containing 2.85 isopropyl groups per phosphate in 1.1 liter of carbon tetrachloride is stirred with a magnetic stirrer under a flow of nitrogen for 10 minutes. Chlorine is bubbled into the solution through a pipet at a rate of 4.6 mmol per minute for 6 hours 15 minutes (1.73 mol $Cl_2$ added or 0.9 equivalents per isopropyl group) with a 375 watt sunlamp 4" from the flask. The flask is kept at room temperature by external cooling using a water bath, and a dry ice condenser prevents any loss of chlorine. The light is left on 15 minutes after addition is complete and the solution is again colorless. HCl is removed with a nitrogen sparge and the solvent removed using a rotary evaporator having 404.3 g of a yellow oil containing 19.21% Cl. The material at this point is a mixture of tertiary chlorides, di- and trichlorides. Chlorination here in carbon tetrachloride is not as specific toward tertiary chlorides as will be seen by Example 15 with di(4-isopropylphenyl) phenyl phosphate. The mixture of chlorides is heated with 0.5 g zinc chloride to 175° under $N_2$ stirred with a magnetic stirrer for 40 hours. HCl is given off and is trapped in aqueous sodium hydroxide. The product on cooling is a dark red viscous gum weighing 321 g and has a number average molecular weight of 1200.

A 181 g sample of this crude gum is dissolved in 200 ml of $CH_2Cl_2$ and poured into 2 l of methanol at 0° C. The methanol is decanted from the gummy precipitate and the precipitate dried using high vacuum giving 105.9 g (59%) of a brown solid which has a melting range of 65°–95°, a solution viscosity of 0.90 in chloroform (10% wt/vol) at 20° C., 5.80% residual chlorine and 7.1% phosphorus. It also has a number average molecular weight of 2480. As discussed above, the mixture of chlorides is thought to polymerize here via intermediate formation of an olefin via elimination of HCl (equilibrium) and subsequent Friedel-Craft condensation of the olefin and an aromatic ring catalyzed by zinc chloride.

EXAMPLE 13

A 400 g (0.93 mol) sample of Triaryl Phosphate VII containing 2.51 isopropyl groups per phosphate is chlorinated in 1.2 liters of carbon tetrachloride by the procedure described in Example 12, adding 2.33 mol of $Cl_2$ (220 min at a flow rate of 10.6 mmol of chlorine per minute). Removal of the solvent leaves 487.8 g of a light yellow oil containing 18.41% Cl. This mixture of chlorides is heated at 175° for 40 hours under nitrogen with 1 g of zinc chloride stirred with a magnetic stirrer. The product on cooling is a dark red viscous gum. A 272.7 g sample of this gum is added slowly to 2.5 liters of methanol in a Waring blender and mixed for 5 minutes. The product (a gummy substance) is allowed to settle and the methanol decanted. The product is then dissolved in methylene chloride, transferred to a flask and the solvent removed, leaving a tan solid (133.8 g, 49%) having 6.49% Cl, 7.2% phosphorus and a melting range of 69°–87° C. (measured as in Example 10).

EXAMPLE 14

A 150 g (0.34 mol) sample of Triaryl Phosphate VI containing an average of 2.85 isopropyl groups per phosphate dissolved in 450 ml carbon tetrachloride, stirred with a magnetic stirrer in a 1 liter 3-neck flask fitted with a dry ice trap and gas inlet adapter, is flushed with a stream of nitrogen for 10 minutes. Chlorine is then introduced through a pipet at a rate of 4.6 mmol per minute, for 250 minutes (1.15 mol chlorine added or 1.2 equivalents per isopropyl group) monitored by a calibrated rotameter (see Example 8) with a 375 watt sunlamp placed 4" from the reactor and a water cooling bath to keep the reaction at room temperature. The light is left on 15 minutes after addition of chlorine is complete and the solution is again colorless. The remaining HCl is removed by a nitrogen sparge and the solvent removed with a rotary evaporator giving 196.4 g of a yellow oil containing 22.28% Cl. The mixture then consisted of a mixture of tertiary chlorides,

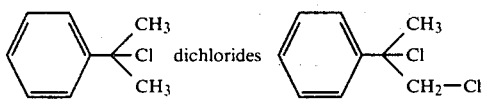

and trichlorides. As mentioned in Example 12, chlorination in carbon tetrachloride is not as specific toward tertiary benzylic chlorides as in prior examples in chlorobenzene and more chlorine is on the less reactive methyl positions. A 150 g portion of the mixture of chlorides is then heated to 175° for 40 hours with 0.5 g of zinc chloride under nitrogen with a magnetic stirrer for agitation. After 40 hours the material is a dark red gel at 175° and on cooling forms a hard glass which is broken with a spatula and ground in a ball mill to a fine dark yellow powder weighing 120 g (mechanical losses on grinding reduced the yield here) and having a residual chlorine content of 7.03% and phosphorus content of 7.1%. The material is insoluble in methylene chloride indicating extensive crosslinking has occurred.

EXAMPLE 15

A 150 g sample of di(4-isopropylphenyl) phenyl phosphate (0.37 mol) in 500 ml of carbon tetrachloride is chlorinated according to the procedure described in Example 8 adding 0.73 mmol of chlorine in 159 minutes (1 equivalent of chlorine per isopropyl groupd added). Removal of the solvent by rotary evaporator leaves 182.7 g of a light yellow oil having 16.33% chlorine. NMR analysis of this material shows it to be a mixture of chlorides with 50% of the isopropyl groups converted to the tertiary chloride (singlet at 1.95 ppm), 19% unreacted isopropyl groups (doublet at 1.2 ppm and multiplet centered at 3.0 ppm) and about 30% of the material is dichlorides and trichlorides (signals at 3.5–4.2 ppm and 2.05 ppm). The mixture of chlorides is heated to 180° under nitrogen under 0.4 g of zinc chloride using a magnetic stirrer. Heating is continued for 43 hours at which time the mixture is a red elastomer at 180° and cooled to a hard red glass which is chipped out of the flask with a spatula and ground in a morter and pestle to a yellow solid. The product is partially soluble and swells in chloroform indicating it to be crosslinked.

The entire product is heated with 600 ml of chloroform to about 60° until the material is dispersed. The insoluble material is removed by filtration and dried in a vacuum oven at 100° for 4 hours to give 122 g (74%) of a yellow solid, ground in a ball mill and having 2.74% Cl and 8.2% P. The chloroform solution is stripped leaving 39.5 g of a red gum. This gum is dissolved in 50 ml of chloroform and precipitated by pouring into 600 ml of methanol at 0°. The product settles out and the methanol is decanted. Drying the sample under high vacuum leaves 19.7 g (13%) of a yellow solid having 4.2% residual chlorine and 8.4% phosphorus.

The materials of the type shown in Examples 8–15 may be employed as fire retardants in plastics in the manner described previously with respect to the products made from MAC. They have high heat stability as indicated, for instance, by the DSC curves FIGS. 31 and 32 and impart improved flame resistance with little (or no) effect on heat distortion temperatures or Tg.

The proportions and conditions for the production of these materials may be varied widely. For instance (particularly when starting with Triaryl Phosphate V) it is preferred that the amount of chlorine supplied be in the range of about 0.3 to 1.2 or 1.5 molecules of $Cl_2$ per isopropyl group, that the proportion of solvent (e.g. chlorobenzene) be in the range of about 2 to 6 parts per part of triaryl phosphate, that the temperature of treatment of the chlorinated material be in the range of up to about 140° to 190° C., and that the amount of catalyst (e.g. zinc dust) be in the range of about 1 to 4%. It will be understood that other halogens, such as bromine, may be used instead of chlorine.

The intermediate dehydrohalogenation products, containing isopropenyl groups, are also useful as fire retardants. For this purpose the halogenated material may be used in partly or substantially completely dehydrohalogenated form. Thus, halogenation products (as described above) may be made, for instance, from any of the Triaryl Phosphate Mixtures tabulated above and dehydrohalogenated (without significant oligomerization), as by heating under vacuum, to give complex mixtures containing reaction products in which the isopropyl groups of the isopropylphenyl diphenyl phosphates, di(isopropylphenyl) phenyl phosphates, tri(isopropylphenyl) phosphates (as well as phosphates in which there are two or more isopropyl groups on a given benzene ring) have been converted partially (or even wholly) to isopropenyl groups. These materials are copolymerizably reactive and may be mixed with other olefinic materials, including such copolymerizable materials as are listed in U.S. Pat. No. 3,259,605, and subjected to polymerization conditions (as described, for instance, in said U.S. Pat. No. 3,259,605) to produce products of improved fire resistance, containing copolymerized phosphate chemically combined into the polymer and phosphate physically blended with the copolymer. The copolymerization may, it is believed, increase the compatibility between the physically blended phosphate and the high polymer (which may be crosslinked through phosphate groups). While it is preferred that the dehydrohalogenated (i.e. isopropenyl-containing) material be employed for this purpose without significant oligomerization thereof, it is within the broader scope of the invention to partly oligomerize the material (e.g. to increase its viscosity) before copolymerization. The halogenation products themselves (before dehydrohalogenation or after only partial dehydrohalogenation to various degrees) may themselves be employed as flame retardant additives in plastics (as illustrated, for instance, in Example 19 below).

Examples 16 to 18 below relate to the preparation and isolation of 4-isopropenylphenyl diphenyl phosphate (by halogenation and dehydrohalogenation) and its copolymerization with other olefinic materials. Examples 20–21 relate to the preparation and use of the complex isopropenyl-containing phosphate mixtures.

It is also within the broader scope of the invention to prepare isopropenylphenyl phosphates having one or two aliphatic groups (e.g. methyl, ethyl, propyl, isopropyl, n-butyl, sec-butyl, isobutyl, t-butyl, methoxyethyl, etc.) esterified to the

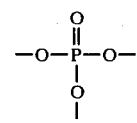

moiety, e.g. p-isopropenylphenyl dimethyl phosphate or m-isopropenylphenyl phenyl t-butyl phosphate.

These may be oligomerized or copolymerized in the same manner as the triaryl phosphates having the isopropenyl groups. One may also oligomerize compounds in which the olefinic moiety esterified to the phosphate is entirely aliphatic, e.g. diphenyl monoallyl (or methallyl) phosphate or allyl (or methallyl) di(ti-butyl) phosphate.

It is also within the broader scope of the invention to use sec-butylphenyl phosphates (in place of the corresponding isopropylphenylphosphates); these may be prepared by reacting phenol with butene-1 or butene-2 or mixtures thereof, as in the manner described in U.S. Pat. No. 3,576,923.

EXAMPLE 16

(a) A mixture of 4-isopropylphenyl diphenyl phosphate (25.0 g, 0.068 mol) and sodium octanoate (1.6 g) in 150 g of benzene is heated to reflux for 15 min with a stream of $O_2$ bubbling through the solution. The $O_2$ bubbling is stopped and bromine (34 g., 0.213 mol) is added dropwise over a 30 min period. A red color forms at first and after about 10 minutes the mixture again becomes colorless. Heating is continued for 1 hr after addition of bromine. The cooled mixture is diluted with 150 ml of ether and washed with 0.1 N sodium thiosulfate, 3 times with 5% NaOH, 1 time with water and dried (over $MgSO_4$). Removal of the solvent gives 42.7 g (100%) of a yellow-orange oil, having an nmr spectrum showing an AB quartet at 4.25 ppm (4H) and aromatic protons at 7.1–7.6 ppm (14H). Elemental analysis (calculated for $C_{21}H_{14}Br_3P$: Br, 39.93 and P, 5.16%) shows Br, 42.37%, P, 5.02%. The nmr spectrum and elemental analysis are consistent with the structure p-$(\alpha,\beta,\beta'$-tribromo)isopropylphenyl diphenyl phosphate.

(b) A 10 sample of the tribromide is heated at 50° under nitrogen with 10 g of zinc powder and 120 ml of acetic acid for 16.5 hours. The reaction mixture is cooled, diluted with 200 ml of ether and washed 5 times with 5% aqueous NaOH, 2 times with water and dried ($MgSO_4$). Removal of the solvent leaves 5.65 g (93%) of a slightly yellow oil which decolorizes bromine in carbon tetrachloride and, on thin layer chromatography on silica gel, using 15% ethyl acetate in hexane as the developing solvent, shows only one spot, with $R_f$ 0.50. Nmr shows 4 signals at 7.1–7.5 ppm (m, aromatic, 14H), 5.1 and 5.3 ppm (m, 2H, olefin) and 2.1 ppm (m, 3H, $CH_3$), and is consistent with the structure of 4-isopropenylphenyl diphenyl phosphate.

EXAMPLE 17

130 parts of a blend of styrene and ethylenically unsaturated polyester resins which are soluble in styrene and copolymerizable therewith is mixed with the following additives in the indicated amounts and with 6 parts of a 50:50 blend of benzoyl peroxide and tricresyl phosphate (e.g. the product sold as "Luperco ATC paste"), and then heat-cured in sealed glass tubes of ½ inch diameter (at 70° C.) overnight (16 hours). The cured material is then removed from its tube and its oxygen index is determined. Oxygen index is a measure of flame resistance (ASTM D2863).

The styrene-polyester resin solution is made by mixing 50 parts styrene, 50 parts Dion 6421 (a polyester of a slight excess of propylene glycol and a 1:1 [molar] mixture of maleic and isophthalic acid) and 30 parts Dow FR-1540 (a blend of 30% styrene and 70% of a polyester derived from maleic anhydride and dibromoneopentyl glycol).

The results are as follows:

| Additive | Oxygen Index |
|---|---|
| (a) None | 23 |
| (b) 20 parts of 4-isopropylphenyl diphenyl phosphate | 26 |
| (c) 10 parts of the product of Example 16B | 28.0 |
| (d) 20 parts of the product of Example 16B | 30 |

EXAMPLE 18

The product of Example 16B, 4-isopropenylphenyl diphenyl phosphate (2.5 g, 6.8 mmmol), styrene (2.5 g, 24 mmol), and di-t-butylperoxide (0.05 g) are placed in a sealed vial (screw cap) flushed with nitrogen and the vial is heated to 80°–90° for 16 hr., to 100°–110° for 24 hours, and then slowly (over 6 hr.) heated to 150° and then to 190° for 4 hours. The material on cooling is a solid reddish glass (the red color is probably due to attack of styrene on the unlined cap); it is dissolved in 50 ml of $CH_2Cl_2$, filtered, concentrated to 10–15 ml and poured into cold (0° C.) methanol (100 ml). A tan solid precipitates and is collected by filtration and dried under high vacuum to give 3.8 g (76%) of an off-white solid powder of number average molecular weight 2840, phosphorus content of 3.96%, and melting point of about 80° C. The phosphorus analysis indicates that the product may be a copolymer in which the mol ratio of the isopropenylphenyl diphenyl phosphate to styrene is about 1:4. The product may be employed as a non-plasticizing additive for fire retardance in plastics.

EXAMPLE 19

The product (tri-bromide) of Example 16B is milled into general purpose polystyrene at 275° F. and sheets of the resulting plastic are compression molded at 275° F. and tested for oxygen index with the following results:

| Parts additive per 100 parts of polystyrene | % Br in blend | % P in blend | Oxygen Index |
|---|---|---|---|
| 6.7 | 2.5 | 0.3 | 29.1 |
| 13.3 | 4.7 | 0.6 | 32.7 |

EXAMPLE 20

To a solution of 120 g of Triaryl Phosphate in 330 ml chlorobenzene there is added, over a period of about 4 hours, 45.5 g of chlorine. A stream of nitrogen is passed through the reaction mixture overnight to remove HCl formed in the chlorination reaction. Chlorobenzene is then stripped off under vacuum (30 mm Hg at 85° C.). The residue is then heated to effect dehydrochlorination while evolved gases (e.g. HCl) are passed through an Ascarite trap (NaOH on asbestos) at 120° C. for about 18 hours, then at 160° C. for about 5 hours, then at 145° C. for about 18 hours and finally at above 165° C. for several hours (about 3 hr) until the Ascarite trap no longer feels warm, indicating that no more HCl is being given off (after the first 160° C. treatment, very little HCl is formed). The product, weighing 131.5 g, contains about 9.9% chlorine, which indicates that almost half of the originally combined chlorine has been eliminated as HCl. The product is a viscous light yellow oil; (typically, its viscosity at 100° F. is about 200 centistokes).

EXAMPLE 21

Four parts of methyl methacrylate are mixed with 4 parts of the product of Example 20 and 0.2 parts of a 1/1 mixture of benzoyl peroxide and tricresyl phosphate. The material is placed in glass tubing, (of ½ inch diameter), purged with nitrogen, capped with a rubber septum, and heated for about a day (at a temperature which ranges from about 65°–100° C.) After standing overnight, the resulting rod is separated from the glass tubing. It is very clear and has a smooth surface. When subjected to a flame, in air, it is self-extinguishing, drips very little in the flame, forms a char and softens little.

"Pursuant to the requirements of the patent statutes, the principle of this invention has been explained and exemplified in a manner so that it can be readily practiced by those skilled in the art, such exemplification including what is considered to represent the best embodiment of the invention. However, it should be clearly understood that, within the scope of the appended claims, the invention may be practiced by those skilled in the art, and having the benefit of this disclosure, otherwise than as specifically described and exemplified herein."

What is claimed is:

1. A phosphate ester which imparts improved flame resistance to organic plastics, said ester having

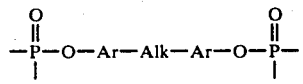

groups wherein Ar is a divalent aromatic radical having a single ring to which its valences are directly attached and Alk is an alkylene radical having a chain having a length of 2 carbon atoms between its attached Ar groups, said ester having a molecular weight such that it does not boil at a temperature of about 240° C. at a pressure of 0.2 mm Hg.

2. An ester as in claim 1 in which at least one of the carbons of said chain is a tertiary carbon.

3. An ester as in claim 1 having at least 3 phosphate groups.

4. A composition which imparts improved flame resistance to organic plastics, said composition comprising an ester as set forth in claim 1, said composition having a number average molecular weight of at least 540 and comprising a plurality of said esters, of different molecular weight.

5. A composition which imparts improved flame resistance to organic plastics, said composition comprising an ester as set forth in claim 1, said composition having a number average molecular weight of at least 700 and comprising a plurality of said esters, of different molecular weight.

6. A composition as in claim 5 in the form of a solid powder.

7. An ester as in claim 1 in which Ar is phenylene.

8. A composition as in claim 5 produced by alkylating a phenol with an aliphatic compound having two alkylating groups and then reacting with a phosphorylating agent to esterify phenolic groups.

9. A composition as in claim 8 in which said alkylating produces a mixture comprising a phenol which has not reacted with said compound and a reaction product of said phenol and said aliphatic compound, which reaction product contains an aliphatic substituent which is reactive with respect to the benzene ring of said unreacted phenol, and said mixture is then reacted with said phosphorylating agent.

10. A composition as in claim 9 in which said phosphorylation is effected with $POCl_3$ under alkylating conditions.

11. A composition as in claim 8 in which one of said alkylating groups comprises a halogen attached to an aliphatic carbon and the others is an olefinic group.

12. A composition as in claim 8 in which said aliphatic compound comprises methallyl chloride.

13. A composition as in claim 9 in which said reactive aliphatic substituent comprises a haloalkyl group or an olefinic group.

14. A composition as in claim 9 in which said mixture comprises a product of the coupling of two molecules of the starting phenol through alkylene radicals derived from said aliphatic compound.

15. A composition as in claim 6 in which some of said esters have free phenolic hydroxyl groups.

16. A composition as in claim 12 in which the starting phenol comprises phenol per se.

17. A composition as in claim 16 in which the starting phenol comprises a mixture of phenol per se and an isopropylphenol.

18. A composition as in claim 17 in which there are more than 10 isopropyl groups per 100 phenolic molecules in said starting phenol.

19. A composition as in claim 16 in which the phenol per se constitutes over 90% of the starting phenol.

20. A blend of flammable organic plastic and a flame retarding proportion of a phosphate ester as in claim 1.

21. A blend as in claim 20 in which said ester is a composition as in claim 5.

22. A blend as in claim 20 in which said ester is a composition as in claim 8.

23. A blend as in claim 20 in which said ester is a composition as in claim 12.

24. A blend as in claim 20 in which said ester is a composition as in claim 12 and said organic plastic comprises polyphenylene oxide.

25. A blend as in claim 20 in which said plastic comprises polystyrene.

26. A blend as in claim 20 in which said plastic comprises a blend of polystyrene and polyphenylene oxide.

27. A blend as in claim 20 whose Tg is within 10° C. of the Tg of said plastic.

28. A blend as in claim 20 in which said plastic comprises an ABS polymer.

29. A phosphorus ester which imparts improved flame resistance to organic flammable plastics, said ester having

the free valences on whose oxygen atoms being directly attached to phosphorus atoms wherein Ar is a divalent aromatic radical having a single ring to which the two valences of said aromatic radical are directly attached and Alk is an alkylene radical having a chain having a length of 2 carbon atoms between its attached Ar groups, said ester having a molecular weight such that it does not boil at a temperature of about 240° C. at a pressure of 0.2 mm Hg.

30. An ester as in claim 29 in which at least on of the carbons of said chain is a tertiary carbon.

31. A composition which imparts improved flame resistance to organic plastics, said composition comprising an ester, as set forth in claim 29, said composition having a number average molecular weight of at least 540 and comprising a plurality of said esters, of different molecular weights.

32. A composition which imparts improved flame resistance to organic plastics, said composition comprising an ester, as set forth in claim 29, said composition having a number average molecular weight of at least 700 and comprising a plurality of said esters, of different molecular weights.

33. A composition as in claim 32 produced by a process comprising alkylating a phenol with an aliphatic compound having two alkylating groups and then esterifying the reaction product with an ester-forming phosphorus compound to form a mixture containing said ester.

34. A composition as in claim 33 in which at least one of the carbons in said chain is a tertiary carbon and in which said composition also contains esters, produced in said process, which esters have

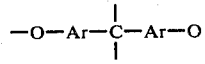

groups, the free valences on whose oxygen atoms are directly attached to phosphorus atoms and the free valences on whose

atom are each directly attached to hydrogen or lower alkyl.

35. A composition as in claim 8 in which at least one of the carbons in said chain is a tertiary carbon and in which said composition also contains esters, produced in said process, which esters have

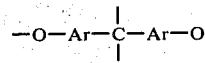

groups, the free valences on whose oxygen atoms are directly attached to phosphorus atoms and the free valences on whose

atom are each directly attached to hydrogen or lower alkyl.

36. A blend of flammable organic plastic and a flame retarding proportion of a phosphorus ester as in claim 29.

37. A composition which imparts improved flame resistance to organic plastics, said composition comprising a plurality of esters, as set forth in claim 1,
    the esters of said plurality being of different molecular weights, and including at least one ester (X) having a single

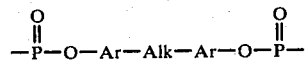

group, and having only two phosphorus atoms, and having a molecular weight lower than those of the other esters of said plurality,
    the number average molecular weight of said composition being at least equal to the molecular weight of said ester X.

* * * * *

UNITED STATES PATENT AND TRADEMARK OFFICE
CERTIFICATE OF CORRECTION

PATENT NO. : 4,246,169

DATED : January 20, 1981

INVENTOR(S) : Robert D. Norris; E. Robert Fretz, Jr.; Harry H. Beacham

It is certified that error appears in the above—identified patent and that said Letters Patent is hereby corrected as shown below:

Column 1, line 66, "cause by" should read --cause reaction by--. Column 3, line 10, "and" should read --or--. Column 5, line 67, "of" should read --or--. Column 7, line 43, "methallylchloride" should read -- methallyl chloride--. Column 9, line 34, "this all" should read --this is all--. Column 10, line 7, "Mixature" should read --Mixture--. Column 10, line 20, "mixature" should read --mixture--. Column 11, line 8, "hydroxyls." should read --hydroxyls.)--. Column 12, line 23, insert "(a)" before 968. Column 12, line 36, "hearted" should read --heated--. Column 14, line 32, "solubility the" should read --solubility in the--. Column 17, line 51, "temperatures." should read --temperatures).--. Column 19, lines 6-7, "application patent no." should read --German published application 2,708,447--. Column 19, line 8, "phosphate" should read --phosphates--. Column 19, line 37, "axotibisobutyronitrile)," should read --azobisisobutyronitrile),--. Column 19, lines 59-60, "phosphorochloridate" should read --phosphochloridate--. Column 20, line 39, "reaction." should read --reactions.--. Column 20, lines 52-53 "dimethalyll" should read --dimethallyl--. Column 21, line 49, "(Superfiltrol)" should read --(Super Filtrol)--. Column 23, line 51, "amd" should read --and--. Column 24, line 30, under VI, "$<5$" should read --$>5$--. Column 24, line 31, under VI, "$>1$" should read --$<1$--. Column 24, line 57, "condensor" should read --condenser--. Column 25, line

UNITED STATES PATENT AND TRADEMARK OFFICE
CERTIFICATE OF CORRECTION

PATENT NO. : 4,246,169

DATED : January 20, 1981

INVENTOR(S) : Robert D. Norris; E. Robert Fretz, Jr.; Harry H. Beacham

It is certified that error appears in the above—identified patent and that said Letters Patent is hereby corrected as shown below:

45, "it largely" should read --it is largely--. Column 27, line 30, "morter" should read --mortar--. Column 29, line 28, "groupd" should read --group--. Column 29, line 42, "morter" should read --mortar--. Column 29, line 48, "122 g" should read --112 g--. Column 29, line 50, "2.74%" should read --2.47%--. Column 31, line 6, "di(ti-butyl)" should read --di(t-butyl)--. Column 31, line 19, "150 g" should read --150 ml--. Column 31, line 59, "1/2" should read --1/4--. Column 32, line 16, "6.8 mmmol), should read --6.8 mmol),--. Column 33, line 9, "1/2" should read --1/4--. Column 35, line 1, claim 30, "on" should read --one--.

Signed and Sealed this

Second Day of March 1982

[SEAL]

Attest:

GERALD J. MOSSINGHOFF

Attesting Officer     Commissioner of Patents and Trademarks